US008182441B2

(12) United States Patent
Swain et al.

(10) Patent No.: US 8,182,441 B2
(45) Date of Patent: May 22, 2012

(54) METHODS AND DEVICES FOR INTRAGASTRIC SUPPORT OF FUNCTIONAL OR PROSTHETIC GASTROINTESTINAL DEVICES

(75) Inventors: Christopher Paul Swain, London (GB); Cole Chen, Westlake Village, CA (US); Mitchell Dann, Wilson, WY (US); Greg Fluet, Minneapolis, MN (US); John Hancock, Santa Barbara, CA (US); Josiah Verkaik, Lompoc, CA (US); Gerard von Hoffmann, Trabuco Canyon, CA (US); James Wright, Carpinteria, CA (US)

(73) Assignee: ValenTx, Inc., Carpinteria, CA (US)

( * ) Notice: Subject to any disclaimer, the term of this patent is extended or adjusted under 35 U.S.C. 154(b) by 377 days.

(21) Appl. No.: 12/136,003

(22) Filed: Jun. 9, 2008

(65) Prior Publication Data
US 2009/0012553 A1 Jan. 8, 2009

Related U.S. Application Data

(60) Provisional application No. 60/942,975, filed on Jun. 8, 2007, provisional application No. 61/023,809, filed on Jan. 25, 2008.

(30) Foreign Application Priority Data

Jun. 6, 2008 (WO) ................ PCT/US2008/066214

(51) Int. Cl.
*A61M 1/36* (2006.01)
(52) U.S. Cl. ................................. 604/9; 604/8
(58) Field of Classification Search .................. 604/8, 9, 604/96.01, 93.01; 606/191; 623/23.68
See application file for complete search history.

(56) References Cited

U.S. PATENT DOCUMENTS

| | | | |
|---|---|---|---|
| 4,134,405 A | 1/1979 | Smit | |
| 4,217,664 A | 8/1980 | Faso | |
| 4,235,238 A | 11/1980 | Ogiu et al. | |
| 4,252,131 A | 2/1981 | Hon et al. | |
| 4,315,509 A | 2/1982 | Smit | |
| 4,329,995 A | 5/1982 | Anthracite | |
| 4,501,264 A | 2/1985 | Rockey | |
| 4,532,926 A | 8/1985 | O'Holla | |

(Continued)

OTHER PUBLICATIONS

U.S. Appl. No. 11/431,040, filed May 1, 2006, Kagan et el.

(Continued)

*Primary Examiner* — Leslie Deak
(74) *Attorney, Agent, or Firm* — Knobbe, Martens, Olson & Bear LLP

(57) ABSTRACT

Disclosed herein are systems and methods for attaching or maintaining the position of a therapeutic or diagnostic device in a body lumen, such as the GI tract without necessarily requiring any penetrating attachments through any body walls. The system can include at least two elements: a proximal orientation element and a distal support element. The proximal orientation element can be configured to reside at least partially within the esophageal lumen and the distal support element can be configured to reside in the stomach, such as along the greater curve of the stomach. An intragastric support system can have a first configuration in which the long axis of the proximal orientation element is substantially parallel and/or substantially coaxial with the long axis of the distal support element, and a second configuration in which the long axis of the proximal orientation element is not substantially coaxial with the long axis of the distal support element. The second configuration can thus advantageously retain the intragastric support system in place and prevent unwanted proximal migration of the distal support element into the esophagus or distal migration into the intestine.

20 Claims, 54 Drawing Sheets

U.S. PATENT DOCUMENTS

| | | | |
|---|---|---|---|
| 4,630,609 | A | 12/1986 | Chin |
| 4,641,653 | A | 2/1987 | Rockey |
| 4,719,916 | A | 1/1988 | Ravo |
| 4,763,653 | A | 8/1988 | Rockey |
| 4,846,836 | A | 7/1989 | Reich |
| 4,905,693 | A | 3/1990 | Ravo |
| 4,946,440 | A | 8/1990 | Hall |
| 5,085,661 | A | 2/1992 | Moss |
| RE34,021 | E | 8/1992 | Mueller et al. |
| 5,171,305 | A | 12/1992 | Schickling et al. |
| 5,236,423 | A | 8/1993 | Mix et al. |
| 5,306,300 | A | 4/1994 | Berry |
| 5,314,473 | A | 5/1994 | Godin |
| 5,411,508 | A | 5/1995 | Bessler et al. |
| 5,431,666 | A | 7/1995 | Sauer et al. |
| 5,458,573 | A | 10/1995 | Summers |
| 5,470,337 | A | 11/1995 | Moss |
| 5,582,616 | A | 12/1996 | Bolduc et al. |
| 5,645,568 | A | 7/1997 | Chervitz et al. |
| 5,785,684 | A | 7/1998 | Zimmon |
| 5,820,584 | A | 10/1998 | Crabb |
| 5,824,008 | A | 10/1998 | Bolduc et al. |
| 5,843,164 | A | 12/1998 | Frantzen |
| 5,861,036 | A | 1/1999 | Godin |
| 5,887,594 | A | 3/1999 | LoCicero, III |
| 5,957,940 | A | 9/1999 | Tanner et al. |
| 5,972,023 | A | 10/1999 | Tanner et al. |
| 5,997,556 | A | 12/1999 | Tanner |
| 6,113,609 | A | 9/2000 | Adams |
| 6,193,733 | B1 | 2/2001 | Adams |
| 6,254,642 | B1 | 7/2001 | Taylor |
| 6,264,700 | B1 | 7/2001 | Kilcoyne et al. |
| 6,285,897 | B1 | 9/2001 | Kilcoyne et al. |
| 6,312,437 | B1 | 11/2001 | Kortenbach |
| 6,338,345 | B1 | 1/2002 | Johnson et al. |
| 6,387,104 | B1 | 5/2002 | Pugsley, Jr. et al. |
| 6,409,656 | B1 | 6/2002 | Sangouard et al. |
| 6,447,533 | B1 | 9/2002 | Adams |
| 6,494,888 | B1 | 12/2002 | Laufer et al. |
| 6,520,974 | B2 | 2/2003 | Tanner et al. |
| 6,535,764 | B2 | 3/2003 | Imran et al. |
| 6,544,291 | B2 | 4/2003 | Taylor |
| 6,558,400 | B2 | 5/2003 | Deem et al. |
| 6,558,429 | B2 | 5/2003 | Taylor |
| 6,592,596 | B1 | 7/2003 | Geitz |
| 6,595,911 | B2 | 7/2003 | LoVuolo |
| 6,626,916 | B1 | 9/2003 | Yeung et al. |
| 6,626,919 | B1 | 9/2003 | Swanstrom |
| 6,675,809 | B2 | 1/2004 | Stack et al. |
| 6,699,263 | B2 | 3/2004 | Cope |
| 6,702,735 | B2 | 3/2004 | Kelly |
| 6,736,828 | B1 | 5/2004 | Adams et al. |
| 6,740,121 | B2 | 5/2004 | Geitz |
| 6,746,489 | B2 | 6/2004 | Dua et al. |
| 6,764,518 | B2 | 7/2004 | Godin |
| 6,773,452 | B2 | 8/2004 | Shaker |
| 6,790,237 | B2 | 9/2004 | Stinson |
| 6,845,776 | B2 | 1/2005 | Stack et al. |
| 7,037,344 | B2 | 5/2006 | Kagan et al. |
| 7,120,498 | B2 | 10/2006 | Imran et al. |
| 7,121,283 | B2 | 10/2006 | Stack et al. |
| 7,152,607 | B2 | 12/2006 | Stack et al. |
| 7,175,669 | B2 | 2/2007 | Geitz |
| 7,220,284 | B2 | 5/2007 | Kagan et al. |
| 7,267,694 | B2 | 9/2007 | Levine et al. |
| 7,288,099 | B2 | 10/2007 | Deem et al. |
| 7,306,614 | B2 | 12/2007 | Weller et al. |
| 7,309,341 | B2 | 12/2007 | Ortiz et al. |
| 7,314,489 | B2 | 1/2008 | McKenna et al. |
| 7,329,285 | B2 | 2/2008 | Levine et al. |
| 7,347,875 | B2 | 3/2008 | Levine et al. |
| 7,354,454 | B2 | 4/2008 | Stack et al. |
| 7,371,215 | B2 | 5/2008 | Colliou et al. |
| 7,483,754 | B2 | 1/2009 | Imran et al. |
| 7,520,884 | B2 | 4/2009 | Swanstrom et al. |
| 2001/0044595 | A1 | 11/2001 | Reydel et al. |
| 2001/0056282 | A1 | 12/2001 | Sonnenschein et al. |
| 2002/0016607 | A1 | 2/2002 | Bonadio et al. |
| 2002/0026214 | A1 | 2/2002 | Tanner et al. |
| 2002/0035370 | A1 | 3/2002 | Kortenbach |
| 2002/0040226 | A1 | 4/2002 | Laufer et al. |
| 2002/0082621 | A1 | 6/2002 | Schurr et al. |
| 2002/0111658 | A1 | 8/2002 | Greenberg et al. |
| 2002/0165589 | A1 | 11/2002 | Imran et al. |
| 2002/0183768 | A1 | 12/2002 | Deem et al. |
| 2002/0188354 | A1 | 12/2002 | Peghini |
| 2003/0014064 | A1 | 1/2003 | Blatter |
| 2003/0018358 | A1 | 1/2003 | Saadat |
| 2003/0040804 | A1 | 2/2003 | Stack et al. |
| 2003/0040808 | A1 | 2/2003 | Stack et al. |
| 2003/0055313 | A1 | 3/2003 | Anderson et al. |
| 2003/0055442 | A1 | 3/2003 | Laufer et al. |
| 2003/0065340 | A1 | 4/2003 | Geitz |
| 2003/0120285 | A1 | 6/2003 | Kortenbach |
| 2003/0130560 | A1 | 7/2003 | Suzuki et al. |
| 2003/0139752 | A1 | 7/2003 | Pasricha et al. |
| 2003/0181929 | A1 | 9/2003 | Geitz |
| 2003/0191497 | A1 | 10/2003 | Cope |
| 2003/0208209 | A1 | 11/2003 | Gambale et al. |
| 2004/0002734 | A1 | 1/2004 | Fallin et al. |
| 2004/0024427 | A1 | 2/2004 | Imran et al. |
| 2004/0044364 | A1 | 3/2004 | DeVries et al. |
| 2004/0059349 | A1 | 3/2004 | Sixto, Jr. et al. |
| 2004/0059354 | A1 | 3/2004 | Smith |
| 2004/0087976 | A1 | 5/2004 | DeVries et al. |
| 2004/0087977 | A1 | 5/2004 | Nolan et al. |
| 2004/0092892 | A1 | 5/2004 | Kagan et al. |
| 2004/0093065 | A1 | 5/2004 | Yachia et al. |
| 2004/0097986 | A1 | 5/2004 | Adams |
| 2004/0097987 | A1 | 5/2004 | Pugsley et al. |
| 2004/0102855 | A1 | 5/2004 | Shank |
| 2004/0116949 | A1 | 6/2004 | Ewers et al. |
| 2004/0117031 | A1 | 6/2004 | Stack et al. |
| 2004/0122453 | A1 | 6/2004 | Deem et al. |
| 2004/0122456 | A1 | 6/2004 | Saadat et al. |
| 2004/0122473 | A1 | 6/2004 | Ewers et al. |
| 2004/0133089 | A1 | 7/2004 | Kilcoyne et al. |
| 2004/0133147 | A1 | 7/2004 | Woo |
| 2004/0133219 | A1 | 7/2004 | Forsell |
| 2004/0133238 | A1 | 7/2004 | Cerier |
| 2004/0138525 | A1 | 7/2004 | Saadat et al. |
| 2004/0138529 | A1 | 7/2004 | Wiltshire et al. |
| 2004/0138761 | A1 | 7/2004 | Stack et al. |
| 2004/0143342 | A1 | 7/2004 | Stack et al. |
| 2004/0147958 | A1 | 7/2004 | Lam et al. |
| 2004/0162567 | A9 | 8/2004 | Adams |
| 2004/0162568 | A1 | 8/2004 | Saadat et al. |
| 2004/0167546 | A1 | 8/2004 | Saadat et al. |
| 2004/0181242 | A1 | 9/2004 | Stack et al. |
| 2004/0186514 | A1 | 9/2004 | Swain et al. |
| 2004/0193190 | A1 | 9/2004 | Liddicoat et al. |
| 2004/0199189 | A1 | 10/2004 | Gifford et al. |
| 2004/0220682 | A1 | 11/2004 | Levine et al. |
| 2004/0225183 | A1 | 11/2004 | Michlitsch et al. |
| 2004/0225305 | A1 | 11/2004 | Ewers et al. |
| 2004/0243152 | A1 | 12/2004 | Taylor et al. |
| 2004/0243195 | A1 | 12/2004 | Imran et al. |
| 2004/0249362 | A1 | 12/2004 | Levine et al. |
| 2004/0249367 | A1 | 12/2004 | Saadat et al. |
| 2005/0033240 | A1 | 2/2005 | Oishi et al. |
| 2005/0033331 | A1 | 2/2005 | Burnett et al. |
| 2005/0049718 | A1 | 3/2005 | Dann et al. |
| 2005/0065401 | A1 | 3/2005 | Saadat et al. |
| 2005/0075653 | A1 | 4/2005 | Saadat et al. |
| 2005/0075654 | A1 | 4/2005 | Kelleher |
| 2005/0080431 | A1 | 4/2005 | Levine et al. |
| 2005/0080444 | A1 | 4/2005 | Kraemer et al. |
| 2005/0085787 | A1 | 4/2005 | Laufer |
| 2005/0096750 | A1 | 5/2005 | Kagan et al. |
| 2005/0101977 | A1 | 5/2005 | Gannoe |
| 2005/0125020 | A1 | 6/2005 | Meade et al. |
| 2005/0143784 | A1 | 6/2005 | Imran |
| 2005/0177181 | A1 | 8/2005 | Kagan et al. |
| 2005/0187567 | A1 | 8/2005 | Baker et al. |
| 2005/0192629 | A1 | 9/2005 | Saadat et al. |
| 2005/0197714 | A1 | 9/2005 | Sayet |
| 2005/0197715 | A1 | 9/2005 | Kugler et al. |

| | | |
|---|---|---|
| 2005/0203547 A1 | 9/2005 | Weller et al. |
| 2005/0222592 A1 | 10/2005 | Gannoe et al. |
| 2005/0228413 A1 | 10/2005 | Binmoeller et al. |
| 2005/0228504 A1 | 10/2005 | Demarais |
| 2005/0247320 A1 | 11/2005 | Stack et al. |
| 2005/0261549 A1 | 11/2005 | Hewit et al. |
| 2005/0261712 A1 | 11/2005 | Balbierz et al. |
| 2005/0267499 A1 | 12/2005 | Stack et al. |
| 2005/0267595 A1 | 12/2005 | Chen et al. |
| 2006/0009858 A1 | 1/2006 | Levine et al. |
| 2006/0015125 A1 | 1/2006 | Swain |
| 2006/0020164 A1 | 1/2006 | Butler et al. |
| 2006/0020247 A1 | 1/2006 | Kagan et al. |
| 2006/0020254 A1 | 1/2006 | von Hoffmann |
| 2006/0020277 A1 | 1/2006 | Gostout et al. |
| 2006/0020278 A1 | 1/2006 | Burnett et al. |
| 2006/0025819 A1 | 2/2006 | Nobis et al. |
| 2006/0047289 A1 | 3/2006 | Fogel |
| 2006/0064120 A1 | 3/2006 | Levine et al. |
| 2006/0074458 A1 | 4/2006 | Imran |
| 2006/0155312 A1 | 7/2006 | Levine et al. |
| 2006/0155375 A1 | 7/2006 | Kagan et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0173422 A1 | 8/2006 | Reydel et al. |
| 2006/0206063 A1 | 9/2006 | Kagan et al. |
| 2006/0206064 A1 | 9/2006 | Kagan et al. |
| 2006/0235446 A1 | 10/2006 | Godin |
| 2006/0247718 A1 | 11/2006 | Starkebaum |
| 2006/0265021 A1 | 11/2006 | Herbert et al. |
| 2006/0265082 A1 | 11/2006 | Meade et al. |
| 2006/0287734 A1 | 12/2006 | Stack et al. |
| 2006/0293742 A1 | 12/2006 | Dann et al. |
| 2007/0005147 A1 | 1/2007 | Levine et al. |
| 2007/0010794 A1 | 1/2007 | Dann et al. |
| 2007/0010864 A1 | 1/2007 | Dann et al. |
| 2007/0010865 A1 | 1/2007 | Dann et al. |
| 2007/0010866 A1 | 1/2007 | Dann et al. |
| 2007/0027548 A1 | 2/2007 | Levine et al. |
| 2007/0027549 A1 | 2/2007 | Godin |
| 2007/0032879 A1 | 2/2007 | Levine et al. |
| 2007/0083271 A1 | 4/2007 | Levine et al. |
| 2007/0100367 A1 | 5/2007 | Quijano et al. |
| 2007/0106313 A1 | 5/2007 | Golden et al. |
| 2007/0156248 A1 | 7/2007 | Marco et al. |
| 2007/0198074 A1 | 8/2007 | Dann et al. |
| 2007/0208360 A1 | 9/2007 | Demarais et al. |
| 2007/0219571 A1 | 9/2007 | Balbierz et al. |
| 2007/0225555 A1 | 9/2007 | Stefanchik |
| 2007/0233162 A1 | 10/2007 | Gannoe et al. |
| 2007/0293885 A1 | 12/2007 | Binmoeller |
| 2008/0004606 A1 | 1/2008 | Swain et al. |
| 2008/0009888 A1 | 1/2008 | Ewers et al. |
| 2008/0033574 A1 | 2/2008 | Bessler et al. |
| 2008/0058840 A1 | 3/2008 | Albrecht et al. |
| 2008/0058887 A1 | 3/2008 | Griffin et al. |
| 2008/0103604 A1 | 5/2008 | Levine et al. |
| 2008/0167606 A1 | 7/2008 | Dann et al. |
| 2008/0167610 A1 | 7/2008 | Dann et al. |
| 2008/0167629 A1 | 7/2008 | Dann et al. |
| 2008/0195226 A1 | 8/2008 | Williams et al. |
| 2008/0208355 A1 | 8/2008 | Stack et al. |
| 2008/0208356 A1 | 8/2008 | Stack et al. |
| 2008/0208357 A1 | 8/2008 | Melanson et al. |
| 2008/0221597 A1 | 9/2008 | Wallace et al. |
| 2008/0228030 A1 | 9/2008 | Godin |
| 2008/0243071 A1 | 10/2008 | Quijano et al. |
| 2008/0249533 A1 | 10/2008 | Godin |
| 2008/0255587 A1 | 10/2008 | Cully et al. |
| 2008/0255594 A1 | 10/2008 | Cully et al. |
| 2008/0255678 A1 | 10/2008 | Cully et al. |
| 2008/0269797 A1 | 10/2008 | Stack et al. |
| 2009/0012356 A1 | 1/2009 | Dann et al. |
| 2009/0012541 A1 | 1/2009 | Dahl et al. |
| 2009/0012544 A1 | 1/2009 | Thompson et al. |
| 2009/0062881 A1 | 3/2009 | Gross et al. |
| 2010/0049224 A1 | 2/2010 | Vargas |

OTHER PUBLICATIONS

International Search Report, PCT App. No. PCT/US2008/66214.

Endoscopic suturing, C. Paul Swain MD, *Balliere's Clinical Gastroenterology*, vol. 13, No. 1. pp. 97-108, 1999.

Progression rate of self-propelled feeding tubes in critically ill patients, Mette M. Berger et al., *Intensive Care Med* Oct. 29, 2002, pp. 1768-1774.

Iatrogenic Intussusception: a Complication of Long Intestinal Tubes, Patricia Redmond, M.D., et al., *American Jounal of Gastroenterology*, vol. 77, No. 1, 1982, pp. 39-42.

Design and Testing of a New, Small Diameter, Single Stitch Endoscopic Sewing Machine, C.P. Swain et al., *Abstracts Submitted to A/S/G/E/ 1990*, Vo. 36, No. 2, 1990, pp. 213, 214.

Endoscopic Suturing of a Novel Gastroesophageal Antireflux Device (GARD) A Preliminary Report, N. J. Godin et al., *Gastrointestinal Endoscopy*, vol. 43, No. 4, 1996.

An endoscopic stapling device: the development of new flexible endoscopically controlled device for placing multiple transmural staples in gastrointestinal tissue, C. Paul Swain, MD et al., *Gastrointestinal Endoscopy*, vol. 35, No. 4, 1989 pp. 338-339.

An endoscopically deliverable tissue-transfixing device for securing biosensors in the gastrointestinal tract, C. Paul Swain, MD et al. *Gastrointestinal Endoscopy*, 1994 vol. 40 No. 6 pp. 730-734.

Development of a gastroplasty with variable diameter. Experimental study using artificial sphincters, M. Merlini et al., 1992 Abstract.

Synthetic Biodegradable Polymers as Medical Devices, John C. Middleton et al., *Medical Plastics and Biomaterials Magazine MPS Article Index*, Mar. 1998.

Experimental study on in situ tissue engineering of the stomach by an acellular collagen sponge scaffold graft, Hori Y. Nakamura et al., Abstract, May 2001.

Repair of Full-Thickness Defects in Alimentary Tract Wall with Patches of Expanded Polytetrafluoroethylene, Daniel S. Oh, MD et al., Annals of Surgery 2002; 235:708-712.

Stents in the small intestine, Singh S, Gagneja HK, Abstract, Oct. 2002.

Endoscopic vertical band gastroplasty with an endoscopic sewing machine, Amjad N. Awan MD et al., *Gastrointestinal Endoscopy*, vol. 55, No. 2, 2002, pp. 254-256.

A through-the-scope device of suturing and tissue approximation under EUS control, Annette Fritscher-Ravens, MD, et al., *Gastrointestinal Endoscopy*, vol. 56, No. 5, 2002, pp. 737-742.

Evaluation of porcine-derived small intestine submucosa as a biodegradable graft for gastrointestinal healing, SG del la Fuente et al., Abstract, J. Gastrointest Surg Jan. 2003.

Bard EndoCinch: the device, the technique and pre-clinical studies, Paul Swain, M.D. et al., *Gastrointestinal Endoscopy Clinics of North America*, 13, 2003 pp. 75-88.

Endoscopic suturing for gastroesophageal reflux disease: clinical outcome with the Bard Endocinch, Richard I. Rothstein, MD et al., *Gastrointestinal Endoscopy Clinics of North America*, 13 (2003) pp. 89-101.

Wilson-Cook sewing device: the device, technique, and preclinical studies, Michael Rosen MD, et al., *Gastrointestinal Endoscopy Clinics of North America*, 13 (2003) pp. 103-108.

Endoscopic full-thickness plication: the device, technique, pre-clinical and early clinical experience, Ram Chuttani, MD, *Gastrointestinal Endoscopy Clinics of North America*, 13 (2003) pp. 109-116.

Microvasive gastric stapler: the device, technique, and preclinical results, Tom R. De Meester MD, *Gastrointestinal Endoscopy Clinics of North America*, 13 (2003) pp. 117-133.

Endoscopic Gastropexy and Crural Repair for Gastro-Esophageal Reflux: Transgastric Surgery Under Endoscopic Ultrasound Control II, Anette Fritscher-Ravens et al. *Digestive Disease Week* 2003 Abstract.

Endoscopic suturing for treatment of GERD, m. Brian Fennerty, MD, *Gastrointestinal Endoscopy*, vol. 57, No. 3, 2003 pp. 390-395.

Transgastric gastropexy and hiatal hernia repair for GERD under EUS control: a porcine model, Annette Fritscher-Ravens, MD et al., *Gastrointestinal Endoscopy*, vol. 59, No. 1, 2004, pp. 89-95.

Effect of Duodenal-Jejunal Exclusion of a Non-obese Animal Model of Type 2 Diabetes, Francesco Rubino, MD et al., *Annals of Surgery*, vol. 239, No. 1, Jan. 2004, pp.

Successful Uses in Approximation Ligation & Fixation using the Quik-Stitch, Endoscopic Suturing System, Paré Surgical, Inc. Brochure 2001.

Microvasive WALLSTENT® Colonic and Duodenal Endoprosthesis, Boston Scientific website, www.bostonscientific.com, Sep. 20, 2002.

COOK® Wilson-Cook Medical GI Endoscopy, Wilson Cook: Biliary/Pancreatic Stents, www.cookgroup.com, Sep. 20, 2002.

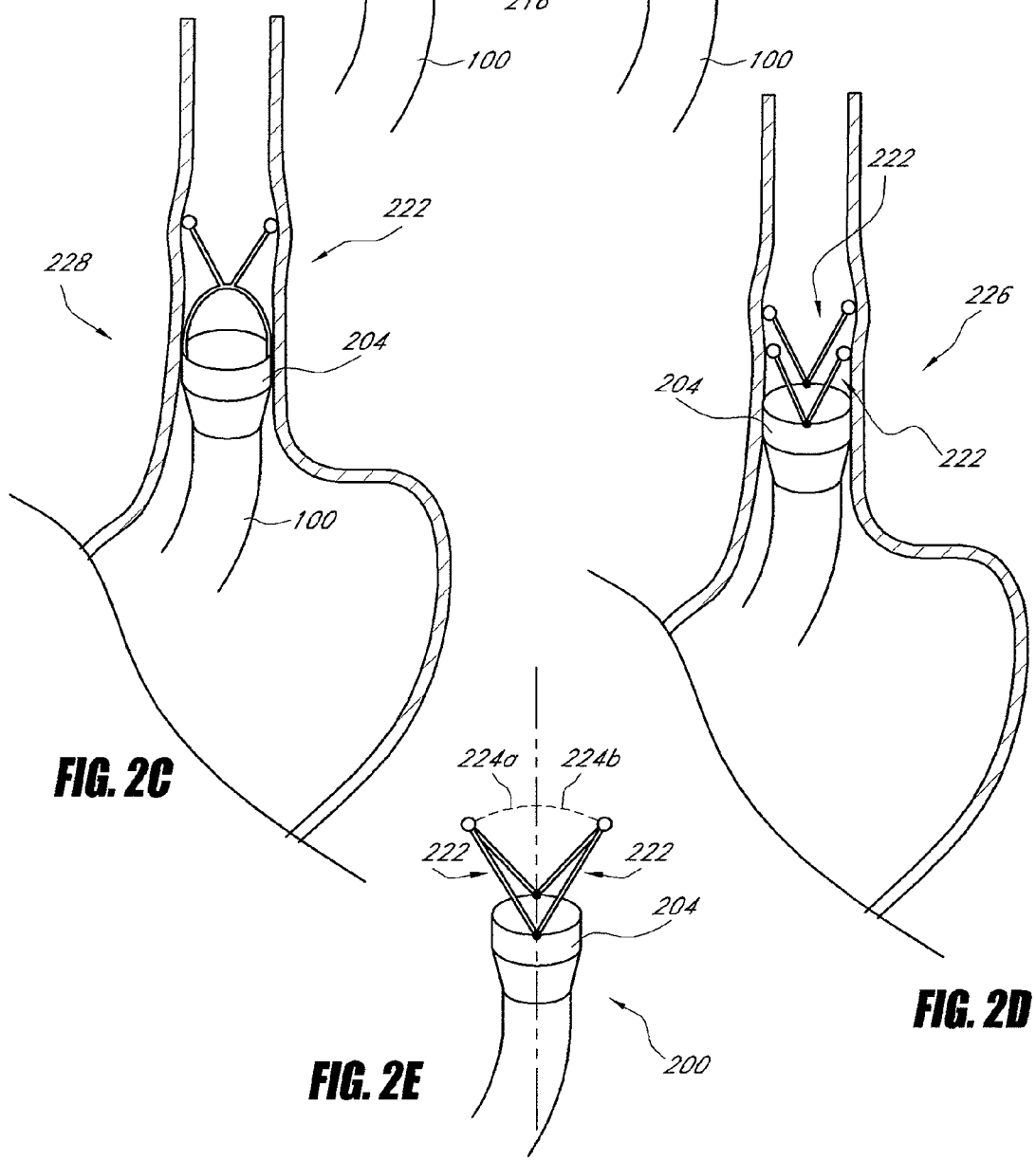

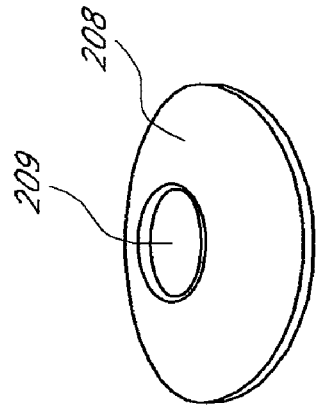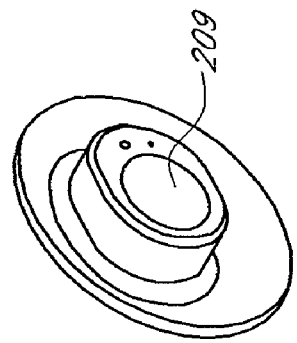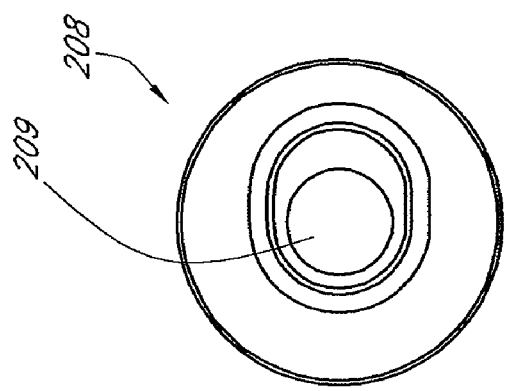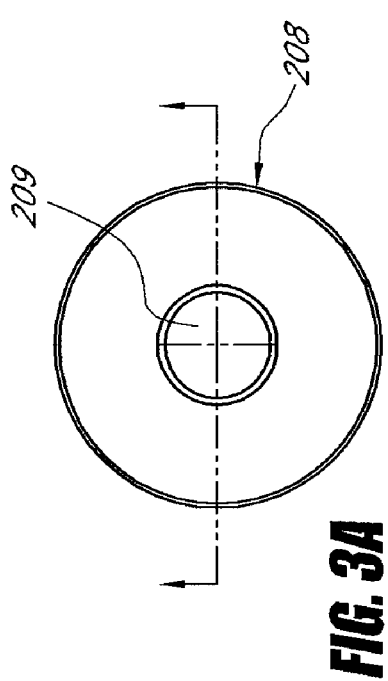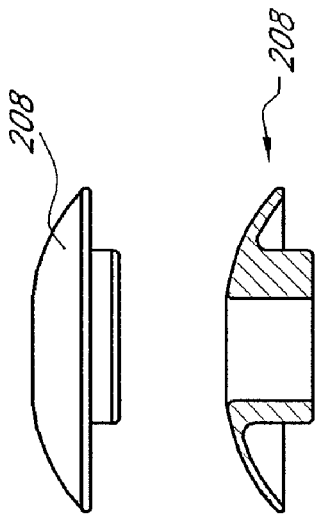

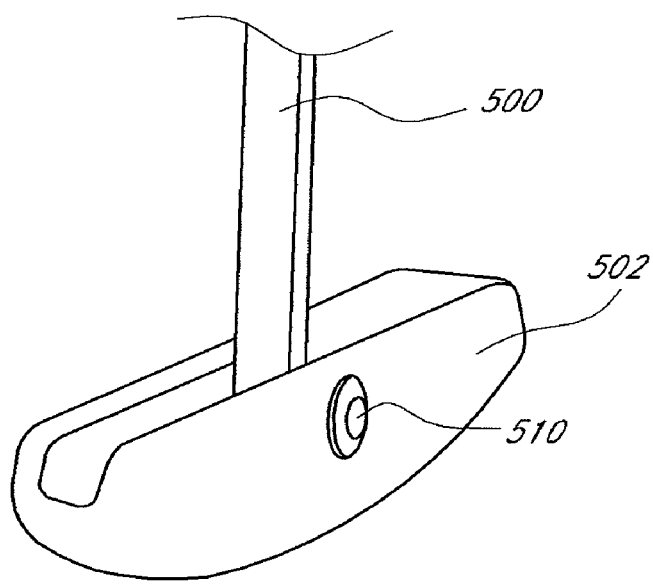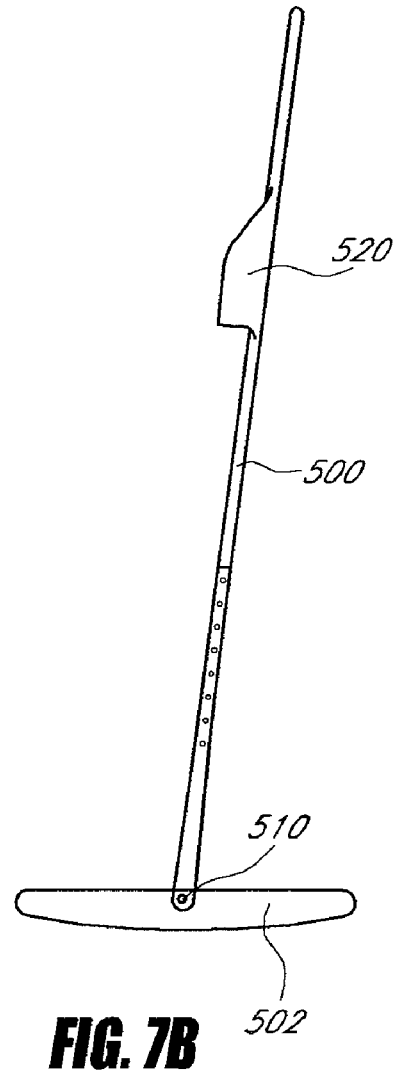
FIG. 7A  FIG. 7B

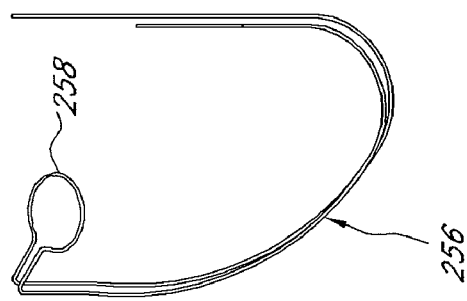
FIG. 8D
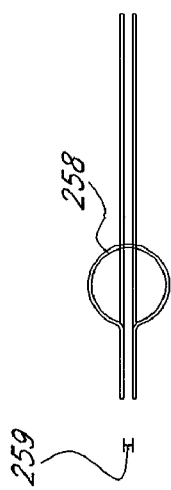
FIG. 8A
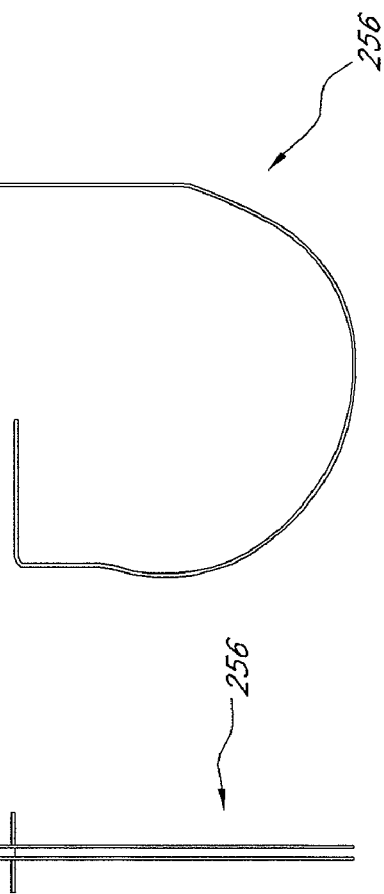
FIG. 8C
FIG. 8B

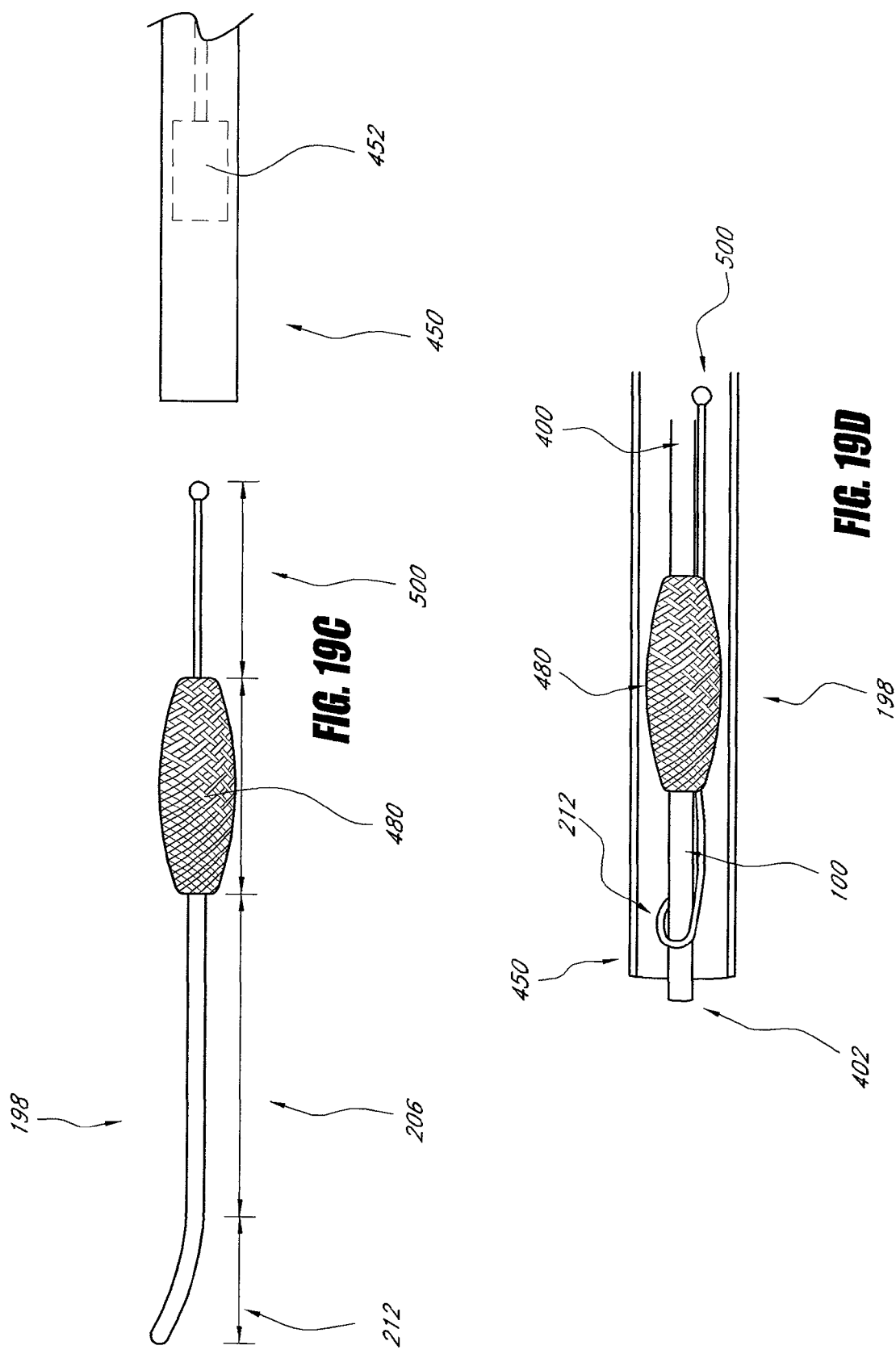

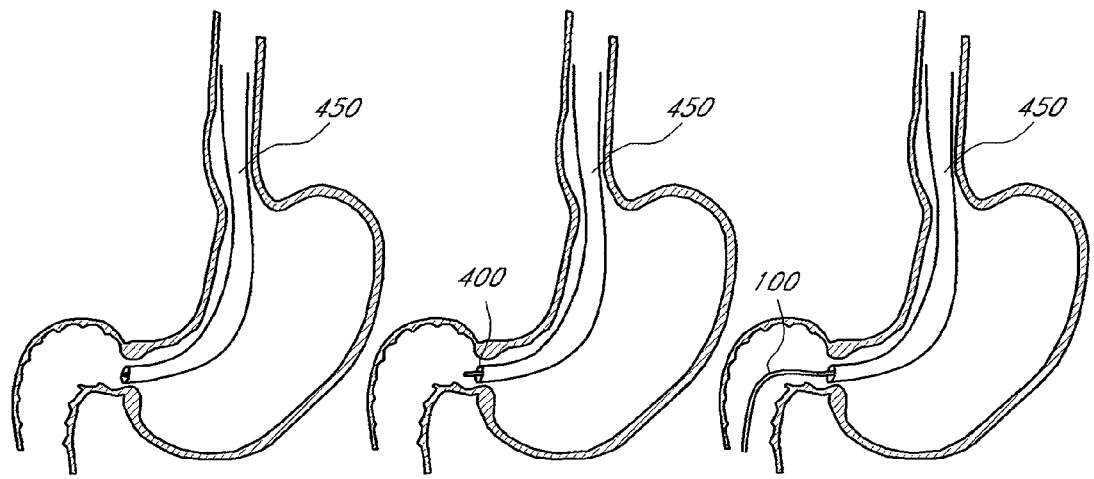
FIG. 19E  FIG. 19F  FIG. 19G
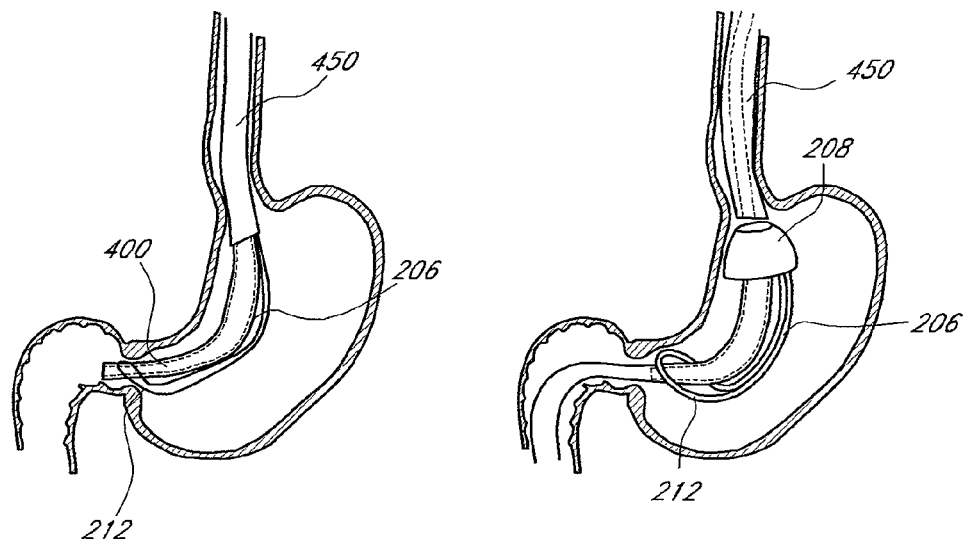
FIG. 19H  FIG. 19I

METHODS AND DEVICES FOR INTRAGASTRIC SUPPORT OF FUNCTIONAL OR PROSTHETIC GASTROINTESTINAL DEVICES

PRIORITY CLAIM

The present application claims priority under 35 U.S.C. §119(e) to U.S. Provisional Application No. 60/942,975, filed Jun. 8, 2007, and U.S. Provisional Application No. 61/023,809, filed Jan. 25, 2008, both of which are hereby incorporated by reference in their entireties.

APPLICATIONS INCORPORATED BY REFERENCE

Various features of, for example, gastrointestinal bypass sleeves, attachment cuffs, and/or toposcopic delivery methods that can be used or adapted for use with systems and methods disclosed herein can be found, for example, at U.S. patent application Ser. No. 10/698,148, filed Oct. 31, 2003, published May 13, 2004 as U.S. Patent Pub. No. 2004-0092892 A1 and entitled "APPARATUS AND METHODS FOR TREATMENT OF MORBID OBESITY" (and may be referred to herein as the "Kagan '148 application or Kagan '892 publication"); U.S. patent application Ser. No. 11/025,364, filed Dec. 29, 2004, published Aug. 11, 2005 as U.S. Patent Pub. No. 2005-0177181 A1 and entitled "DEVICES AND METHODS FOR TREATING MORBID OBESITY" (and may be referred to herein as the "Kagan '181 publication"); U.S. patent application Ser. No. 11/124,634, filed May 5, 2005, published Jan. 26, 2006 as U.S. Patent Pub. No. 2006-0020247 A1 and entitled "DEVICES AND METHODS FOR ATTACHMENT OF AN ENDOLUMENAL GASTROINTESTINAL IMPLANT" (and may be referred to herein as the "Kagan '247 publication"); U.S. patent application Ser. No. 11/400,724, filed Apr. 7, 2006, published Jan. 11, 2007 as U.S. Patent Pub. No. 2007-0010794 A1 and entitled "DEVICES AND METHODS FOR ENDOLUMENAL GASTROINTESTINAL BYPASS" (and may be referred to herein as the "Dann '794 publication"); and U.S. patent application Ser. No. 11/548,605, filed Oct. 11, 2006, published Aug. 23, 2007 as U.S. Pub. No. 2007-0198074 A1 and entitled "DEVICES AND METHODS FOR ENDOLUMENAL GASTROINTESTINAL BYPASS" (and may be referred to herein as the "Dann '605 application" or "Dann '074 publication") are hereby incorporated by reference in their entireties herein, as well as any additional applications, patents, or publications noted in the specification below.

SUMMARY OF THE INVENTION

In one embodiment, disclosed herein is an intraluminal support system, which can be a gastrointestinal, or intragastric support system in some embodiments, that includes a proximal orientation element and a distal support element. The proximal orientation element includes a proximal end and a distal end, and has a diameter sized to fit within the lumen of an esophagus. The long axis of the proximal orientation element can be substantially parallel with the long axis of the esophagus. The distal support element can be configured to reside within the stomach, such as along the greater curve of the stomach. The distal support element can be transformable from a first configuration where a long axis of the distal support element is configured to be substantially parallel with the long axis of the proximal orientation element during delivery to a second configuration where the long axis of the distal support element is configured to be not substantially parallel with the long axis of the proximal orientation element when implanted in the body. The proximal orientation element can include a food-collecting ring, which can include a proximal tapered portion and a distal cylindrical portion in some embodiments. The proximal tapered portion can include a first shoulder and a second shoulder. The second shoulder can be longitudinally offset from the first shoulder. The system can further include a joint configured to pivotably couple the proximal orientation element to the distal support element. The joint could be, for example, a ball-and-socket joint, or a hinged joint in other embodiments. The system can also include a gastrointestinal bypass sleeve, which can be attached to the food-collecting ring in some embodiments. The distal support element can include an enlarged distal end to retain the distal support element within the stomach. The distal support element can include a drug reservoir. The proximal orientation element can include a rounded proximal head to prevent esophageal trauma. In some embodiments, the proximal orientation element has a variable-length cross-section. The proximal orientation element can include a plurality of strut members in some embodiments. The distal support element can be transformable from a first reduced configuration to a second expanded configuration. In some embodiments, the system includes a restrictive element and/or an obstructive element operably connected to the food-collecting ring.

Also disclosed herein is a method of treating a patient, including the steps of providing an providing an intragastric support system, the system comprising a proximal orientation element having a proximal end and a distal end, and a distal support element; inserting the proximal orientation element and the distal support element into a gastrointestinal tract lumen, wherein a long axis of the proximal orientation element is substantially parallel to a long axis of the distal support element; positioning the system such that at least a portion of the proximal orientation element is within the esophagus of a patient and the distal support element is within the stomach of a patient; and transforming the distal support element such that the long axis of the distal support element is not substantially parallel to the long axis of the proximal orientation element. In some embodiments, transforming the distal support element is such that the long axis of the distal support element is substantially perpendicular to the long axis of the proximal orientation element. In some embodiments, the intragastric support system further includes a joint configured to pivotably couple the distal support element to the proximal orientation element, the joint having a locked state to prevent movement of the distal support element with respect to the proximal orientation element. In some embodiments, the method further includes the step of locking the joint at a position wherein a long axis of the proximal orientation element is at least substantially coaxial with a long axis of the distal support element during delivery; and unlocking the joint to allow the distal support element to pivot within a range of motion with respect to the proximal orientation element when the distal support element is implanted in the stomach.

In some embodiments, the proximal orientation element is configured to reside at least partially within the esophageal lumen while the distal support element is configured to reside within the stomach, such as along the greater curve of the stomach. The gastrointestinal support system has a first configuration in which the long axis of the proximal orientation element is coaxial or substantially coaxial with the long axis of the distal support element, and a second configuration in which the long axis of the proximal orientation element is not substantially coaxial with the long axis of the distal support element, to retain the gastrointestinal support system in place and prevent unwanted proximal migration of the distal support element into the esophagus or distal migration into the intestine.

In one embodiment, disclosed is an intragastric support system. In some embodiments, the system can be used for positioning a prosthetic or functional device within the GI tract. While the intragastric support most preferably includes at least one component within the stomach, other components of the system may reside partially or completely outside of the stomach, such as, for example, in the esophagus and/or intestines as well. The system need not be attached transmurally to a wall of the GI tract. The system can include a proximal orientation element, a support component, and a distal retention component (also referred to as a pyloric support component). The system can also include a sleeve connected to the support component and/or proximal orientation element, or other various devices such as an anti-reflux device, a drug-eluting device, a stimulator, a volume-occupying device, or a chemical, biochemical or physiologic parameter sensor such as a pH sensor. In some embodiments, the sleeve can be a gastric and/or intestinal bypass sleeve for bypassing at least a portion of the stomach and/or intestines.

In some embodiments, the proximal orientation component is connected to or is a part of the intragastric support component. The sleeve is connected to the intragastric support at one or more points, preferably at a location at or near the GEJ so that food leaving the esophagus flows into the sleeve with minimal leak. In other embodiments, the sleeve may be connected to a portion, such as a ring element of the proximal orientation element, which can be an esophageal post above the GEJ. One way to accomplish this is if the intragastric support component includes a gasket or baffle element, that may be dome-shaped in some embodiments, in the upper part of the stomach, the sleeve can be connected to an opening in the dome that aligns with the GEJ. The sleeve may also include a cuff portion as disclosed in, for example, the Kagan '148 application. The term "cuff/sleeve" as used herein may encompass embodiments with a sleeve, such as a gastric and/or intestinal bypass sleeve, cuff alone, or sleeve that includes a cuff. As used herein proximal refers to closer to the mouth in the implanted orientation, while distal refers to the "downstream" GI tract toward the anus. The proximal orientation component can be substantially linear, or spiral shaped in some embodiments. The proximal orientation component can also include one or more V-shaped posts. The proximal orientation component can also have an atraumatic tip portion that is flexible, or a rounded ball-like tip. In some embodiments, the proximal orientation component can be coated with a coating, such as a hydrophilic coating material. The proximal orientation component is preferably configured to reside at least partially within the esophagus. In some embodiments, the length of the proximal orientation component is no greater than the distance between the gastroesophageal junction distally and the level of the cricopharyngeous muscle proximally. In some embodiments, a proximal orientation element is configured to reduce reflux of gastric acids into the esophagus.

In other embodiments, the proximal orientation component may be or could include one or more strips of material attached to a sleeve. The strips may be made of a woven fiber, polymer, or a tissue graft and adhere to the walls of a body lumen such as the esophagus. In some embodiments, the strips are configured to promote tissue in-growth. In some embodiments, at least a portion of the mucosal surface of the esophagus is ablated or otherwise injured prior to installation of an attachment system. The ablation could be controlled to increase bonding of the system to the esophageal wall, accelerate tissue in-growth, and/or alter the tissue layers to provide a more durable attachment substrate. The surface may be injured using various energy forms, such as a laser, Argon Plasma Coagulation (APC), RF, microwave, thermal, cryo, or ultrasound energy, mechanical abrasion, or any of a variety of sclerosing agents known in the art.

In some embodiments, the distal support element can include a conical or dome-shaped support element that may be convex or concave or some complex form that is designed to mimic the shape of the upper part of the stomach. While this can be referred to as a dome-shaped element herein, the structure could be any other complex form as noted to mimic or fit within the upper part of the stomach and that can help prevent the device from migrating proximally into the esophagus. The dome-shaped element may have a lumen in which the cuff/sleeve can pass therethrough. The dome-shaped element may be sized and shaped such that the forces of the stomach acting on the proximal end are not able to significantly move the device where the cuff/sleeve is no longer aligned with the GEJ. In addition, the proximal end may be supplementally attached at or near the gastroesophageal junction or along the lesser or greater curve of the stomach at one or more places if necessary using any of the attachment methods previously disclosed in the disclosures incorporated by reference, above.

In some embodiments, the dome-shaped element may be implanted within the stomach in a first configuration with a low crossing profile and expanded to a second configuration with a second crossing profile. The dome-shaped element may be made of a polymeric or metal shape memory material to facilitate the transformation from the first to the second configuration. In other embodiments, the dome-shaped element may be transformed using a filler, such as a liquid polymerizable in situ. In some embodiments, the support element may be a nitinol basket, or helical shaped. In addition, the dome shaped element could be made up of component parts that lock together after placement in the stomach. This could be accomplished using key-slot type locking mechanisms or preferably magnets implanted in the components so the device self-assembles when the components are placed in the stomach.

The distal support element can include a connecting support element that can be arcuate-shaped, such as banana-shaped in some embodiments. The arcuate support element is preferably shaped to conform or cooperate with the shape of the greater curvature, or alternately in some embodiments, the lesser curvature of the stomach. The arcuate support element is preferably connected to or forms distally a pyloric retention element configured to prevent the system from migrating distally past the pylorus into the intestine. The support element could be a wire such as Nitinol or other alloy or metal with a distal stop such as a loop configured such that the system cannot pass through the pylorus. The wire can be covered with a silicon or polyurethane or other coating to make the device less traumatic to the wall of the stomach. In addition, the device could have a hydrophilic coating such as the HARMONY® Advanced Hydrophilic Coating from SurModics (Eden Prairie, Minn.).

In some embodiments, the arcuate element may be actuatable from a straighter or flexible configuration to a more rigid arcuate configuration. In this way, the device could be placed in the stomach while in a flexible or generally linear form and then utilizing a mechanical mechanism or the properties of the shape memory nature of nitinol be triggered to take an arcuate shape. One method to achieve this would be to shape set the nitinol in an arcuate form and then cool the material so that it is flexible. The device can be first implanted in a cold, more flexible form and then when the device warms due to the ambient temperature in the stomach it takes its arcuate shape.

The pyloric retention element may form a loop such that a sleeve configured to contain orally ingested materials may pass therethrough. Alternatively, the sleeve could go outside the loop so it is pinched between the stomach wall and the loop. This would in essence form a pinch valve and may be desirable to regulate the flow of food through the pylorus. The dome element, arcuate element, and pyloric support element may be integrally formed or assembled from component parts. In some embodiments, the distal support element includes one or more balloons. The balloons may be positioned near the gastroesophageal junction and/or the distal stomach near the pylorus. The balloons could serve to help anchor the device in place and keep it from being passed through the pylorus. In addition, the balloon or balloons could serve as volume occupying devices. Preferably the design of the structure is such that it does not significantly interfere with the ability of the stomach walls to move and have that motion transfer forces to the sleeve that helps move material through the sleeve. By having an arcuate structure in the greater curve, the stomach can still contract around the arcuate element and contact the sleeve. This allows the transmission of peristaltic motion to the sleeve to help keep food or other material moving through the sleeve.

In some embodiments, an intragastric support system (which can also be referred to as a GI attachment system) includes a proximal orientation element that can be in some embodiments an esophageal post with a ringed tubular element for connecting a sleeve above the GEJ, and a distal (e.g., intragastric) support element hingably connected to the proximal orientation element (e.g., esophageal post).

BRIEF DESCRIPTION OF THE DRAWINGS

FIGS. 2A-2E schematically illustrate embodiments of proximal orientation elements that are "V" shaped, according to one embodiment of the invention.

FIG. 2I schematically illustrates an embodiment of an intragastric support system including a proximal orientation element having a strut with a plurality of strut members, according to one embodiment of the invention.

FIGS. 3A-3F depict various views of a dome-shaped component of a distal support element, according to one embodiment of the invention.

FIG. 7A is a close-up perspective view of a distal (e.g., intragastric) support element, according to one embodiment of the invention.

FIG. 7B illustrates an intragastric support system similar to that illustrated in FIGS. 6A-6B.

FIGS. 8A-8D schematically illustrates an intragastric support system with a distal support element that includes a wire, according to one embodiment of the invention.

FIGS. 19A-I schematically illustrate delivery of an intragastric support system that includes a woven nitinol dome, according to one embodiment of the invention.

DETAILED DESCRIPTION OF THE PREFERRED EMBODIMENT

Figure 1A:
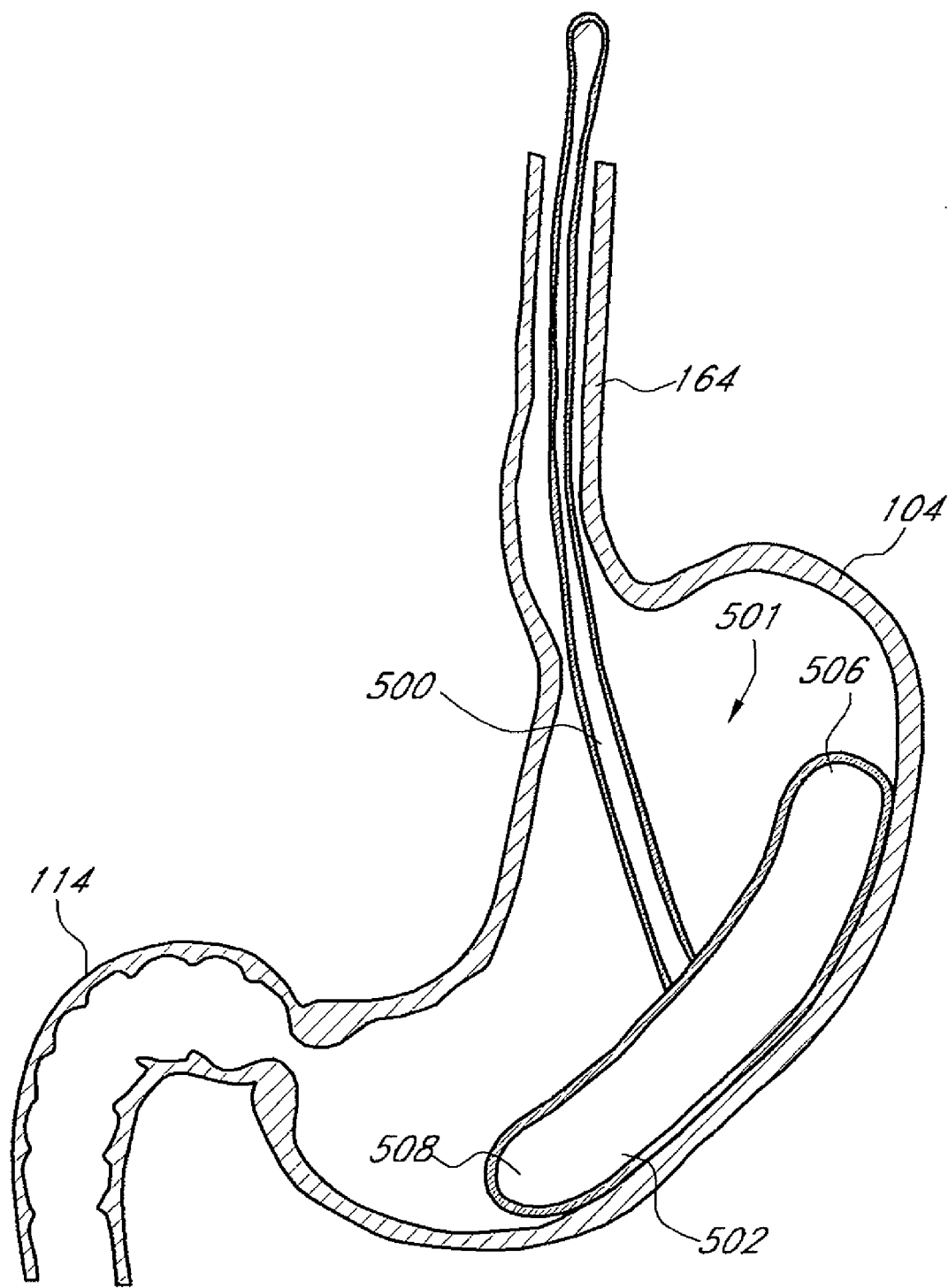
FIG. 1A schematically illustrates an intragastric support system that includes a proximal orientation element and a distal support element, according to one embodiment of the invention.
Figure 1B:
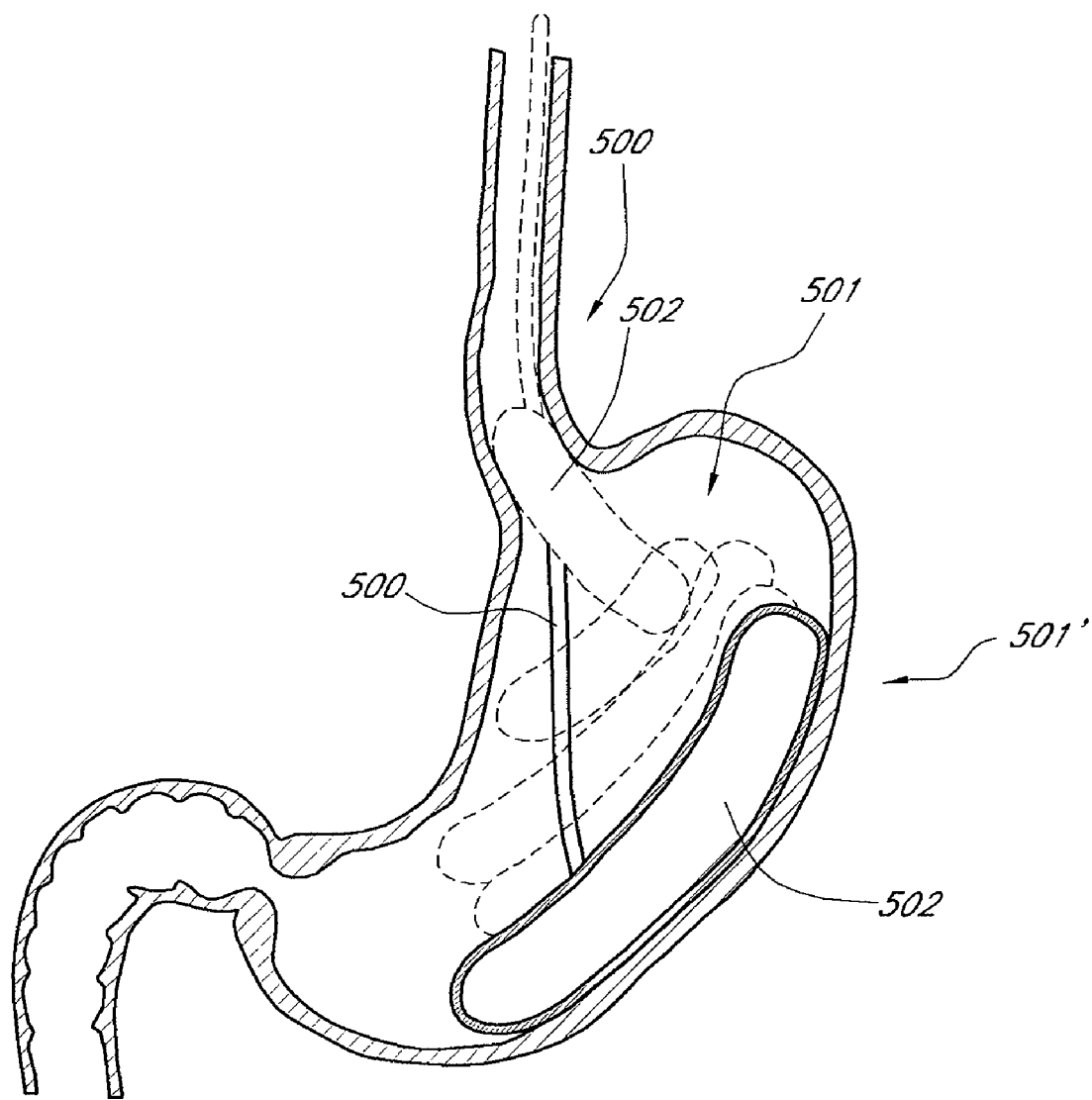
FIG. 1B illustrates an intragastric support system with a first delivery configuration and a second implanted configuration, according to one embodiment of the invention.

The invention relates, in some embodiments, to various structures forming a system for attaching or maintaining the position of a therapeutic or diagnostic device in a body lumen, such as the GI tract without necessarily requiring any penetrating attachments through any body walls. The system 501 can include at least two elements: (1) a proximal orientation element 500 and (2) a distal support element 502, as shown schematically in FIG. 1A. The proximal orientation element 500 can be configured to reside at least partially within the esophageal lumen and the distal support element 502 can be configured to reside in the stomach, such as along the greater curve of the stomach, in some embodiments. The proximal orientation element 500 may be integrally formed with the distal support element 502, or separately formed and coupled, such as via a joint 510 as will be described elsewhere in the application. The distal support element 502 could be unitary, or include several different subcomponents in other embodiments. As illustrated in FIG. 1B, the intragastric support system has a first configuration 501 (shown in phantom) in which the long axis of the proximal orientation 500 element is coaxial or substantially coaxial with the long axis of the distal support element 502, and a second configuration 501' in which the long axis of the proximal orientation element 500 is not substantially coaxial with the long axis of the distal support element 502. The second configuration 501' can thus advantageously retain the intragastric support system in place and prevent unwanted proximal migration of the distal support element 502 into the esophagus or distal migration into the intestine, as the distal support element 502 has at least one diameter that is larger than a diameter of the distal esophagus and pylorus, respectively. In some embodiments, in the second implanted configuration of the intragastric support system, the long axis of the distal support element and the long axis of the proximal orientation element intersect and form an angle of between about 30-90 or 45-75 degrees, or are perpendicular or substantially perpendicular in other embodiments. The system can transform from the first configuration 501 to the second configuration 501' via a variety of mechanisms, such as, for example, actuation of a hinge or ball-and-socket joint between the proximal orientation element 500 and distal support element 502, deformation of the distal support element 502 via bending or shape memory material, expansion via, e.g., a balloon or expandable polymer. The system can, in some embodiments, transform from the second non-coaxial configuration 501' back into the first coaxial configuration 501 to promote removal of the system from the body lumen.

Methods and devices disclosed to accomplish this could be used in conjunction with a wide variety of devices including any of the embodiments, combinations, or subcombinations of those described in any of the aforementioned applications listed above in the section "Applications Incorporated by Reference" above. For illustrative purposes, an intragastric support system described, in some embodiments, is configured to support a cuff and/or gastrointestinal bypass sleeve and/or optional stoma device that has been previously described in some of the aforementioned applications previously incorporated by reference. Instead of, or in addition to a cuff and/or sleeve, these intragastric support systems as described could also aid in the placement of various diagnostic and therapeutic devices, such as gastric stimulators, volume occupying devices such as bezoars or balloons, or diagnostic devices such pH detectors. Some other non-limiting examples of devices that can be secured using the attachment systems described herein include: a drug eluting device which could release substances into the stomach and be refilled endoscopically; hanging device for cameras or capsules in the stomach; device that monitors consumption of specific substances (calories, fat, cholesterol, alcohol, drugs, poisons) and optionally triggers a system to reduce the effects of consumption through one or more of: stimulation to increase or decrease motility or regurgitation, release of a stored emetic, release of a diuretic, release of an antidote; volume and/or flow restrictive device (with or without sleeve), and/or a device which stores, emits, and receives data. The device may also function as a device to reduce gastroesophageal reflux, creating a barrier to reflux with the use of a valve or flap.

A preferred location for the cuff/sleeve device, in some embodiments, is to have the cuff placed at or near the gastroesophageal junction (GEJ) and the sleeve attached or coupled to the cuff. In a preferred embodiment, the distal end of the sleeve resides in the intestine, distal to the ligament of Treitz. This preferred embodiment is intended to replicate a Roux-en-Y gastric bypass with an endoscopically implanted device. However, other implantation locations are also within the scope of the invention, and can be selected by one of ordinary skill in the art depending on the desired clinical result. The intragastric support systems described could be used and/or modified to attach any of the aforementioned disclosed devices in any position of the GI tract that can, for example, provide the desired results of reduction in weight and/or resolution of comorbidities associated with obesity. Alternatively, the bypass sleeve could be held with the proximal end of the sleeve at or past the pylorus or elsewhere in the structure. In this example, a restrictive element could still be provided by modifying the design by adding a GEJ flow restrictor, such as by modifying a silicone dome, to restrict flow out of the GEJ. In other embodiments, the dome could support a separate stoma device at the GEJ, or there could be no restrictive element at all. In addition, the cuff may not be necessary in some cases and the device could just be a bypass sleeve. For ease of description, the words "cuff/sleeve" and bypass sleeve will often be used to describe any bypass sleeve that is used as a conduit for ingested food or liquid to bypass a section of the GI tract. Note the bypass sleeve could be any embodiment of those described in the previous aforementioned applications incorporated by reference. For example, sleeve material and embodiments, for example, can be as described in previous disclosures, such as disclosed in the Kagan '892 publication, for example, at FIGS. 11-31 and the accompanying disclosure at, e.g., paragraphs [0241] to [0312] of the '892 publication, or, for example, at paragraphs [0174] to [0185] of the Dann '074 publication, both of which are incorporated by reference in their entirety.

Attachment of the device can be achieved through a wide variety of means; attachment as disclosed herein refers to the fact that the device can hold its position in or near a desired location in the GI tract. The attachment need not necessarily penetrate any wall of the GI tract.

Figure 1C:
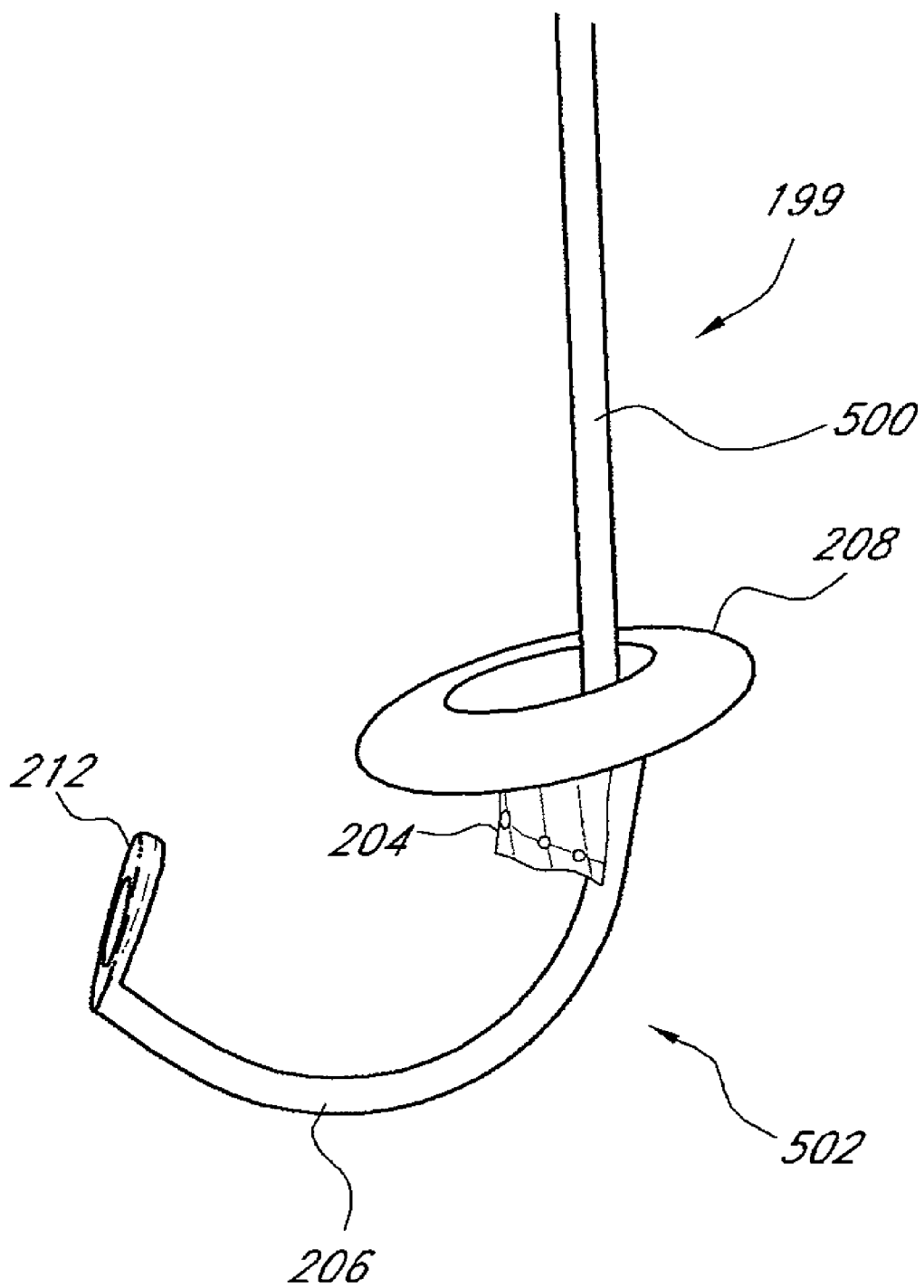
FIG. 1C is a side perspective view of an intragastric support system that includes a proximal orientation element, a distal support element operably connected to a cuff/sleeve element, wherein the distal support element includes an arcuate support element, and a pyloric support element, according to one embodiment of the invention.
Figure 1D:
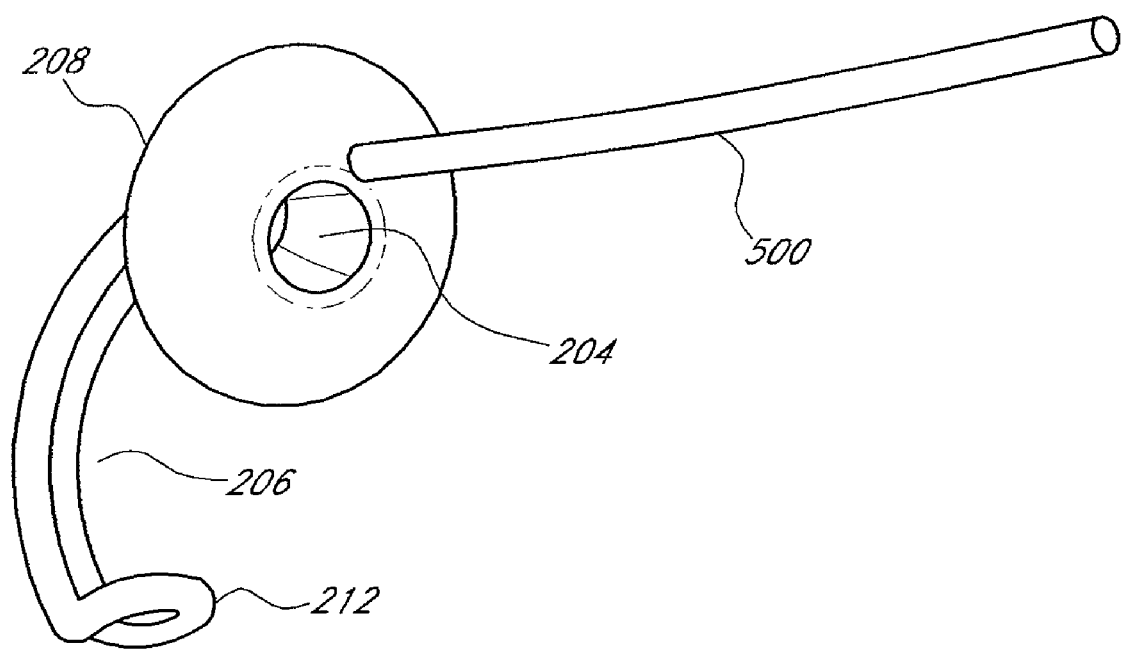
FIG. 1D is a top perspective view of the intragastric support system of FIG. 1C that better depicts the top portion of the distal support element.
Figure 1E:
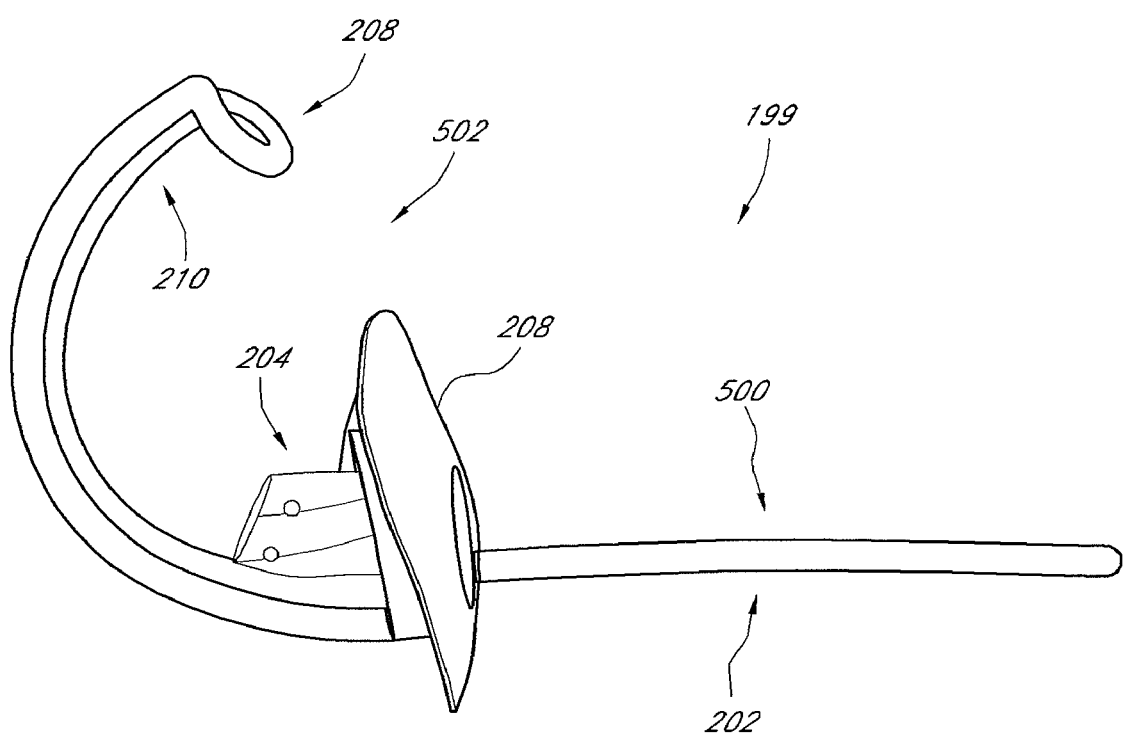
FIG. 1E is a side perspective view of an intragastric support system with a proximal orientation element that has an atraumatic tip portion, according to one embodiment of the invention.

As illustrated in FIGS. 1C-1E, which are perspective views of one embodiment of an intragastric support system for holding a prosthetic or functional device within the GI tract. One preferred embodiment of the system 199 includes three primary components: (1) a proximal (e.g., esophageal) orientation element 500 (e.g., a proximally extending tube or post), (2) a cuff 204 and/or sleeve (only a cuff 204 is shown in FIGS. 1C-1E for clarity), and (3) a distal (e.g., intragastric) support component 502. The distal support component 502 shown here includes a flexible dome 208 (which can be other shapes as well to conform to the shape of the upper stomach and prevent migration of the distal support element proximally into the esophagus), arcuate support component 206, and a pyloric support element 212. While all of these elements are shown together in this device 199, it should be understood that some of these elements could be used by themselves or with other embodiments to provide additional securement in addition to other previously described ways to attach a bypass sleeve such as transmural attachment. FIG. 1D illustrates that the cuff can be configured to fit at least partially within a lumen of the flexible dome 208 as shown.

Proximal Orientation Element

Structures are disclosed that may be deployed in the esophagus, and are designed to attach to or extend from the proximal end of the cuff/sleeve construct or proximal gastric support construct. These structures can also be configured to keep the proximal opening of the cuff/sleeve oriented in communication with the opening from the GEJ. In a preferred embodiment, the proximal orientation elements have mechanical properties that keep them in position without being anchored to or causing trauma to the esophageal wall. Alternatively, these structures could be fixedly attached to the lumen of the esophagus using a variety of possible devices including t-tags, adhesives, sutures, stents, or other devices that will be appreciated by one of ordinary skill in the art. In some embodiments, the proximal orientation element 500 could be actively or passively expanded or contracted in one or more dimensions. In other words, the proximal orientation element could be expanded or contracted, for example, in an axial direction with a motor or some control means that could be mechanical. In some embodiments, there is a telescoping or spring-loaded component to produce the desired clinical result. This may be, in some embodiments, controlled via a remote transmitter, or automated, such as by a sensing mechanism.

As shown in the schematic FIGS. 2A-2E, in one embodiment, the proximal orientation element could be an esophageal post, e.g., a substantially linear element that can receive, for example, the proximal end of the cuff/sleeve construct. The proximal orientation element is preferably flexible enough to be atraumatic to the esophageal mucosa, yet stiff enough to resist dislocation from its preferred orientation that keeps the cuff approximately coaxially aligned with the GEJ. In some embodiments, the proximal end of the proximal orientation element could have an atraumatic tip to reduce the risk of damage to the esophagus. This can be done, for example, with either a very flexible proximal segment or with a rounded loop or ball-like tip as shown in FIGS. 2A-2E. An embodiment 199 with a single post 202 and an atraumatic tip portion 201 is shown schematically in FIG. 1E. Two or three or four or more alignment structures (e.g., posts) may alternatively be used. The atraumatic tip 201 can also be a soft and/or spongy ball, bullet-shaped silicone tip or ball, or other type of atraumatic tip. In some embodiments, the entire post 202 can be coated with a hydrophilic coating or other material to help reduce the risk of food adhering to the construct, reduce corrosion, or reduce its impact on surrounding tissue. The post 202 can have a variable durometer along its length. One example would be to have a higher durometer near the GEJ and a lower durometer over its length up the esophagus.

The length of the proximal orientation element 202 is preferably configured such that the proximal end does not come far enough proximally up the esophagus (toward the oral cavity) to be felt or sensed by the patient. The level of the cricopharyngeous muscle is considered to be the most proximal point (toward the oral cavity) in the esophagus where an object would be felt by the patient, therefore the length of the post should be such that the proximal end is below the cricopharyngeous. Generally, in some embodiments the alignment structure will extend at least about 1 cm, more preferably at least about 2 cm but no more than about 20 cm or no more than about 25 cm above the distal support element (and/or above the gastroesophageal junction).

A proximal orientation element as described above would preferably not provide force against the wall of the esophagus to "hang" the cuff/sleeve construct in place.

As shown in the embodiment 216 of FIG. 2A, the proximal orientation element can include two posts 202 attached at their base 218 to form a "V" alignment element could be used in a way to help proximally secure the cuff 204/sleeve 100 device. In this configuration the posts 202 would attach to the cuff 204 and have a "V"-like shape 222 as shown. The base 218 of the "V" element would be the proximal edge of the cuff 204 and/or gastric support at or near the GEJ. The posts 202 would spread the esophageal lumen open, which would help to orient the device 216 and the round tips 201 of the posts 202 would help provide resistance to vertical displacement. When not filled with food, the esophagus tends to lay flat on itself (in other words, the esophageal walls tend to keep the lumen relatively closed) so this would be a natural state. Because the "V" shape 222 will help to bias the esophageal lumen closed "flat", this can also advantageously prevent acid reflux back into the esophagus and treat GERD as well. In one embodiment 220, as shown in FIG. 2E, there could be more than one "V" element 222 used. The posts 202 comprising the "V" element 222 are preferably disposed at identical or substantially similar angles 224a, 224b relative to the long axis 224 of the cuff 204/sleeve 100, although different angles may be used. In one embodiment 226, as shown in FIG. 2D, two "V" elements 222 could be attached at opposite sides of the cuff 204. In this configuration, they could be optionally joined at the proximal end and separate at the base. This type of configuration could make a "change purse" type mechanism of action where squeezing the ends of the "V" opens the proximal end of the sleeve 100 and/or cuff, as shown in the system 228 illustrated in FIG. 2C. FIG. 2B illustrates a proximal orientation element that includes an esophageal post element 230 with a distance x between tips 201 of two posts 202 of a "V", a diameter y of a proximal end of a sleeve 100 and/or cuff 204; and a distance z representing a width of the posts at the intersection of the "V". As shown, the distance x is preferably greater than the distance y if the proximal end of the cuff/sleeve is connected to the attachment system 230 at the level of the GEJ. If the cuff 204 hangs distal to and is larger than the GEJ, the distance x could be the same or substantially the same as the distance y. In some embodiments, the distance x is wider than the relaxed width of the cuff 204, if the cuff 204 is sized to match the dimensions of the esophagus. The distance x can also be wider than the luminal diameter of the esophagus. However, it is preferred that the distance x is not so much greater than the diameter of the esophagus as to cause esophageal trauma from overstretching of the lumen. Preferably, the distance x is no more than about 130%, 125%, 120%, 115%, 110%, 105%, or less of the width of the diameter of either the cuff 204, the esophageal lumen, or both. In some embodiments, the cuff 204 can have a diameter of between about 20-40 mm, more preferably between about 23-31 mm. In other embodiments, the cuff 204 has a diameter of at least about 25 mm.

Figure 2F:
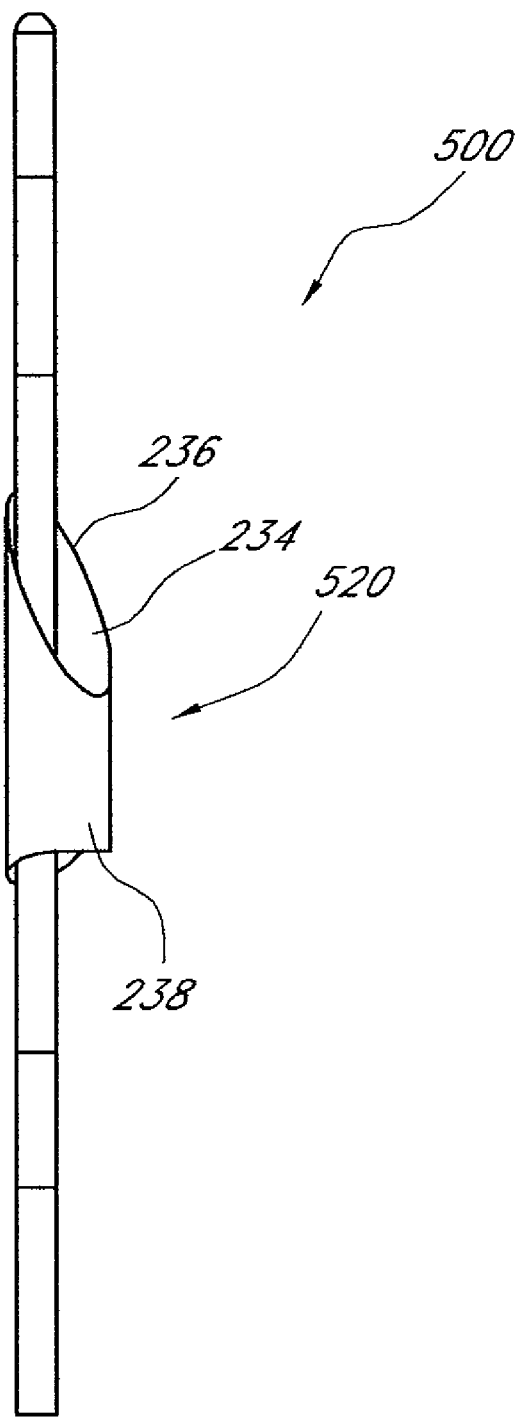
FIG. 2F schematically illustrates an embodiment of a proximal orientation element that includes a ring for collection of ingested contents, according to one embodiment of the invention.

In some embodiments as shown in FIG. 2F, the proximal orientation element 500 includes an esophageal post 500 having a tubular, or ringed element 520 with a proximal end 236 and a distal end 238 that can direct peroral contents such as food and liquids into a sleeve 100 (not shown) connectable to the ringed element 520. The proximal end 236 of the ringed element 500 may be tapered or beveled as shown in some embodiments, which may assist in collecting peroral contents.

The food-collecting ring 520, in some embodiments, has an outside diameter of between about 10-30 mm, such as between about 15-25 mm in some embodiments. The food collecting ring 520 is preferably configured to have sufficient column strength to keep a relaxed esophagus open, although the food collecting ring 520 can be collapsible by a peristaltic wave of the esophagus.

Figure 2G:
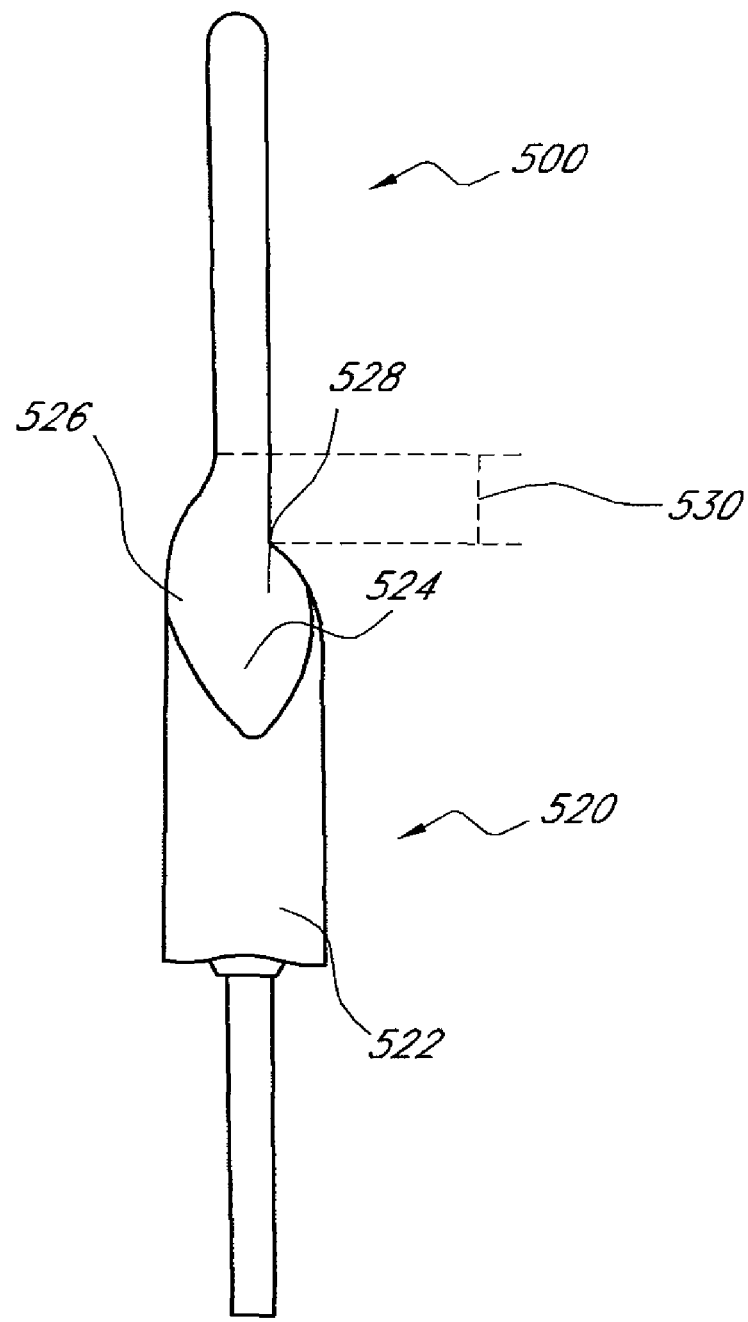
FIG. 2G schematically illustrates a proximal orientation element, e.g., an esophageal post element that includes a asymmetrically tapered food-collecting ring, according to one embodiment of the invention.

In some embodiments, the food collecting ring 520 has a distal cylindrical segment 522 and a proximal tapered segment 524, that may be beveled in some embodiments. The length of the proximal tapered segment 524 may be, in some embodiments, between about 30-70%, such as 40-60% of the entire length of the ring 520 in some embodiments. While the tapered segments 524 may be symmetric, in some embodiments as illustrated in FIG. 2G the tapered segment 524 may include a first shoulder portion 526 and a second shoulder portion 528 longitudinally offset from the first shoulder portion 526 in some embodiments, to form a "double helix"-like geometry. The longitudinal offset distance 530 may be, for example, between about 1-15 mm, such as between about 2-10 mm in some embodiments.

Such tapered ring configurations may be advantageous to more easily allow the device to move proximally and distally within the esophagus during delivery, removal, as well as while in use and to reduce friction and prevent "snagging" of the device within the esophagus. The ring structure can be configured to interface with a gastrointestinal bypass sleeve. The sleeve is preferably bonded on an internal luminal surface of the ring in some embodiments to advantageously prevent trauma to the esophageal wall.

Figure 2H:
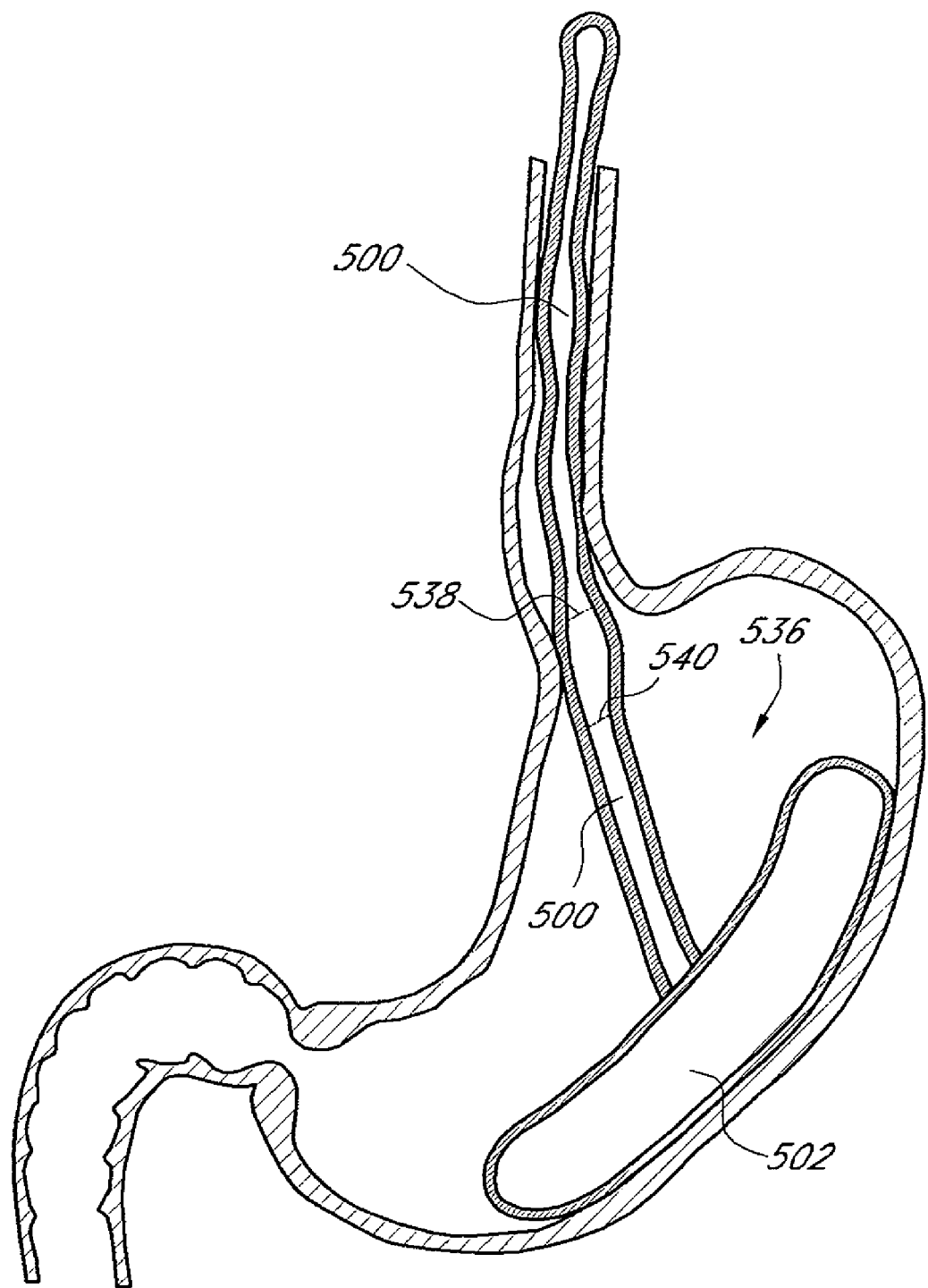
FIG. 2H schematically illustrates another embodiment of an intragastric support system with a proximal orientation element that includes a strut with a variable-diameter cross-section, according to one embodiment of the invention.
Figure 21:
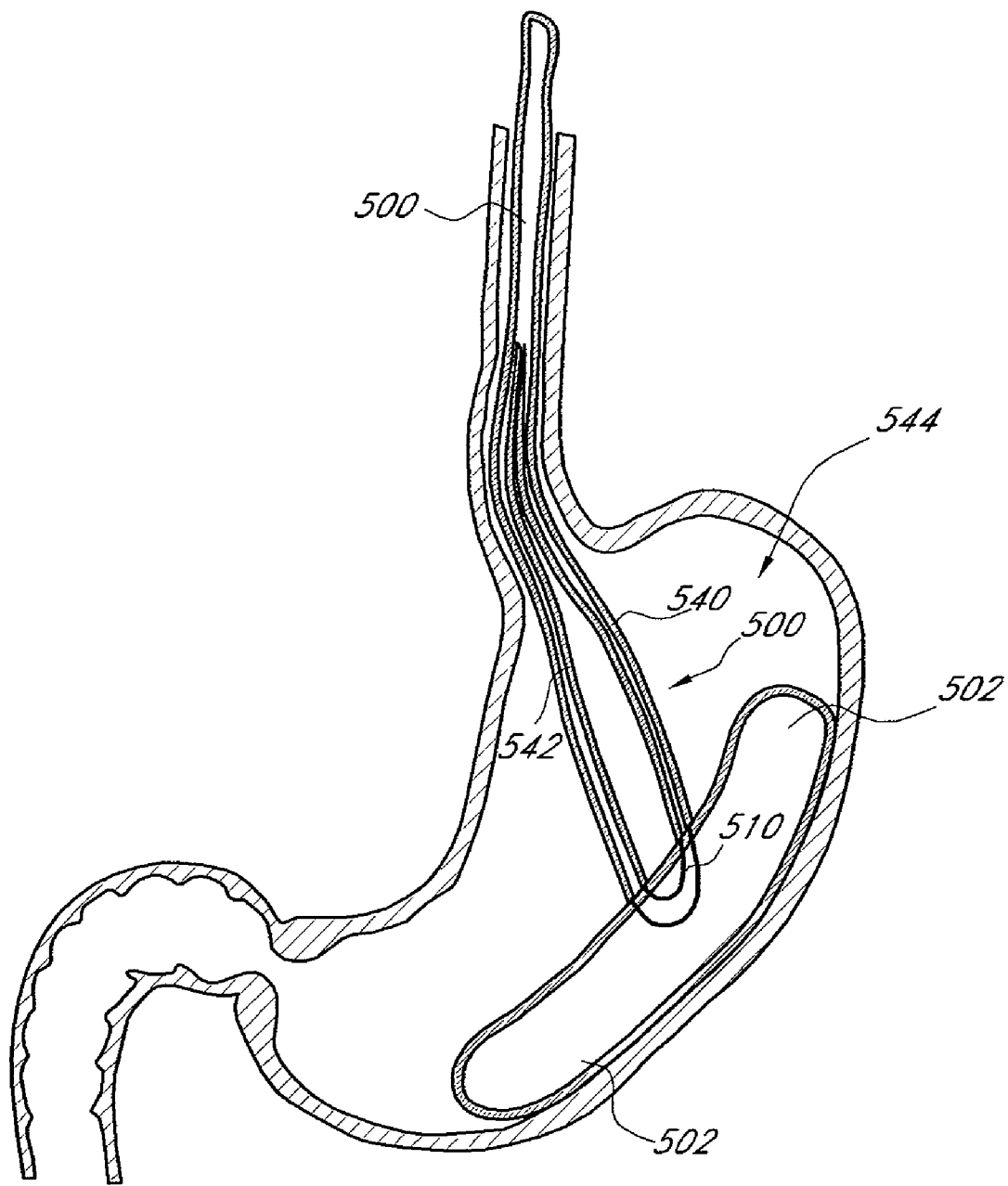
FIGS. 21A-D schematically illustrate a piecemeal method for delivering an intragastric support system, according to one embodiment of the invention.

FIG. 2H illustrates schematically another embodiment of an intragastric support system 536 with a proximal orientation element 500 that includes a strut member with a variable-diameter cross-section, which can advantageously allow the strut to have differing stiffness properties along its length and thus bending properties. In some embodiments, a proximal orientation element 500 includes a strut having a first point 538 with a cross-sectional diameter that is at least about 10%, 20%, 30%, 40%, 50%, 75%, 100%, 150%, 200%, or more greater than a cross-sectional diameter on a second point 540 of the strut.

FIG. 2I illustrates schematically an embodiment of an intragastric support system 544 including a proximal orientation element 500 with a plurality of strut members 540, 542, such as a bifurcated portion as shown, which can allow the proximal orientation element 500 to have differing bending properties depending on the desired clinical result.

Spiral Construct

Figure 2J:
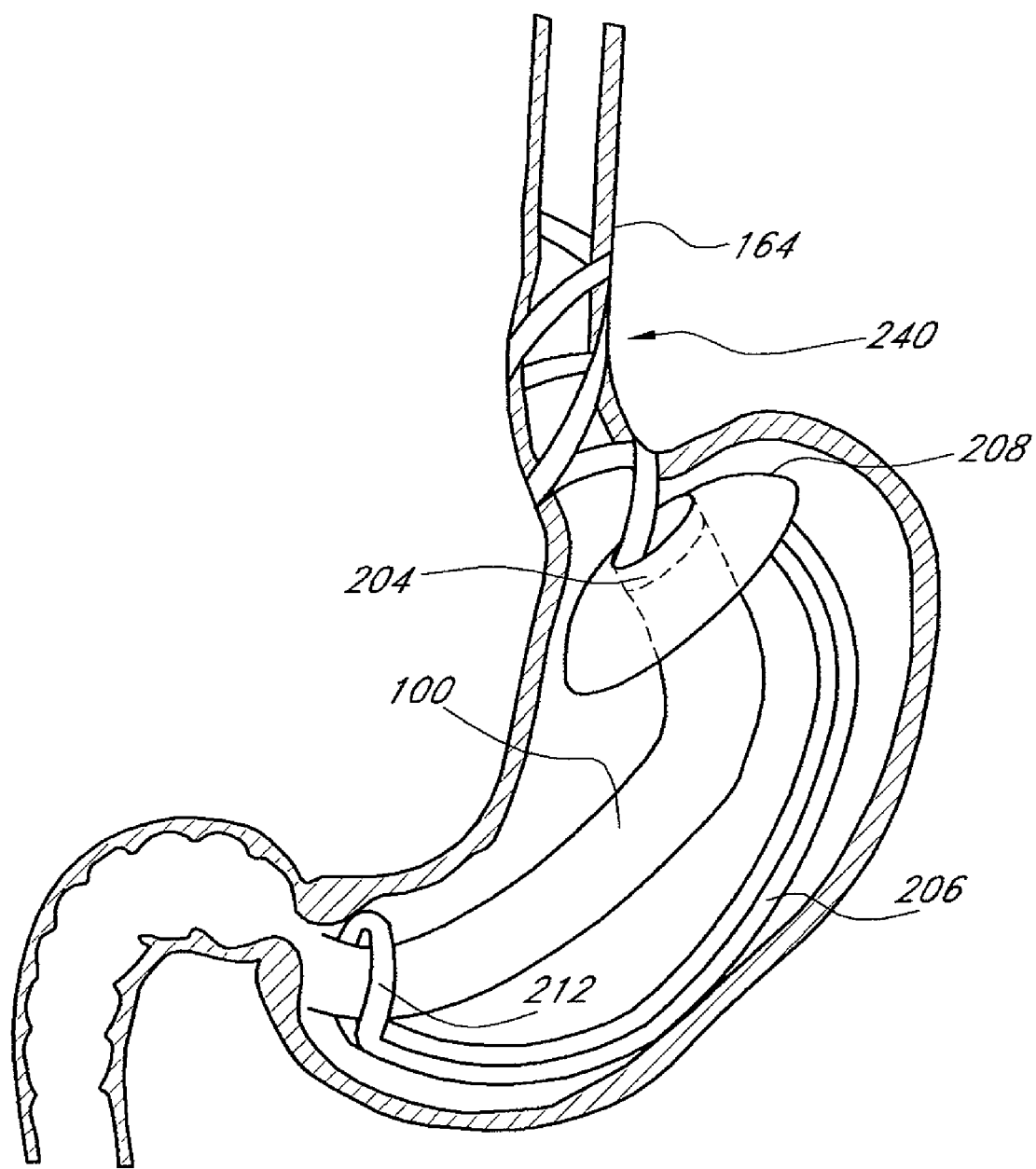
FIG. 2J illustrates an embodiment of an intragastric support system with a spiral proximal orientation element, according to one embodiment of the invention.

In some embodiments, the proximal orientation element 500 could be either linear or complex in shape, such as a spiral, or some combination of both. One embodiment of such a spiral proximal orientation element 240 is shown schematically in FIG. 2J. If the spring rate and radial force of the spiral form are configured such that the radial force is greater than the minimum required to maintain contact with the esophageal wall 164 and less than an amount that would cause damage to the tissue yet still have enough radial force to support the device, this can provide an alternative method of attachment. In this case, the cuff 204 would hang at the GEJ supported by the spiral connective element 240 without requiring any support distally.

In other embodiments, if the radial force of the spiral 240 does not have sufficient opposing force to the esophagus 164 to keep the cuff 204/sleeve 100 in place, the spiral construct 240 could facilitate orientation of the cuff 204/sleeve 100 with a distal support element 502 described elsewhere in the application. Alternatively, in other embodiments, the spiral 240 would not oppose the esophagus 164 at all, but rather be made of a relatively atraumatic material and float freely in the esophagus 164. Such a non-opposing spiral would maintain the position of the distal support element 502 such that food and liquid flowing through the esophagus 164 would enter the bypass sleeve 100 and bypass the stomach.

Once in the esophagus, the proximal orientation element could take the form of a spiral. Most preferably, in some embodiments, any spiral shape in the esophagus would be very compliant so as not to interfere with the peristaltic movement of the esophagus. The spiral element would then connect to the cuff. An advantage of having a spiral shape element may be that it could help keep the cuff in an orientation so that the plane of the opening of the cuff remains as perpendicular as possible to the flow of ingested material to minimize any leaks. This would enable most if not all of the contents passing through the esophagus to enter the sleeve and thereby bypass the stomach. In addition, the spiral shape of the connective element could have some minimal amount of radial force to help keep the cuff in contact with the walls of the GEJ to help minimize leaks. In some embodiments, the spiral element could be formed from an elastic material such as a polymer or other plastic or it could be formed from a super elastic material such as Nitinol. Preferably, the amount of radial force would be just enough to help keep the lumen of the cuff open and oppose the walls of the GEJ without causing any expansion of the GEJ or damage to the tissue. In other embodiments, the opening pressure would be less than that of the GEJ, such that when the GEJ was closed or flaccid, the opening of the sleeve would also be closed or flaccid. When the GEJ opens, the outward force would be such that the opening of the sleeve would then open.

The spiral proximal orientation element can preferably extend through at least about one or two and in some embodiments at least about 3, 4, 5, 6, 7, 8, 9, 10 complete revolutions, or more about the longitudinal axis of the esophagus.

In some embodiments, the proximal orientation element 500 includes an esophageal strut that can be an elongate member that is between about 10-50 cm, such as about 20-40 cm in length in some embodiments. The proximal orientation element 500, in some embodiments, can be made of a wire made of an appropriate material, such as steel or nitinol. The wire, or a proximal portion of the wire, such as at least about 60%, 70%, 80%, or more of the total length of the wire, may be tapered in some embodiments, such that the wire has a greater diameter proximally and a lesser diameter distally, such that the stiffness of the wire increases from a proximal to distal direction. In some embodiments, the wire can be covered by a biocompatible covering, such as silicone, with a durometer of between 30 a-50 a, such as about 40 a in some embodiments. The proximal end of the proximal orientation element may comprise a soft arcuate tip with a full radius to prevent trauma to the esophagus, and may be formed of the biocompatible covering extending beyond the proximal end of the wire.

Strips

Figure 2K:
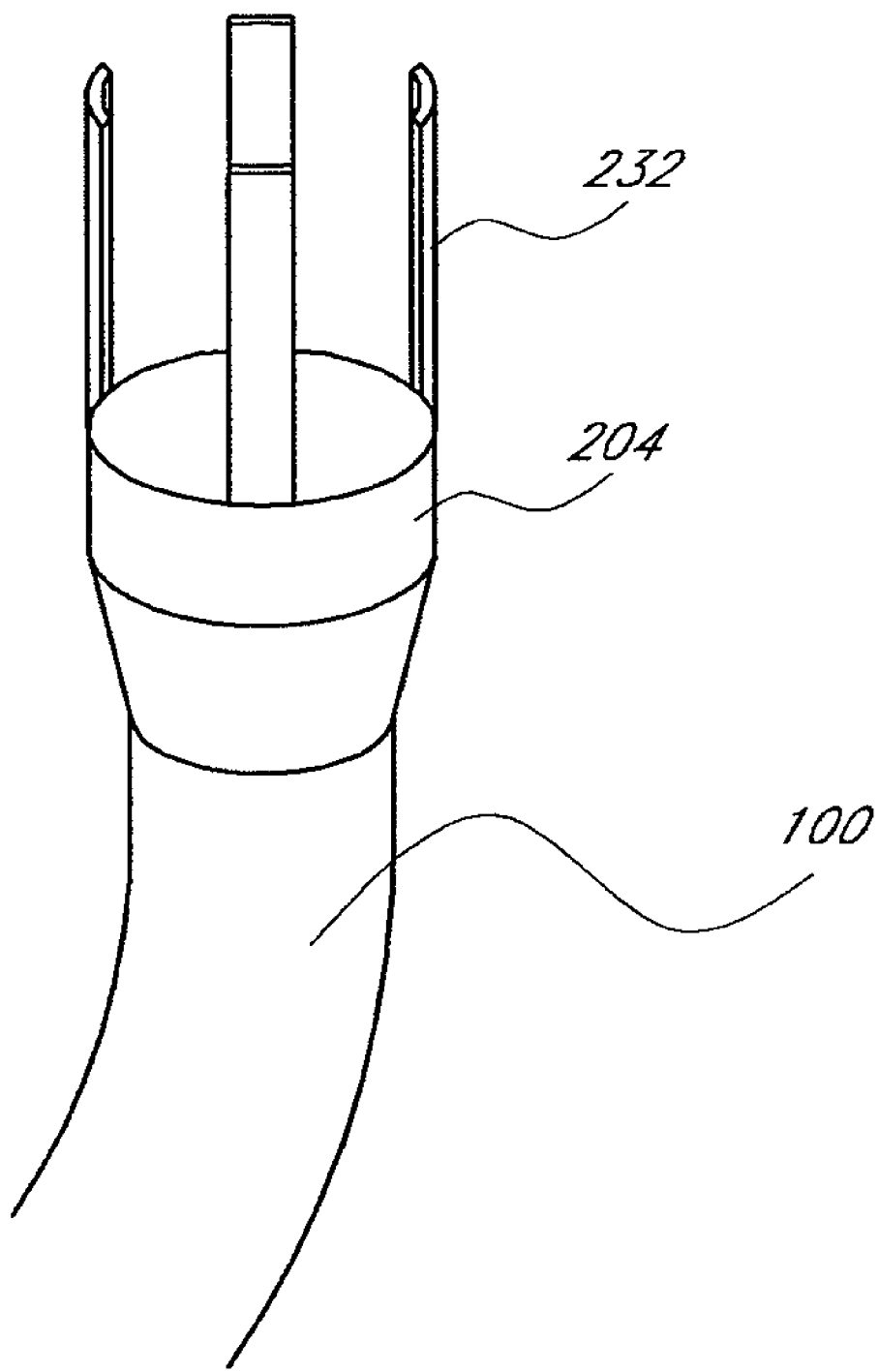
FIG. 2K illustrates an embodiment of a proximal orientation element with a plurality of strip elements attached to a cuff, according to one embodiment of the invention.

In order to promote tissue ingrowth/adherence of the proximal orientation element to the esophagus, strips of material attached to a cuff could be applied to the walls of the esophagus. There could be at least one, two, three, four, or more strips that can attach at the GEJ area to the cuff and extend cephalad (proximally) up the esophagus. FIG. 2K schematically illustrates an embodiment of these strips 232 attached to a cuff 204 and sleeve 100. Such strip 232 materials can include tissue graft materials, such as, for example, collagen, small intestinal submucosa, a tissue growth factor, or various tissue graft materials from Genzyme Corporation (Cambridge, Mass.). In some embodiments, these strips 232 could be of a woven or non-woven fiber or polymer or could be some form of tissue graft or a combination of these materials. These strips 232 may be held in place with adhesives or stitches or through tissue ingrowth or some combination of these methods. One possible adhesive could be fibrin glue, an example of which is the TISSEEL® product distributed by Baxter, PMMA or other polymeric glue. The adhesive could be selected such that it forms a long-term bond lasting at least a week, two weeks, a month, a year, or more, or it could be intended for shorter term use and lose much of its strength for no more than about a month, two weeks, one week, 3 days, 2 days, or even less. Cyanoacrylate is an example of a potential longer-term adhesive. The strips 232 may be intended to only be bonded with the adhesive, or alternatively could be designed to heal into the wall of the esophagus, or could be a substrate for tissue in-growth. The strips 232 could be applied to the walls of the esophagus with a balloon or other expandable device. While the strips 232 would not deliver substantial radial force to the esophagus they would allow the esophagus to remain compliant and not affect its movement substantially. The strips 232 could have a free end or the strips 232 may have another flexible member that connects the ends if this is determined to be beneficial to either attachment or deployment of the device.

Surface Preparation

In some embodiments, it may be beneficial to prepare the surface of the esophagus before applying any of the esophageal attachment devices described above. The goal of the surface preparation of the esophagus would be one or more of the following: (1) increase ability of an adhesive to bond; (2) accelerate the rate of tissue in growth or (3) alter the tissue layers to help provide a more durable attachment substrate. Possible non-limiting methods used to prepare the surface could include the delivery of any of: optical energy, such as a laser for example an Argon laser; RF energy; microwave energy; Argon plasma coagulation (APC), thermal energy; cryo energy; ultrasound, focused or unfocused; high or low pH materials; sclerosing agents, friction, or the like. The surface preparation could have the goal of damaging the mucosal layer or removing the mucosal layer completely to expose the submucosa.

There are devices described in the art to mechanically remove, such as by sucking in and then cutting off a layer of tissue, the mucosa of the esophagus in order to remove strips of mucosal tissue. These devices are described for the use of removing abnormal tissue that may be precancerous from the walls of the esophagus (e.g., Barrett's esophagus). In this indication, they could be used to prepare the inner surface of the esophagus for the attachment of devices described above. In some embodiments, the method could also entail removing the submucosa to expose the muscularis.

Alternatively, proximal orientation elements as described above could be used with a distal support element or as part of an element in complex intragastric support systems as described below.

Distal Support Element

Another component to provide support to an implanted device to help maintain position in a body lumen such as the GI tract is to provide support by maintaining a position in the GI tract, for example, the stomach. A simple example of this would be a pillar like device in the stomach that supports a cuff at the GEJ as shown in FIG. 25 of the Kagan '148 application. A rigid pillar is less preferred because of the amount of motility of the stomach and the dynamic nature of the environment. However, other elements could provide similar support. Similar to the device as described in U.S. Patent Publication No. 2006-0015125 to Swain et al., which is hereby incorporated by reference herein in its entirety, in one embodiment, disclosed is a dynamic-shaped element that if surrounding or supporting the sleeve could hold or help hold the sleeve in place at the GEJ. FIG. 1 of the Swain '125 publication incorporated by reference above illustrates a distal support element that could be used to help support the cuff/sleeve construct at the GEJ.

Referencing FIGS. 1C-1E of the present application, in some embodiments, the distal (e.g., intragastric) support element 502 illustrated here includes a flexible dome-shaped element 208 designed to reside in the upper portion of the stomach, a support structure 210 that may be arcuate-shaped in some embodiments that connects the flexible dome 208 to the pyloric support element 212.

FIGS. 3A-3F depict various views of one embodiment of a dome-shaped component 208 of a distal support element 502 with an aperture 209 that can be configured to receive a bypass sleeve 100 (not shown), according to one embodiment of the invention. In some embodiments, the dome 208 has a diameter of between about 1-10 inches, such as between about 2-6 inches, 2-4 inches, or 2.5-3.5 inches at its widest point, and between about 0.5-5 inches, 0.5-3 inches, or 0.5-2 inches as the diameter of aperture 209. The flexible dome 208 could be made from silicone, latex, polyurethane or any other material that is sufficiently resistant to gastric acid, biocompatible, and will remain flexible in the stomach. Other possible materials the dome 208 could be made of, for example, include Nitinol (that may be woven Nitinol), plastics, and polymers. Other possible materials can be selected according to the desired clinical indication. The dome 208 illustrated is convex, however it could have concave portions either to act as a funnel to direct food into the bypass sleeve or to help accommodate natural structures in the stomach to maintain its location. Furthermore, the dome 208 need not be round, and may have other arcuate or even non-arcuate shapes. The dome 208 can also have one-way check-valves that would allow air or fluid to flow up the esophagus when there is sufficient pressure, e.g., during vomiting. In some embodiments, the dome 208 could also incorporate other funnel shaped structures or channels to direct food that passes the GEJ but does not get forced into the cuff/sleeve to once again get directed back into the sleeve.

The pyloric support element 212 of the distal support element 502 as shown, for example, in FIGS. 1C-1E can be the integral distal part of, or attached to the arcuate support structure 206 in other embodiments. The configuration of the pyloric support element 212 most preferably prevents the distal support element 502 from migrating through the pylorus. In some embodiments, the device can be deployed in a collapsed state and then expanded in the stomach. Alternatively, the distal end (e.g., the pyloric support element) could be enlarged after passing through the pylorus and provide support by anchoring against the wall of the duodenal bulge.

Various methods known in the art could be used to create a distal end (e.g., pyloric support component 212) that expands from a first configuration with a smaller cross-sectional area to a second configuration with a larger cross sectional area to resist passage of the device through the GI tract. The distal end 212 could be made of a shape memory metal or polymer that when delivered is in a collapsed state, and when in the selected region of the GI tract, such as the stomach, expands to a diameter greater than could pass through the selected region of the GI tract. If the arcuate support element 206 is a rod-like structure that is bent back on itself with the bend at the pylorus, the pyloric element 212 could be preformed into a hoop shape at the bend as shown that is biased to compress for delivery and expand and rotate to form a loop upon placement in the stomach. In other embodiments, multiple stent structures could accomplish this; Malecot-type or other devices having mechanically enlargeable cross sections or surface area could also be used. Inflatable elements or injectable bags of material optionally with a hardenable polymer could also provide the same interference fit with the lumen. In a preferred embodiment, the pyloric support element 212 has a central lumen through which the sleeve can fit therethrough to allow free flow of food and other contents through the system without being pinched between the pyloric element and the wall of the stomach or pylorus. Alternatively, it can be desirable in some cases to have the sleeve pinched between the pyloric support element 212 and the stomach wall to form a restrictive element to slow up the passage of food. Some examples of pyloric support elements 212 have been described, for example, in the Kagan '148 application, previously incorporated by reference in its entirety.

The arcuate support component 206 of a distal support element 502 is preferably configured to hold in place the proximal end of the cuff 204/sleeve 100 and/or flexible dome 208. To form a support structure, the distal support element 502 can be more rigid in some aspects, however still have flexibility and compliance in some motion directions to accommodate the natural motion of the stomach, allowing the stomach to act on the sleeve and propel food through it The cuff 204 or cuff 204/sleeve 100 could have a columnar strength or it could have one or more spines to provide vertical support. The arcuate support element 206 preferably provides support from the proximal end of the cuff and/or sleeve to its base of support either against the greater curve of the stomach or against some aspect of the pylorus or preferably some combination of both in some embodiments. In one embodiment the arcuate support element 206 is banana shaped with dimensions that tend to match, or are proportional to, the greater curve of the stomach. The arcuate support element 206 could have an arc angle from the attachment at the GEJ to the pylorus depending on the particular stomach configuration of the patient. In some embodiments, the arc angle is at least about 45, 60, 75, 90, 105, 120, 135, 150, 165, 180, 195, 210 degrees, or more. The device can be made of a shape memory metal, plastic, or other biocompatible material and most preferably would have a hydrophilic or lubricious coating. The pyloric support element can 212 be on the distal end of the banana-shaped arcuate support 206. Alternatively, the support device can be expanded by inflation with, for example, a liquid, a gas, a liquid that becomes a solid, or a foam. In one embodiment, the banana-shaped arcuate support element 206 can be made of two telescoping pieces with an internal spring much like a banana shaped shock absorber. This would allow for some compression along the length of the device to accommodate contractions of the stomach. The arc of the banana would provide predisposition to flex along the length of the arc. It could be more compliant in the approximate direction defined by an axis drawn from the esophagus to the pylorus than in a direction perpendicular to that axis or vice versa. In some embodiments, the device could be made from a shape memory metal or polymer that has a preferred shape when at body temperature but is cooled before implantation to make it very flexible for delivery through an endoscope. The flexibility allows for nearly free motion of the stomach wall, and the device would be low enough in profile to not significantly interfere with the stomach transferring its motion to the sleeve and thus the contents thereof.

In some embodiments with separate dome support components and pyloric support components of a distal support element, the arcuate support structure between the dome support element and the pyloric support element could be actuated. In other words, the arc could be expanded or contracted with a motor or some control means that expand or contract the stomach to induce satiety or another desired therapeutic purpose. This may be manually controlled via a transmitter, or automated, such as by a sensing mechanism.

The device design of the distal support element most preferably prevents it from migrating through the pylorus as noted above, in some embodiments. The entire device can be deployed in a collapsed state and then expanded in the stomach. Optimally, it would be collapsed enough so it can be delivered perorally, such as via endoscopic assistance.

Figure 4:
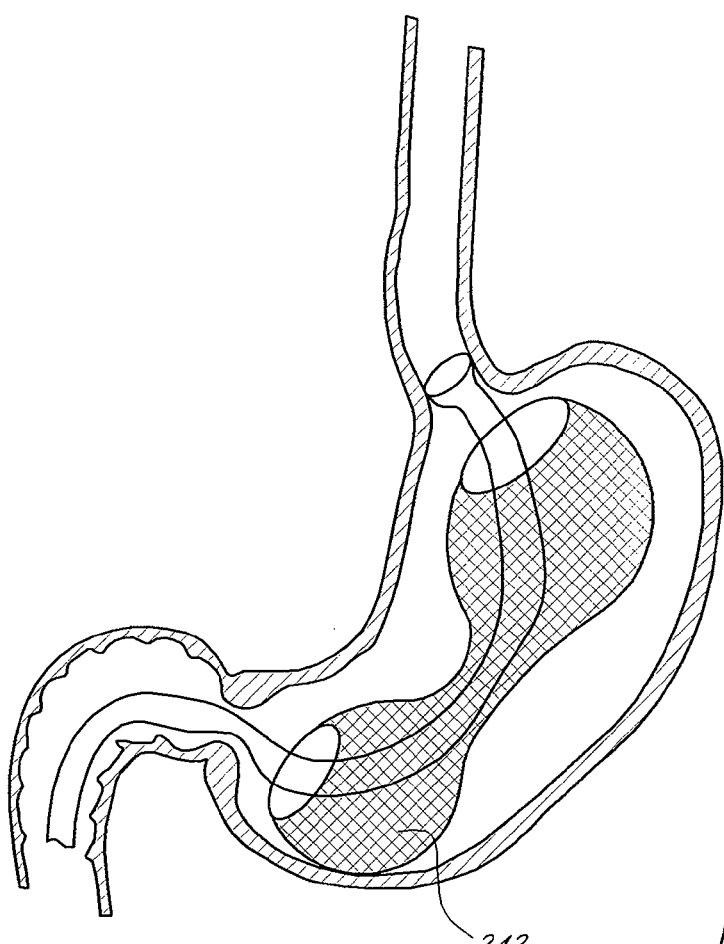
FIG. 4 illustrates an intragastric support system that includes a braided distal support structure, according to one embodiment of the invention.

In another embodiment, as shown in FIG. 4, a distal support element 242 could be a non-arcuate shape, for example, a woven basket as illustrated. Nitinol, Elgiloy, Spring Steel or other wire or ribbon may be used. The woven material may be coated with a material such as silicone, polyurethane or other polymer, PTFE, ePTFE, Dacron, or other material depending on the desired clinical result. In other embodiments, the distal support element could be helical shaped, or have arms that would expand to apply force against the walls of the stomach. In other embodiments, examples of devices of this configuration that could be modified to be used as distal support elements are those used to occlude left atrial appendages, such as those manufactured by Atritech, or devices used to close patent foramen ovales, such as devices made by Velocimed and AGA. Scaling up of such devices to accommodate the dimensions of the stomach to serve as a distal support can be performed depending on the desired clinical result.

Figure 5:
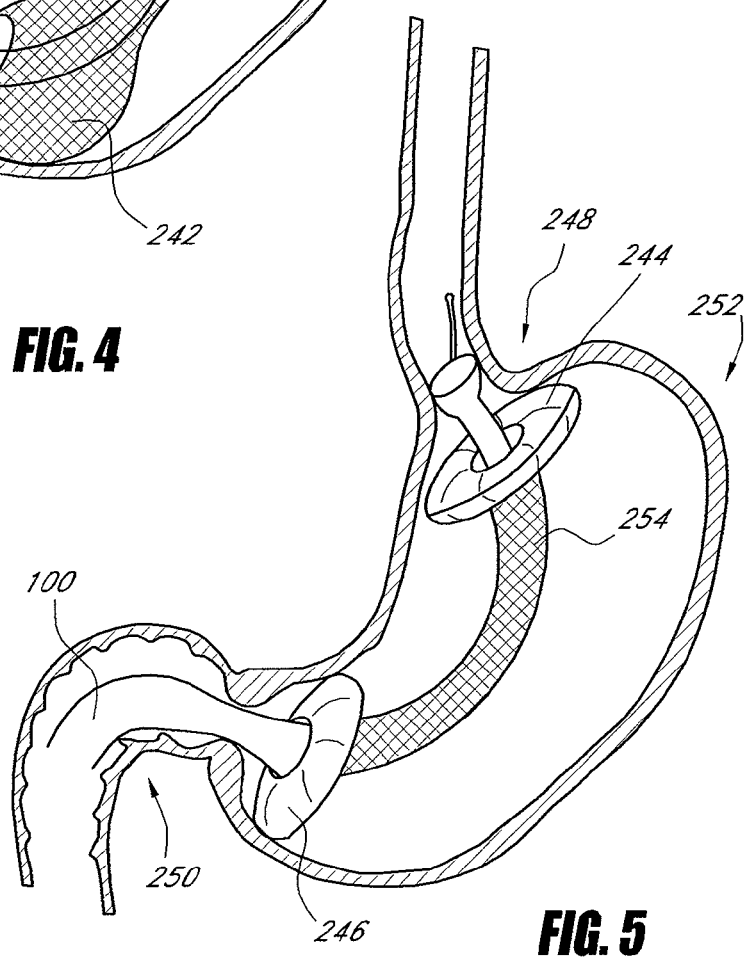
FIG. 5 shows an intragastric support system with a distal support element having proximal and distal toroidal supports such as balloons, according to one embodiment of the invention.

FIG. 5 illustrates an embodiment 252 of a distal support element that includes a plurality of toroidal balloons 244,246, on the proximal 248 and distal 250 ends. The device 252 also can include a braided nitinol structure 254 over at least a portion of a sleeve 100 configured to pass between the balloons 244, 246. The device 252 may be covered or coated with a suitable material as noted above. The arcuate support element and a stiffening element of the sleeve could be the same structure. In one such embodiment, the portion of the stiffening element of the sleeve distal to the pylorus can be floppier or more flexible. The proximal segment preferably has an arcuate shape set into the material so once deployed within the sleeve the sleeve takes a curve following the greater curve of the stomach.

Figure 6A:
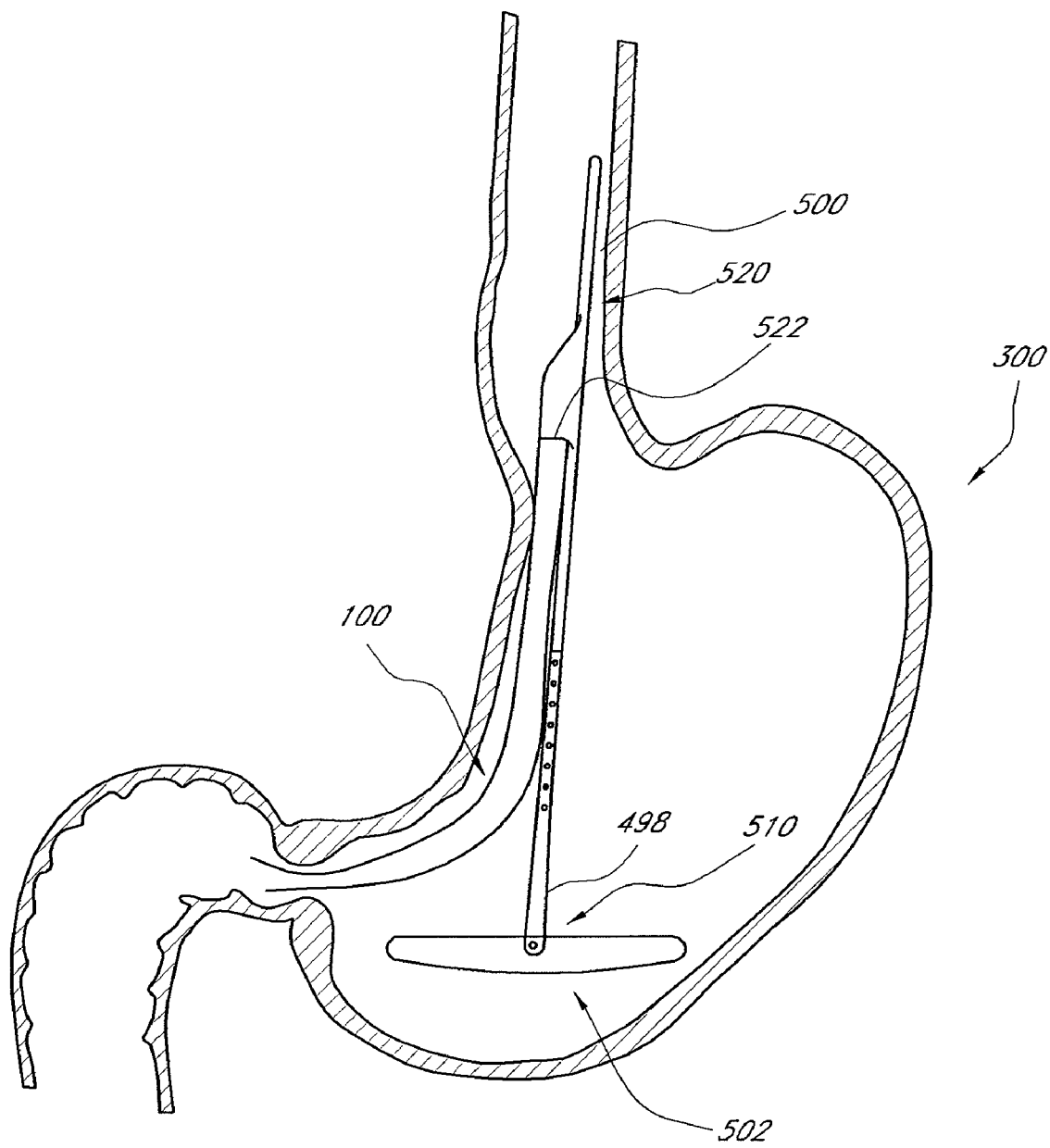
FIGS. 6A-6B illustrates an intragastric support system with a proximal orientation element that includes an esophageal strut element pivotably attached to a distal support element, according to one embodiment of the invention.

FIG. 6A illustrates an intragastric support system 300 with a proximal orientation element 500 having a tapered esophageal ring element 520 as shown in FIG. 2G and described above. The distal end 498 of the proximal orientation element 500 is hingably connected, such as via a pivot point 510, to a distal support element 502 at the midpoint of the distal support element 502 as shown. In other embodiments, the hinge/pivot joint 510 may be offset from the midpoint, or at an end of the distal support element 502. Also shown is a gastrointestinal bypass sleeve 100 operably connected to the intragastric support system 300 at the distal end 522 of the ring element 520 of the proximal orientation element 500. Not to be limited by theory, the hingably connected distal support element 502 can be advantageous in several ways. It can allow the intragastric support system 300 to adjust to gastric motility and stomachs of various sizes. Furthermore, bending stresses against the esophagus can be minimized as the pivot element 510 can allow the esophageal post portion 500 to be maintained relatively coaxially with the walls of the esophagus. Moreover, such embodiments can prevent the esophageal post 500 from collapsing into the stomach, and as such a dome-shaped element would not be required. Also, the hingably connected distal support element 502 can provide distributed support for the proximal orientation element 500, along the more muscular region of the stomach, avoiding the more elastic fundus region which may provide less predictable support.

Figure 6B:
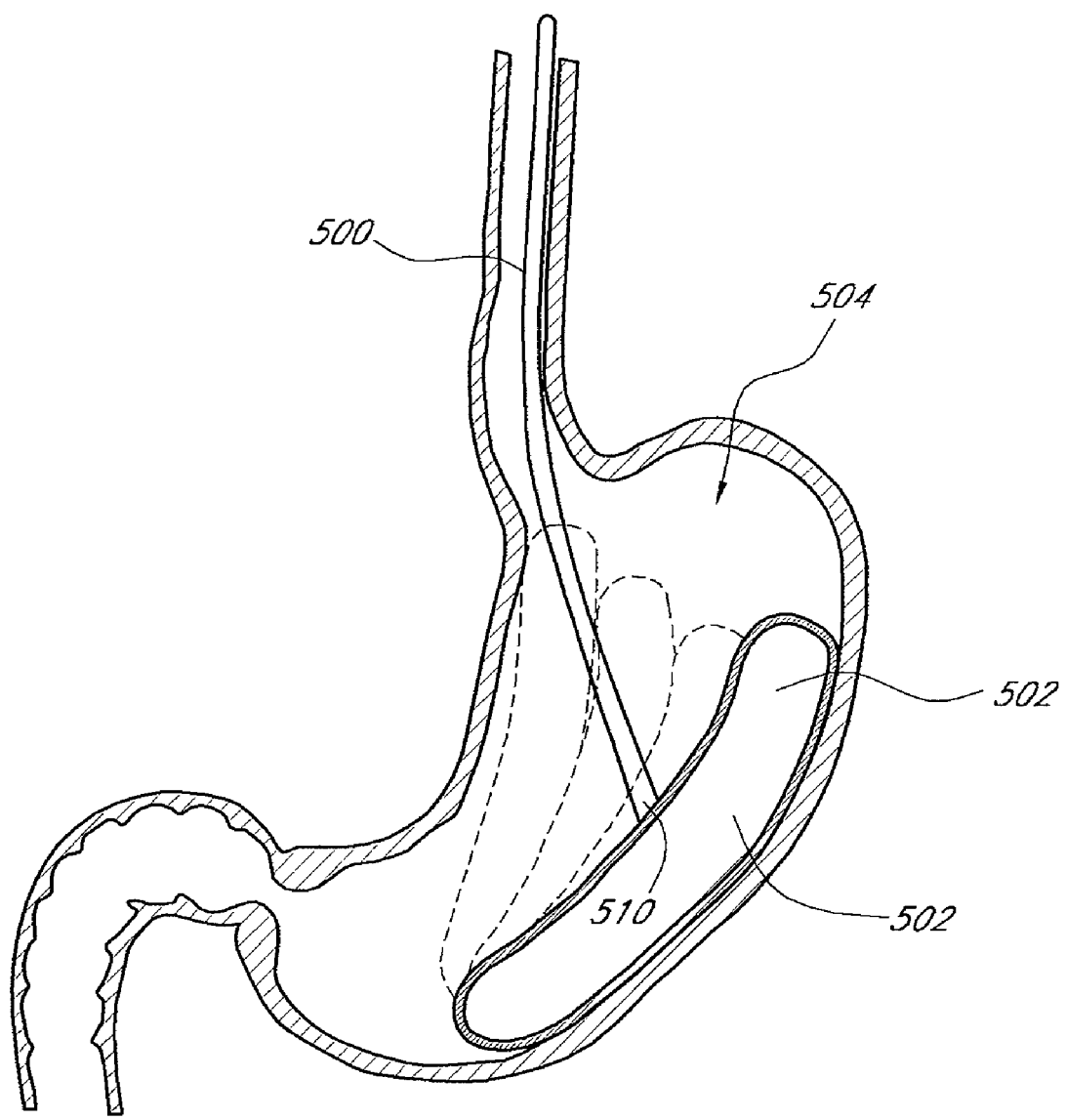

Similar to the embodiment described in FIG. 6A, FIG. 6B schematically illustrates that the distal support element 502 can be movable, such as pivotably movable with respect to the proximal orientation element 500 (as illustrated schematically in phantom) at a joint 510 as shown. The joint 510 is preferably completely or at least substantially smooth at its external surface, and recessed or potted in some embodiments. The joint 510 can be, for example, a bidirectional joint, such as a hinge-type joint, or a multidirectional joint, such as a ball-and-socket type joint. The joint 510 can be configured to, in some embodiments: (1) freely pivot, (2) pivot within a particular range of motion, such as no more than about 330, 300, 270, 240, 210, 180, 150 degrees, or less in some embodiments, and/or (3) be locked in a fixed position. For example, in some embodiments, activating or deactivating a locking control (not shown) will allow the joint 510 to change mode from being locked in a fixed position to pivot within a range of motion.

Figure 7C:
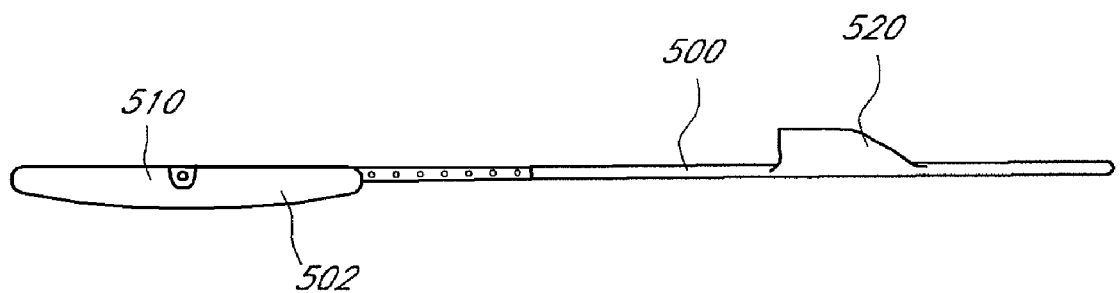
FIG. 7C illustrates an intragastric support system where the long axis of the proximal orientation element is coaxial with the long axis of the distal support element, according to one embodiment of the invention.

The distal support element 502, and/or at least a portion of the proximal orientation element 500, shown in FIG. 7A may be made of any appropriate biocompatible material, such as a metal, e.g., polished titanium in some embodiments. The distal support element 502 may also include a coating as described elsewhere in the application. The intragastric support 502 may have an arcuate shape to contour with a wall of the stomach, or other shapes depending on the desired clinical result. FIG. 7B is another view of the device shown in FIG. 6. FIG. 7B illustrates the intragastric support system 300 of FIG. 6, wherein the distal support element 502 is moved from the configuration shown in FIG. 7C such that the long axis of the distal support element 502 as shown in FIG. 7C (a "straight" configuration) is at least substantially parallel to, and/or coaxial with the long axis of the proximal orientation element 500. This lower-profile configuration may be advantageous for endoscopic delivery. In some embodiments, the system can be configured to be deployed within no more than about a 30 mm, 28 mm, 24 mm, 22 mm, 20 mm, 18 mm, 16 mm, or less inside diameter esophagus.

The distal support element 502 is preferably atraumatic and smooth to prevent damage to the stomach mucosa as well as associated structures. In some embodiments, the distal support element 502 is configured to conform to the anatomy of the stomach, such as having a portion configured to conform to the greater curvature of the stomach as shown. The distal support element 502 may be made of any appropriate material, and may be made of titanium in some embodiments.

Figure 7D:
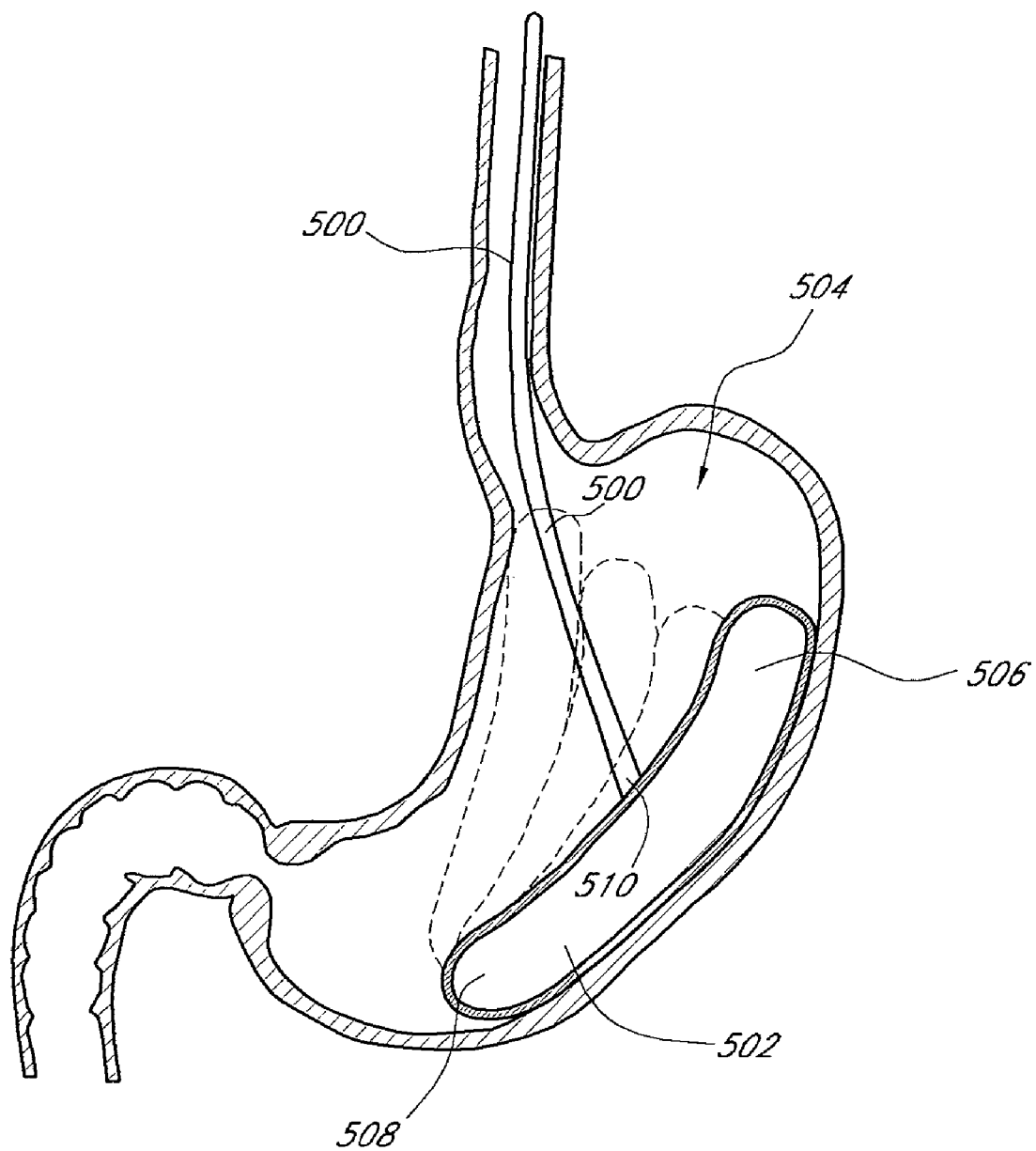
FIG. 7D schematically illustrates an intragastric support system with a radiused pivoting distal support element, according to one embodiment of the invention.

In some embodiments, as shown schematically in FIG. 7D, the distal support element 502 is radiused on all sides, with a preferably arcuate proximal end 506 ("heel portion") and distal end 508 ("toe portion") and can be between about 60-180 mm in length, such as between about 90-150 mm in length, or about 100-130 mm in length in some embodiments. The distal support element 502 can have a height of between about 5-40 mm, such as between about 10-30 mm, or between about 15-25 mm in some embodiments. The distal support element 502 can have a width of between about 5-35 mm, 5-25 mm, or 10-20 mm in some embodiments. In some embodiments, the length of the distal support element 502 is no more than about 70%, 60%, 50%, 40%, 30%, 20%, 10%, or less of the length of the length of the proximal orientation element 500.

Figure 7E:
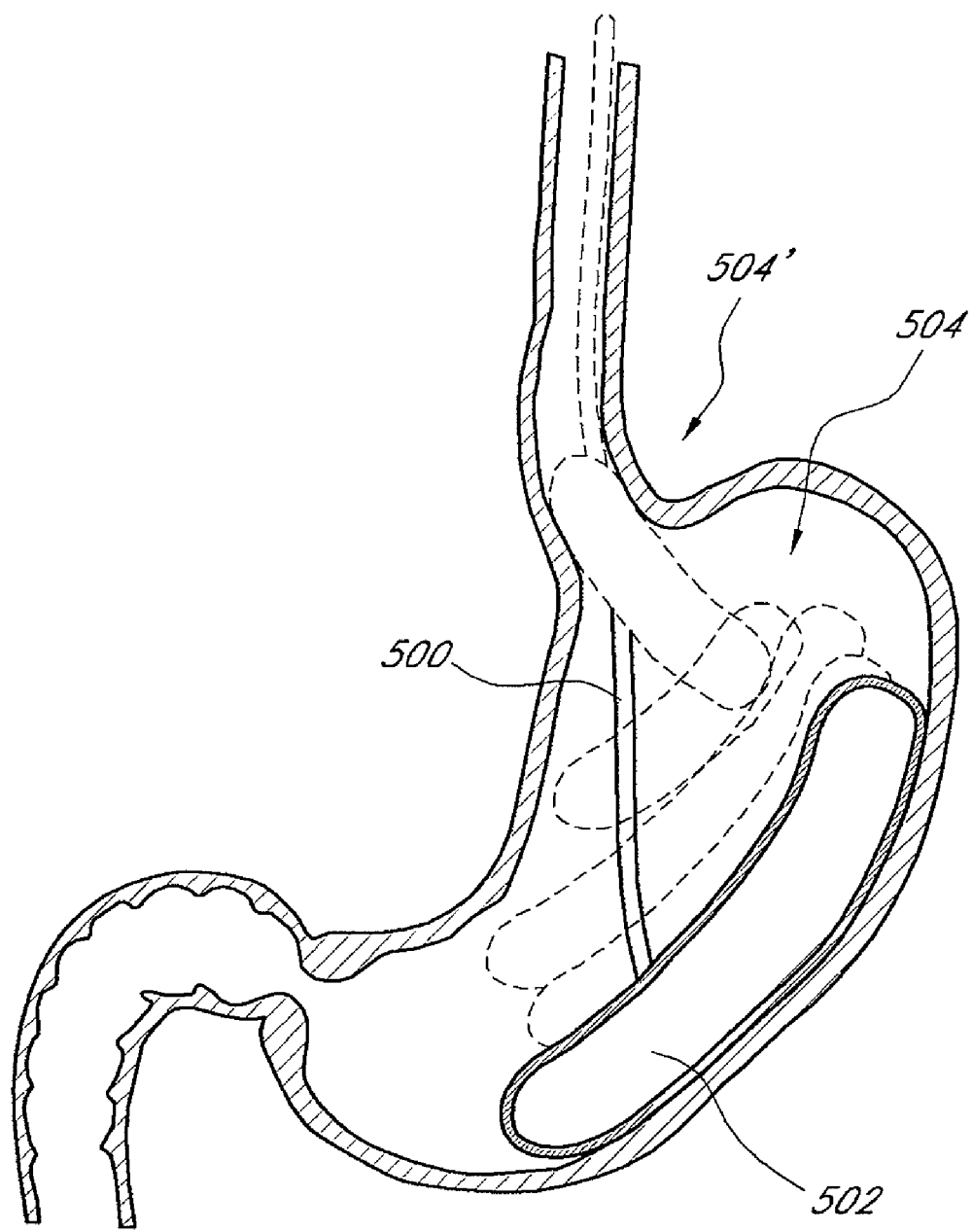
FIG. 7E schematically illustrates an intragastric support system that can be delivered endoscopically in a first reduced configuration and then expanded in a second expanded configuration, according to one embodiment of the invention.

The device 504 or a portion of the device, such as the distal support element 502, may be inserted into a body lumen in a first, reduced configuration for delivery 504' (shown in phantom) and then transformed into a second, enlarged configuration 504 as shown in FIG. 7E. Expansion of the device can be achieved by, for example, filling of the device with a filler material (as described below in connection with FIG. 7F), or a shape memory material. In some embodiments, the device can be transformed back into a reduced configuration if the device is removed from the body.

Figure 7F:
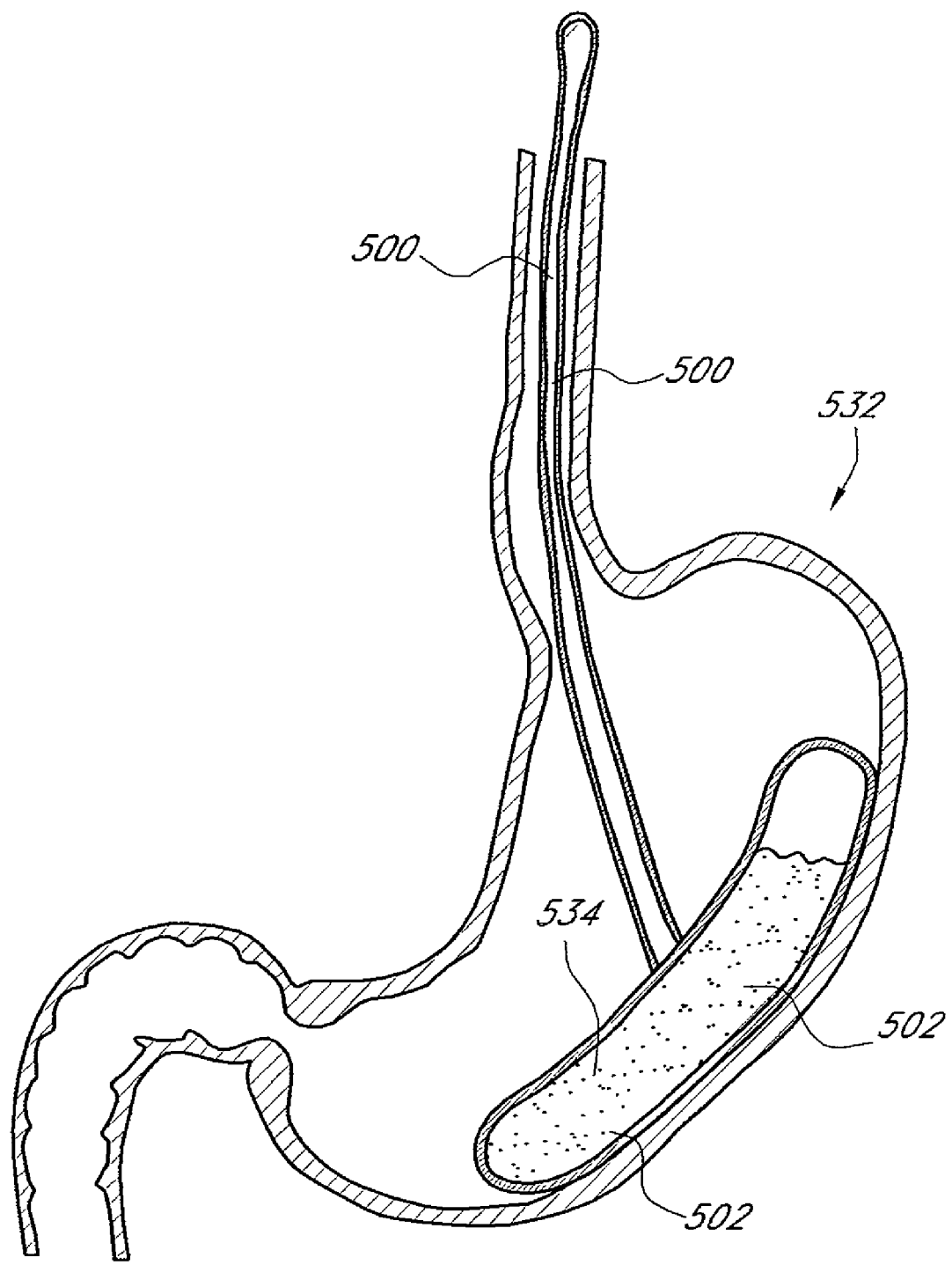
FIG. 7F schematically illustrates an intragastric support system with an expandable distal support element, according to one embodiment of the invention.

FIG. 7F schematically illustrates an embodiment 532 where the distal support element 502 is configured to be fillable with a filler material 534, such as a solid, liquid, or gas depending on the desired clinical result. However, the distal support element may only be partially fillable or solid (non-fillable) in some embodiments. In some embodiments, the distal support element may be made of a rigid, semi-rigid, or rigid transitioning to a semi-rigid material. In some embodiments, the distal support element can be configured to be filled with, for example, between about 1-10,000 cc, between about 10-5000 cc, 100-3000 cc, 200-1000 cc, or between about 200-500 cc of a filler in some embodiments.

Figure 7G:
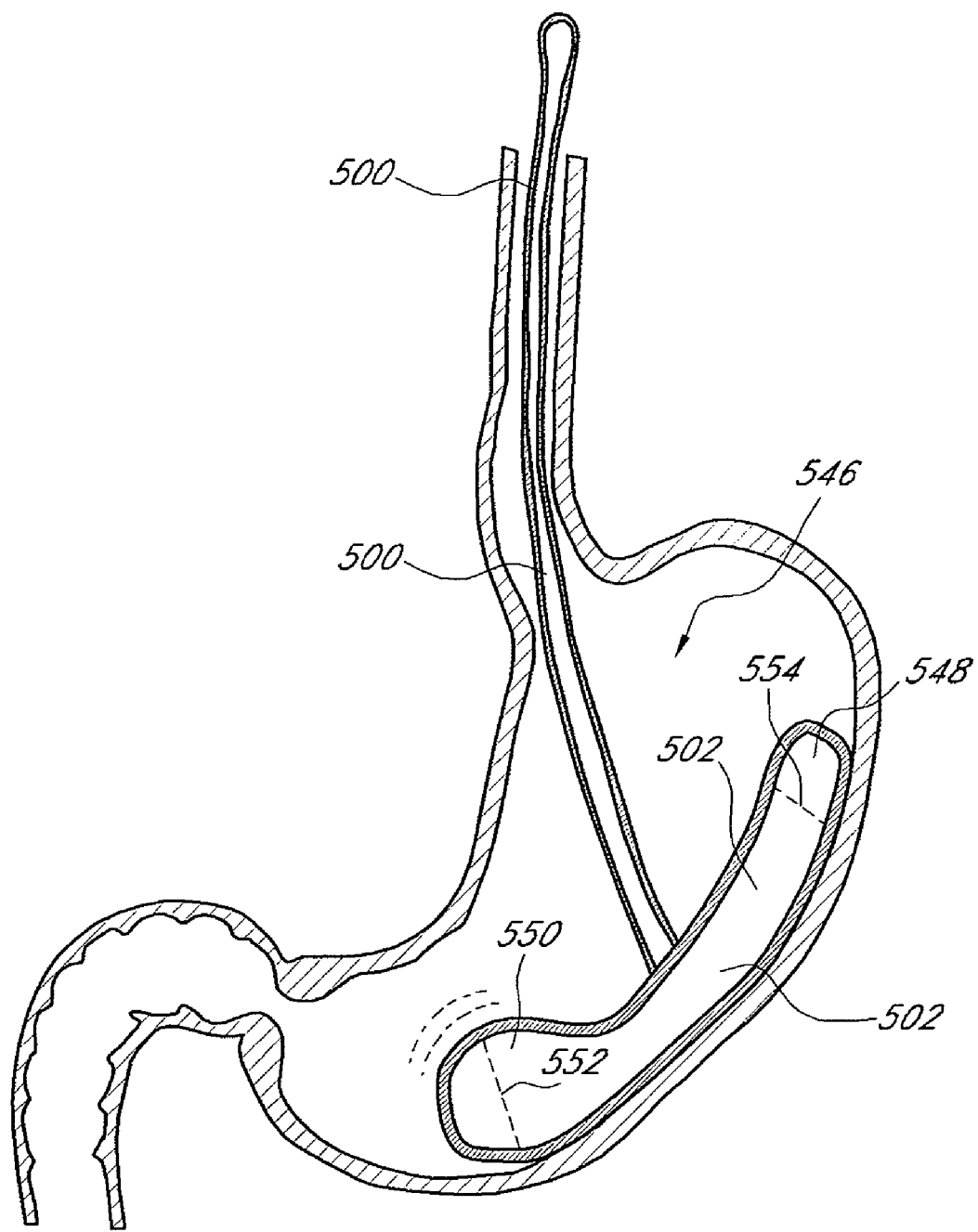
FIG. 7G schematically illustrates an intragastric support system with a distal support element with an enlarged distal end, according to one embodiment of the invention.

FIG. 7G illustrates an embodiment of an intragastric support system 546 with a distal support element 502 with an enlarged "toe portion" or distal end 550. The enlarged toe portion 550 may have a height 552, for example, that is at least about 5%, 10%, 15%, 20%, 25%, 30%, 40%, 50% or more greater than a height 554 of the proximal end 548 of the distal support element 502, in some embodiments. The elongated distal end portion 550 can advantageously help prevent the system 546 from migrating distally through the pylorus into the intestine. In some embodiments, the enlarged toe portion has a dimension greater than that of the pylorus, such as at least about 3 cm, 4 cm, 5 cm, 6 cm, or more.

Figure 7H:
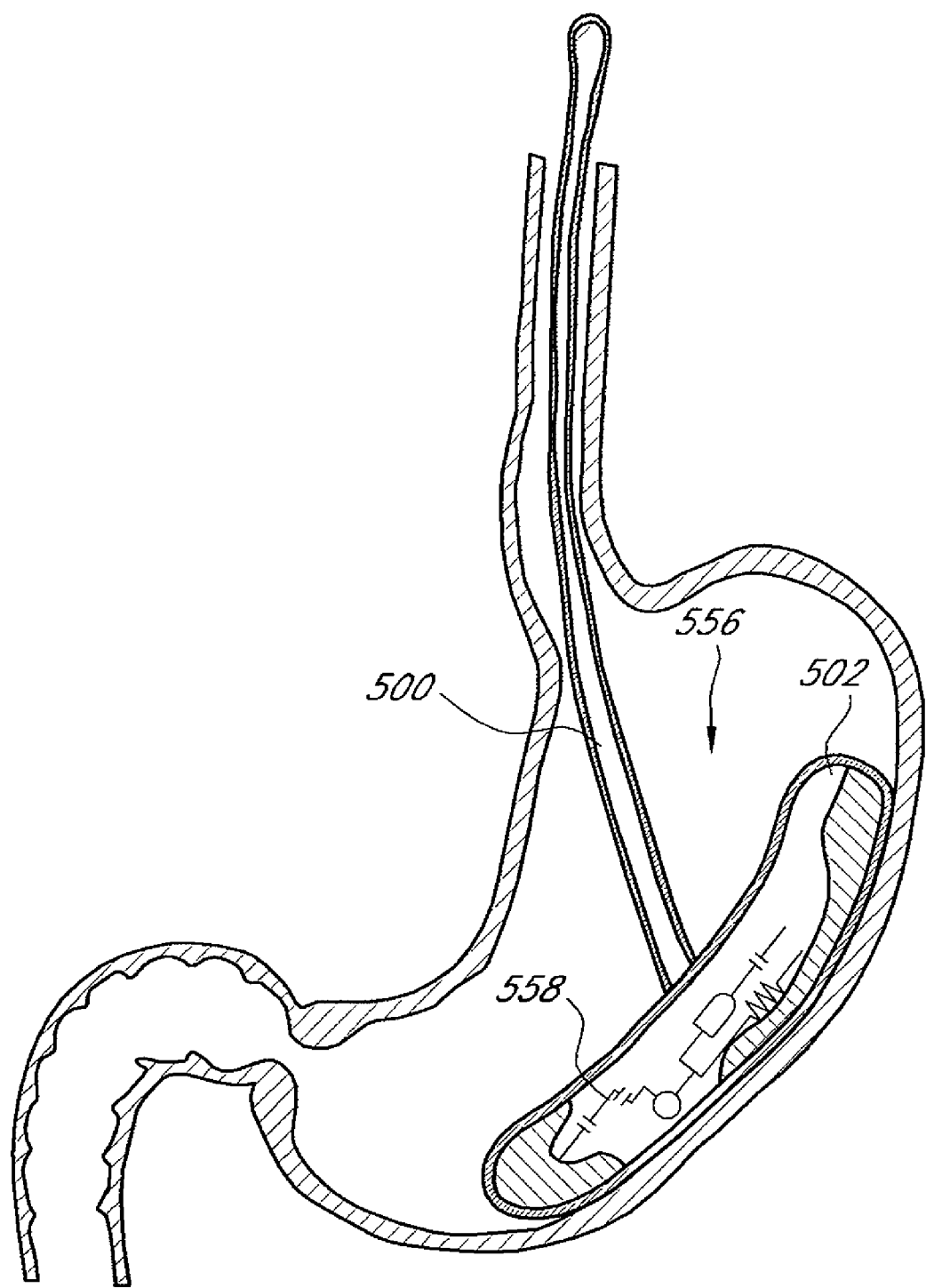
FIG. 7H schematically illustrates an intragastric support system with a distal support element that includes electronics, according to one embodiment of the invention.

FIG. 7H schematically illustrates an embodiment of a gastrointestinal support system 556 in which the distal support element 502 and/or proximal orientation element 500 could include electronics 558, for example, a pressure or volume sensor that can detect the presence of food in the esophagus or stomach, or monitor the pressure of the lower esophageal sphincter to prevent reflux. The distal support element 502 and/or proximal orientation element 500 could also include a drug reservoir, as described in greater detail elsewhere herein.

In some embodiments, the distal support element can be made of a wire such as stainless steel, nitinol, or other appropriate material as shown in FIGS. 8A-8C and can be made having a shape similar to that of the greater curve of the stomach, as shown in FIG. 8D. The distal end 258 of the wire 256 preferably forms a hoop 258 that is larger than can fit through the pylorus. The wire 256 is preferably coated with a hydrophilic coating that is acid resistant, such as, e.g., the HARMONY® Advanced Hydrophilic Coating from SurModics (Eden Prairie, Minn.). In some embodiments, the wire has a total length of between about 1-36 inches, such as between about 6 to 24 inches in some embodiments. In some embodiments, the wire 256 has a diameter of between about 0.001-020 inches, such as between about 0.020 and 0.080 inches. In some embodiments, the hoop portion has a radius of between about 0.1-2 inches, such as between about 0.2-1 inch, or 0.3-0.8 inches in some embodiments. In certain embodiments, there is a gap 259 between segments of the wire that is approximately 0.03-0.5 inches, 0.05-0.2 inches, or about 0.125 inches in some embodiments.

System Embodiments

Hybrid Attachment System

In some embodiments, the entire intragastric support system could be a combination of non-transmural attachment elements each designed to share the load of the device and one or more transmural attachment points. Disclosed below is one embodiment of a potential hybrid attachment system. Note the preferred attachment system may include any combination or subcombination of elements as described below.

The proximal orientation element, in one embodiment, is made out of nitinol coated with a hydrophilic coating with a soft tip on the free end. In some embodiments, the cuff would preferably be disposed within a funnel shaped opening in the top of a silicone dome as described above. In one embodiment, the dome preferably resides on top of a banana shaped support element that can be made of nitinol wire and has a similar shape as the greater curve of the stomach. The distal end of the nitinol wire preferably forms a hoop that is larger than can fit through the pylorus. One embodiment and dimensions of one preferred nitinol wire that may be part of a distal support element is shown in FIGS. 8A-8D and described above. The nitinol is preferably coated with a hydrophilic coating that is acid resistant, such as the HARMONY® Advanced Hydrophilic Coating from SurModics (Eden Prairie, Minn.). The sleeve is attached to the cuff and is configured to pass through the pylorus through the loop of the pyloric support element. The entire structure is designed to allow the stomach to collapse around it and transfer normal stomach forces and movement to the sleeve element.

In some embodiments, such as with the hybrid attachment system described above, in addition to the proximal orientation element and distal support element, one or more transmural anchors could optionally be placed through the cuff, silicone dome, cuff loops, or other appropriate structure to help provide additional fixation. Because of the additional orientation from the proximal orientation element and distal support elements, fewer anchors may be needed than have been previously disclosed in other applications referenced above and incorporated by reference. In one embodiment, no more than about 6, 5, 4, 3, 2, or 1 anchors would need to be placed. The anchors could be placed in areas of the GEJ where the strength of the attachment points could be optimized and at the same time the risk to adjacent structures could be minimized. For example, there could be three anchors placed along a 180° arc of the GEJ on the side of the lesser curve if this was known to be farther away from any critical adjacent structures and have greater anchor strength than the greater curve. Note that this is a non-limiting example only and it may be preferred to place the anchors along the greater curve of the stomach. In some embodiments, the anchors could have transverse elements that preferably have a length that is greater than a thickness of the stomach wall. For example, the length of the transverse elements could be at least about 150%, 200%, 250%, 300%, or more of the thickness of the stomach wall such that the transverse element functions as a tether assisting the post in maintaining the position of the intragastric support and/or sleeve such that alignment between the esophagus and sleeve is maintained.

In one embodiment of the above, the system could be attached with the following components: a proximal orientation element attached to the greater curve side of the cuff or distal support element; 2-4 transmural t-tags placed around the lesser curve of the cuff; a sleeve with a stiffening element; and an arcuate support portion with a pyloric support portion of the distal support element.

Sleeve with Support Lumen

Figures 9A, 9B:
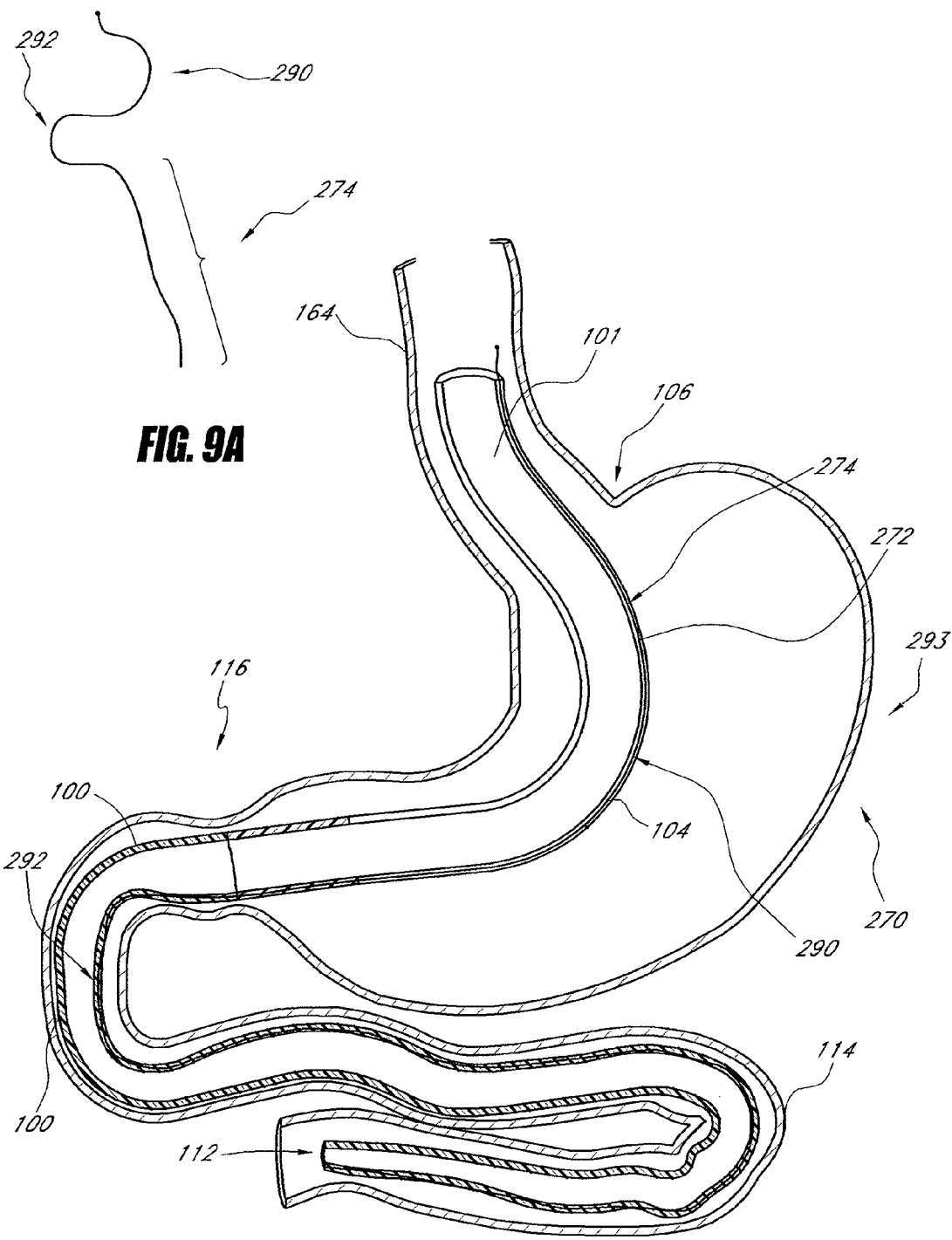
FIGS. 9A-9B illustrates a sleeve system with a support lumen configured to house a guidewire that can have one or more preset curves, according to one embodiment of the invention.
Figure 10:
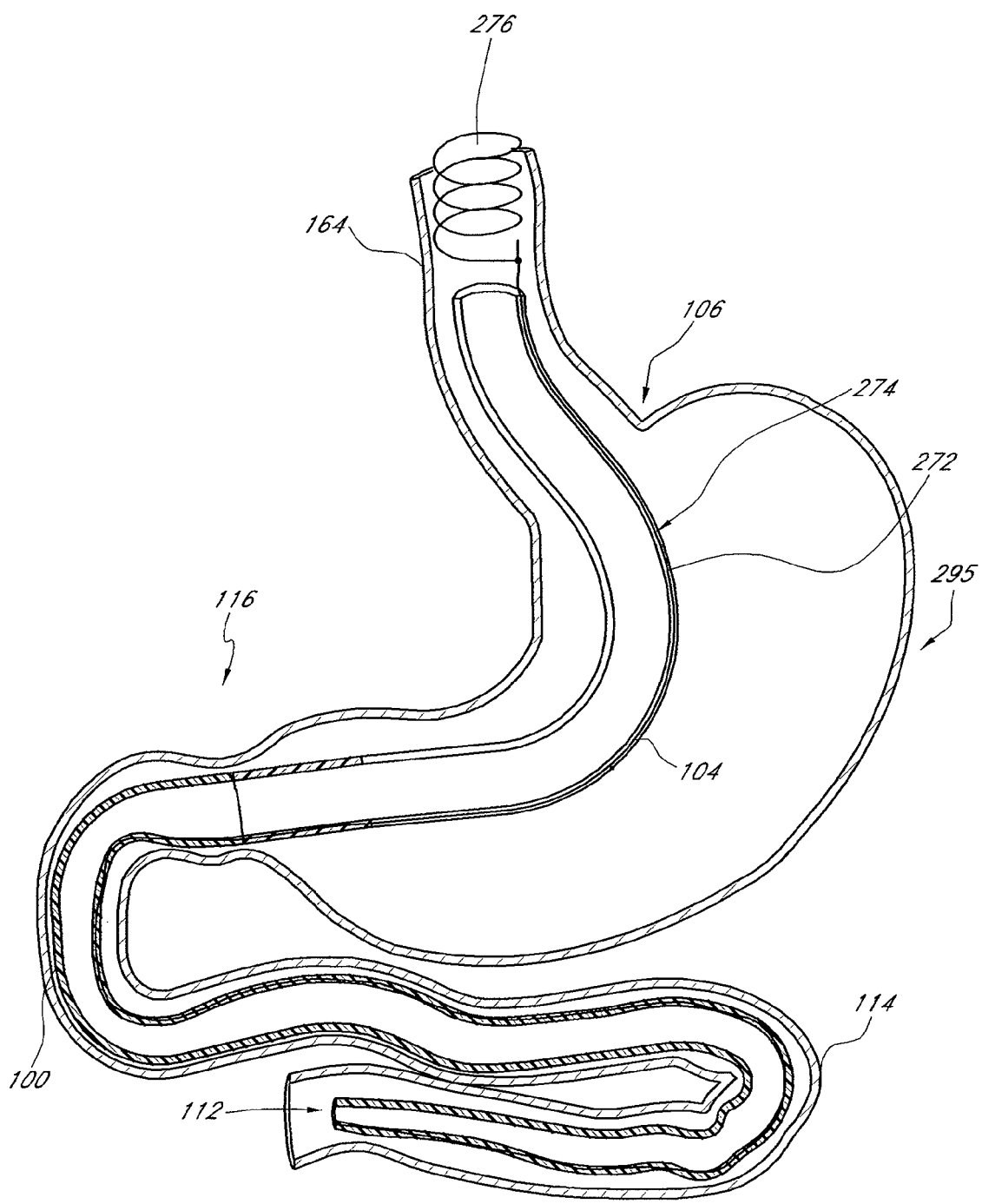
FIG. 10 illustrates a sleeve system with a guidewire that has a proximal portion extending above the proximal sleeve and forming a spiral shape, according to one embodiment of the invention.

In one embodiment, an intragastric support system could include a cuff/sleeve with one or more lumens built into the sleeve wall that run approximately from the proximal end to the distal end, as disclosed in the Kagan '148 application. Such a cuff/sleeve with one or more lumens in the sleeve wall can advantageously hold the sleeve in place with a stiffening element inserted into the lumen to resist movement of the sleeve proximally or distally. In other words, the sleeve could potentially be self-supporting with an elongate support element, such as a stiffening element (e.g., a guidewire) without other support or attachment structures. Following placement of the cuff/sleeve, a flowable polymer that polymerizes in situ can be injected into the lumen. Once this hardens, it will not only act as a stiffening member in the sleeve but will also keep the device from undesirably migrating proximally or distally along the GI tract. Instead of filling the lumen with a polymer, a support wire, for example a standard guide wire used for interventional procedures could be placed down a lumen in the wall of the sleeve. Alternatively, the sleeve could have support wire or wires built into the wall of the sleeve (as disclosed in the Kagan '148 application) to keep the sleeve in place or provide any radial force if desired. It may be that a sleeve with a stiffening element could have enough resistance to avoid displacement proximally or distally that it could function as a stand alone device. A stand alone supported bypass sleeve could run from above the GEJ, at the GEJ or immediately below the GEJ to the small intestine. Placement of the sleeve above the GEJ can advantageously help align the proximal sleeve with the esophagus. In one embodiment 293 depicted in FIGS. 9A-B, the sleeve 100 is a constant diameter so that food entering the sleeve 100 transfers minimal force that could displace the sleeve 100 distally. The proximal end 101 of the sleeve 100 in this configuration can have a slight radial hoop strength to keep opposition to the esophageal wall 164 but not enough to force the esophagus 164 open. The guidewire 274 could be as described above, or it could have one more preset curves 290, 292 as shown. The preset curves 290, 292 would combine many of the tasks of the separate elements of the intragastric support system described elsewhere. The preset curves 290, 292 would act as both the esophageal post 500, arcuate support element 206 along the greater curve and replace the looped pyloric support element 212 with a set curve 292 that braces along the outer curve of the duodenum. In some embodiments, the curve could be a reverse S type curve with the upper part 290 matching close to the greater curve of the stomach and the lower part 292 of the S close to the shape of the pylorus and upper duodenum. There would be no gasket (e.g., dome-shaped) element in this configuration. The sleeve 100 could be deployed inverted within a delivery catheter advanced to the pylorus 116 and toposcopically deployed in the small intestine 112. The delivery catheter still attached to the sleeve would be retracted up into the esophagus or to the desired location for the proximal end of the sleeve. While attached to the delivery catheter to keep from displacing the sleeve 100 distally the preset guidewire 274 would be advanced down the lumen. The guidewire 274 could be made of a shape memory metal such as nitinol or elgiloy. Ideally it would be cooled immediately before advancement so it would be as flexible as possible for advancement in the lumen. The guidewire 274 could have an atraumatic tip proximally or it could be slightly shorter than the lumen so it would not stick out after placement and a plug could be placed to lock the wire in the lumen. In another embodiment 295, as shown in FIG. 10, a portion 276 of the wire 274 can extend proximally beyond the sleeve 100. This proximal wire segment 276 may be an expandable element can assume a complex shape, such as a spiral shape, zig-zag stent, and the like to provide additional support within the esophagus 164 for the sleeve 100. Any of these sleeve stiffening methods could also be used with any sleeve embodiments as disclosed in any of the prior applications incorporated by reference above. In addition, any of the adhesive and ablation techniques described above could be used with the previously disclosed cuff embodiments. In these embodiments, the cuff could be made at least in part from materials such as tissue grafts, or other materials. The cuff could have a hybrid design with an annular cuff of one material and an outer cuff or section of cuff that is made of a material that encourages ingrowth or adhesion following the steps described above for surface preparation.

The total weight of the intragastric support system 504 in some embodiments, can be between about 0.05-0.5 kg, or between about 0.1-0.2 kg. The system 504 can have a low center of gravity in some embodiments, with at least about 60%, 65%, 70%, 75%, 80%, 85%, 90%, or more of the weight present in the distal support element 502 compared to the total weight of the system 504.

Obstructive or Restrictive Device

In some embodiments, the gastrointestinal support device may include an obstructive or restrictive component positionable in the esophagus and/or stomach. The obstructive or restrictive component can cause a portion of the gastrointestinal wall, such as at the lower esophageal sphincter in one embodiment, to expand, provoking a feeling of satiety in a patient and suppressing appetite.

Figures 11A, 11B, 11C:
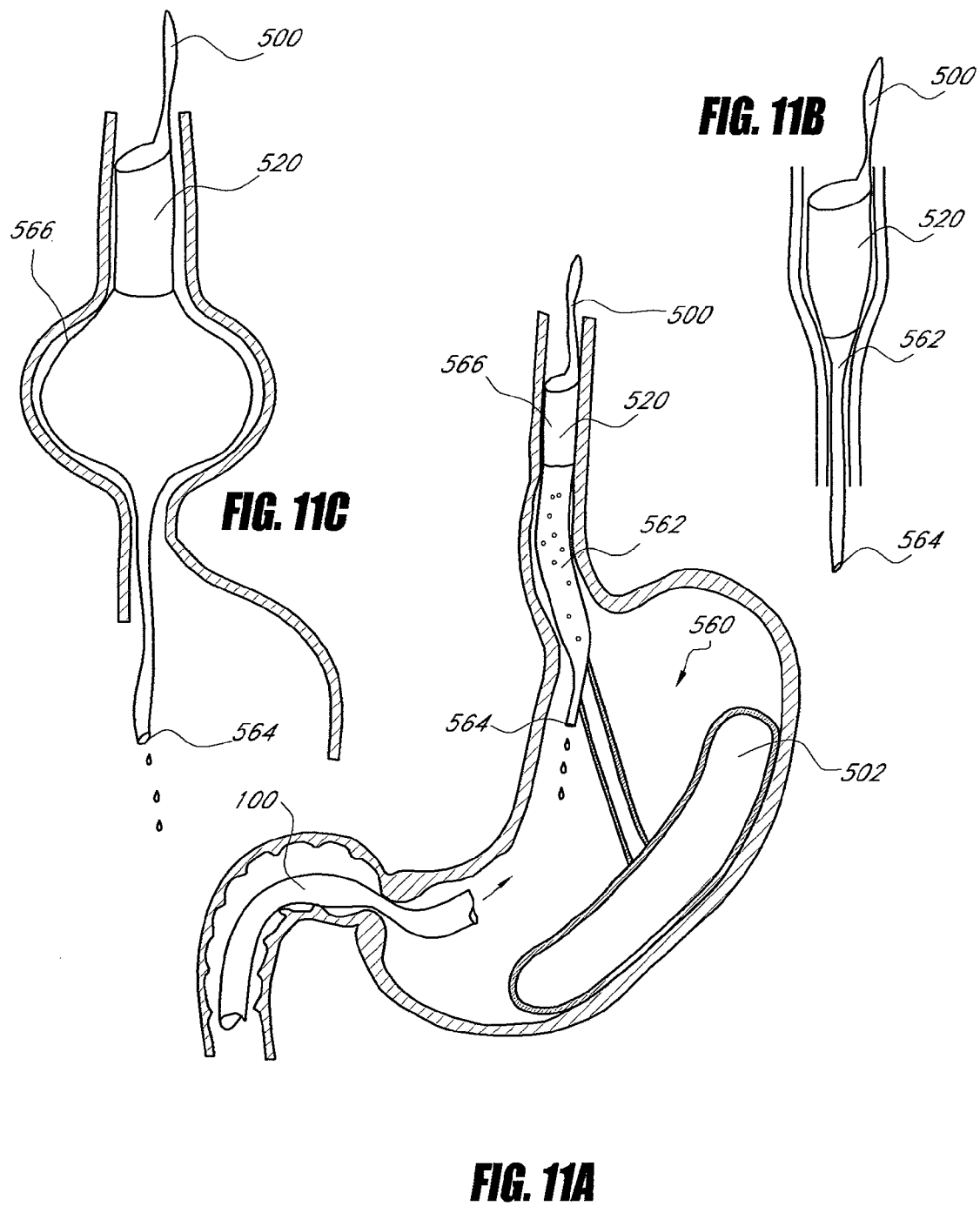
FIGS. 11A-D schematically illustrate an intragastric support system that includes a reservoir with a restrictive outlet, according to one embodiment of the invention.

As shown schematically in FIG. 11A, intragastric support system 560 includes a proximal orientation element 500 with a food-collection ring element 520 and distal support element 502 that can be as previously described. A reservoir 562 that can be stretchable, such as a balloon may be connected to ring element 520 as shown and extend distally into the distal esophagus or proximal stomach. The reservoir 562 can be, for example, a sponge-like bladder that expands, such as radially, in the presence of food or liquids. In some embodiments, the reservoir 562 is configured to radially expand in diameter by at least about 25%, 50%, 75%, 100%, 150%, 200%, or more of its unstressed diameter. The reservoir 562 is preferably easily compressible such that the lower esophageal sphincter 566 can still close down upon it, not impeding its normal function, as schematically illustrated in FIG. 11B. The balloon-like reservoir 562 can include a restrictive outlet 564, such as a smaller-diameter portion, a one-way valve, or the like to expand a portion of the gastrointestinal wall, e.g., at the GEJ and induce a feeling of satiety in the patient, as schematically illustrated in FIG. 11C.

Figure 11D:
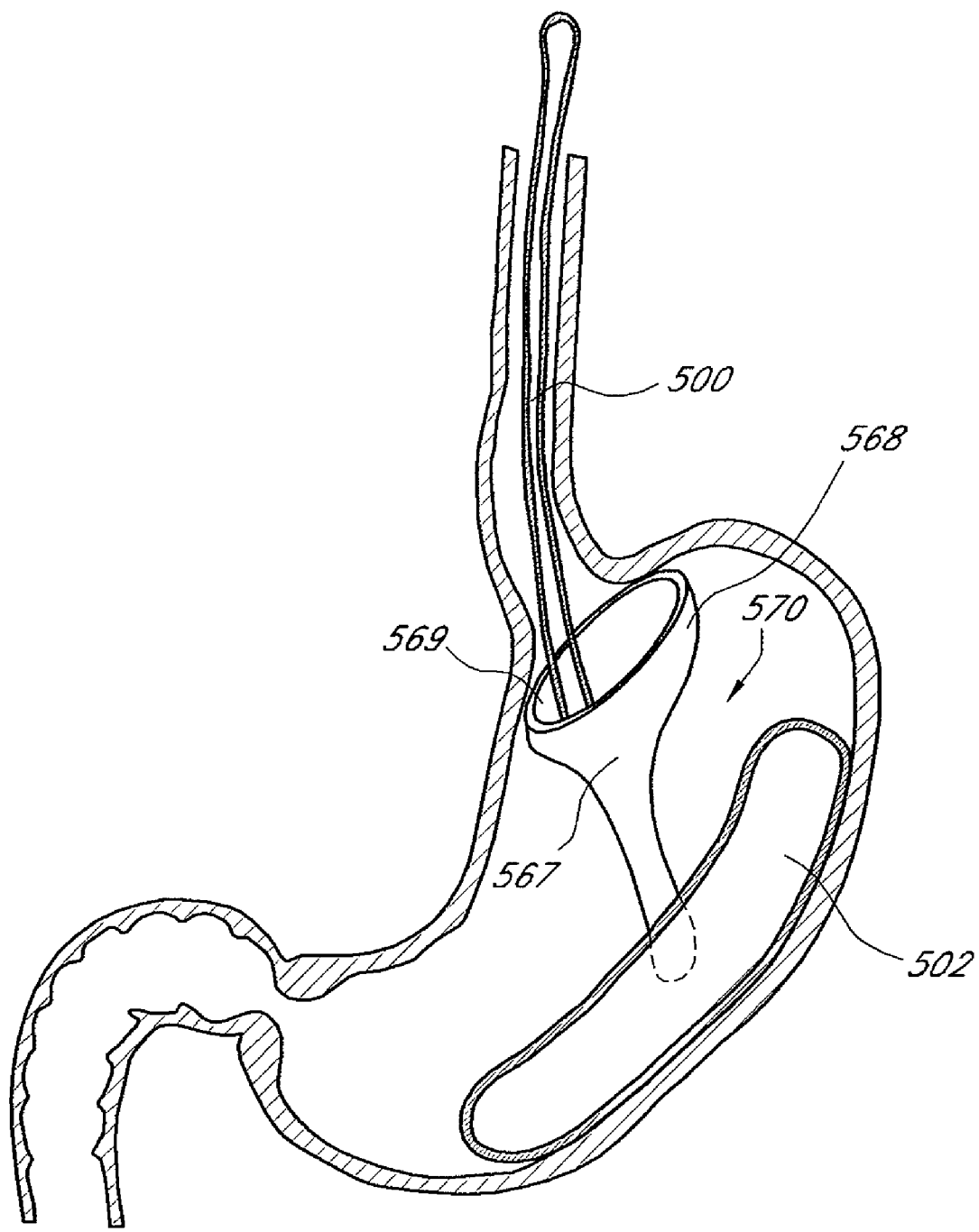

FIG. 11D illustrates another embodiment of an intragastric support system 570 including a restrictive element 568. Shown are proximal orientation element 500 and distal support element 502. A diaphragm 568 with a funnel-like portion 569 and a distal restrictive outlet 567 may be positioned in the proximal stomach to collect food and liquids from the esophagus as illustrated. The narrow restrictive outlet 567 can cause food and liquids to exert pressure on the GEJ, inducing a feeling of satiety in the patient.

Figure 11E:
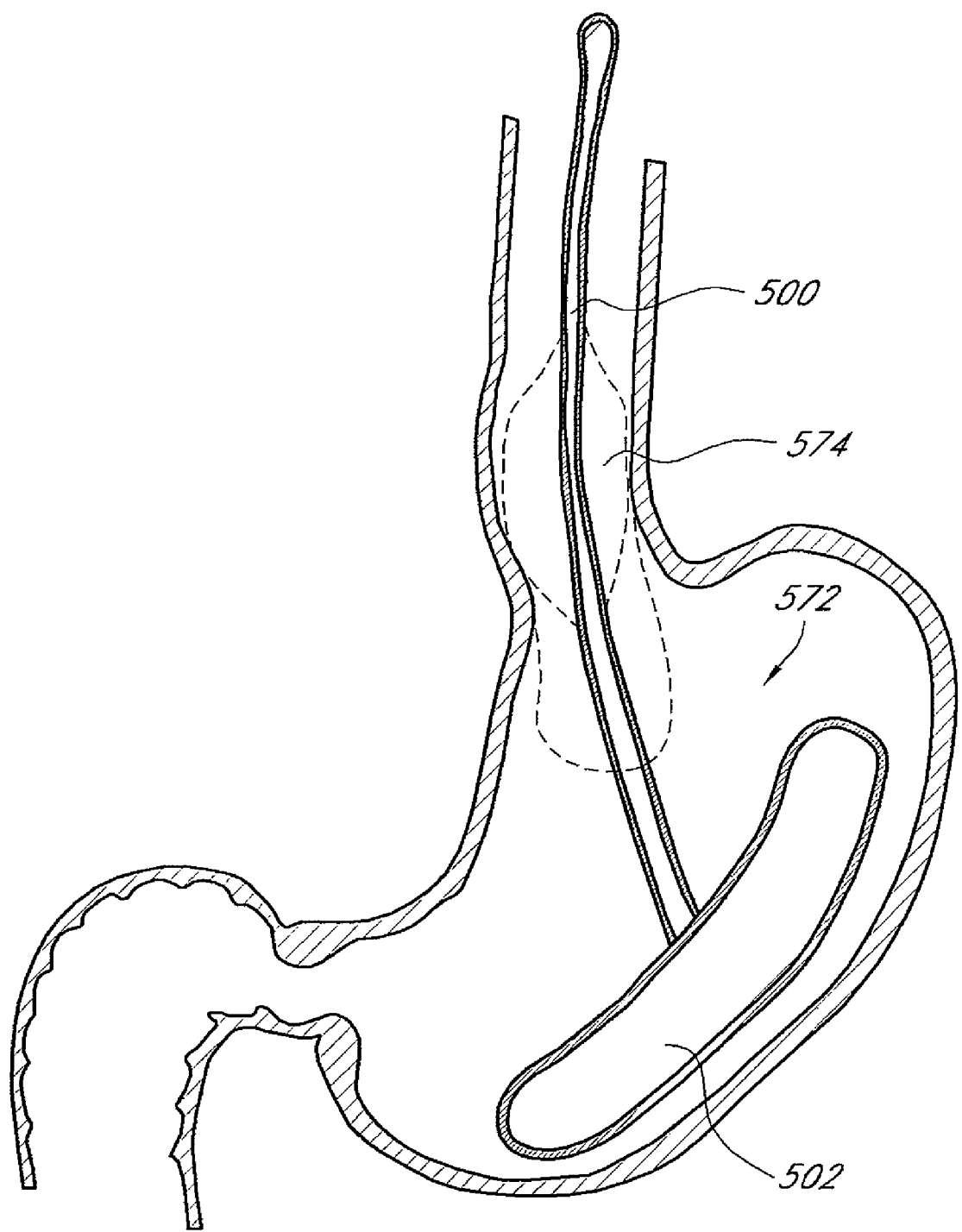
FIG. 11E schematically illustrates an intragastric support system that includes a reservoir with an obstructive element, according to one embodiment of the invention.

FIG. 11E illustrates an embodiment where the intragastric support system 572 includes an obstructive element 574 operably connected to the proximal orientation element 500 and is configured to be positioned, for example, at the GEJ. The obstructive element 574 may be a balloon or sponge that can expand, contract, or otherwise change shape. Food and liquids from the esophagus can be forced to flow around the obstructive element 574 into the stomach (rather than through the restrictive elements illustrated in FIGS. 11A-D above) exerting pressure on the GEJ and inducing a feeling of satiety in the patient. In some embodiments, the obstructive element can include a filter, to function as a sieve for ingested materials.

In some embodiments, the restrictive or obstructive element includes a control that can allow the degree of expansion of the reservoir and/or the degree of the restriction. In some embodiments, the reservoir includes a sensor that can measure a pressure change, e.g., at the LES and cause dilation of the GEJ, such as to prevent reflux or induce satiety.

Gastric Bypass Device

Figure 12:
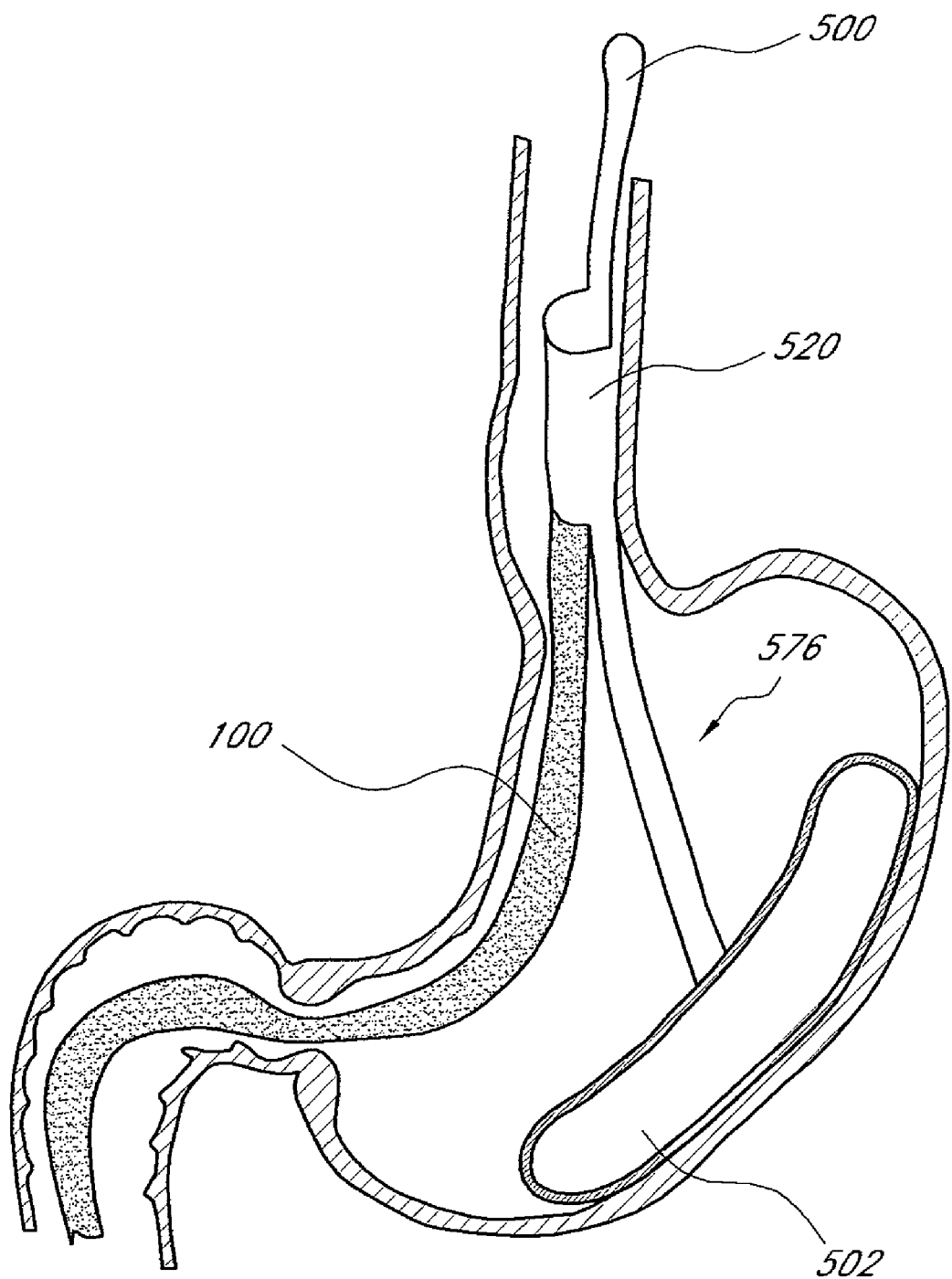
FIG. 12 schematically illustrates an intragastric support system that includes a gastrointestinal bypass sleeve, according to one embodiment of the invention.

In some embodiments, as illustrated schematically in FIG. 12, the intragastric support system 576 may be as previously shown with proximal orientation element 500 including a food collection ring 520, as well as a distal support element 502 as previously described. There can be a balloon-like reservoir with a restrictive outlet (not shown) to receive food and expands against the gastro-esophageal junction (GEJ) due to the restrictive outlet. This element is easily compressible so that the LES can still close down on it not impeding its normal function. Also illustrated in FIG. 12 is a gastrointestinal sleeve 100 that can be connected proximally to an esophageal ringed element 520 on the proximal orientation element 500 at the GEJ, or in other embodiments, a reservoir structure below the GEJ. The sleeve 100 may be made of a pliable or collapsible material, or be as described, for example, in U.S. Patent Pub. No. 2007/0198074 A1 to Dann et al., hereby incorporated by reference in its entirety. The length of the bypass sleeve 100 may vary, and can be at least about 50 cm, 75 cm, 100 cm, 125 cm, or more in some embodiments. The sleeve 100 can be made to bypass the stomach only, bypass stomach+intestine, or bypass intestine only. In the case of a partial intestinal bypass, the sleeve 100 could be operably attached to the intragastric support component 502 (such as through an aperture of the distal support element) near the pyloric antrum. Additional features such as, for example, a balloon or sponge can also be attached to the system to enable the stomach to better act on the sleeve during peristalsis, as contraction of the stomach can exert a pressure on the balloon or sponge which will in turn exert a pressure on the sleeve.

Gastric Space-Occupying Device

Figure 13:
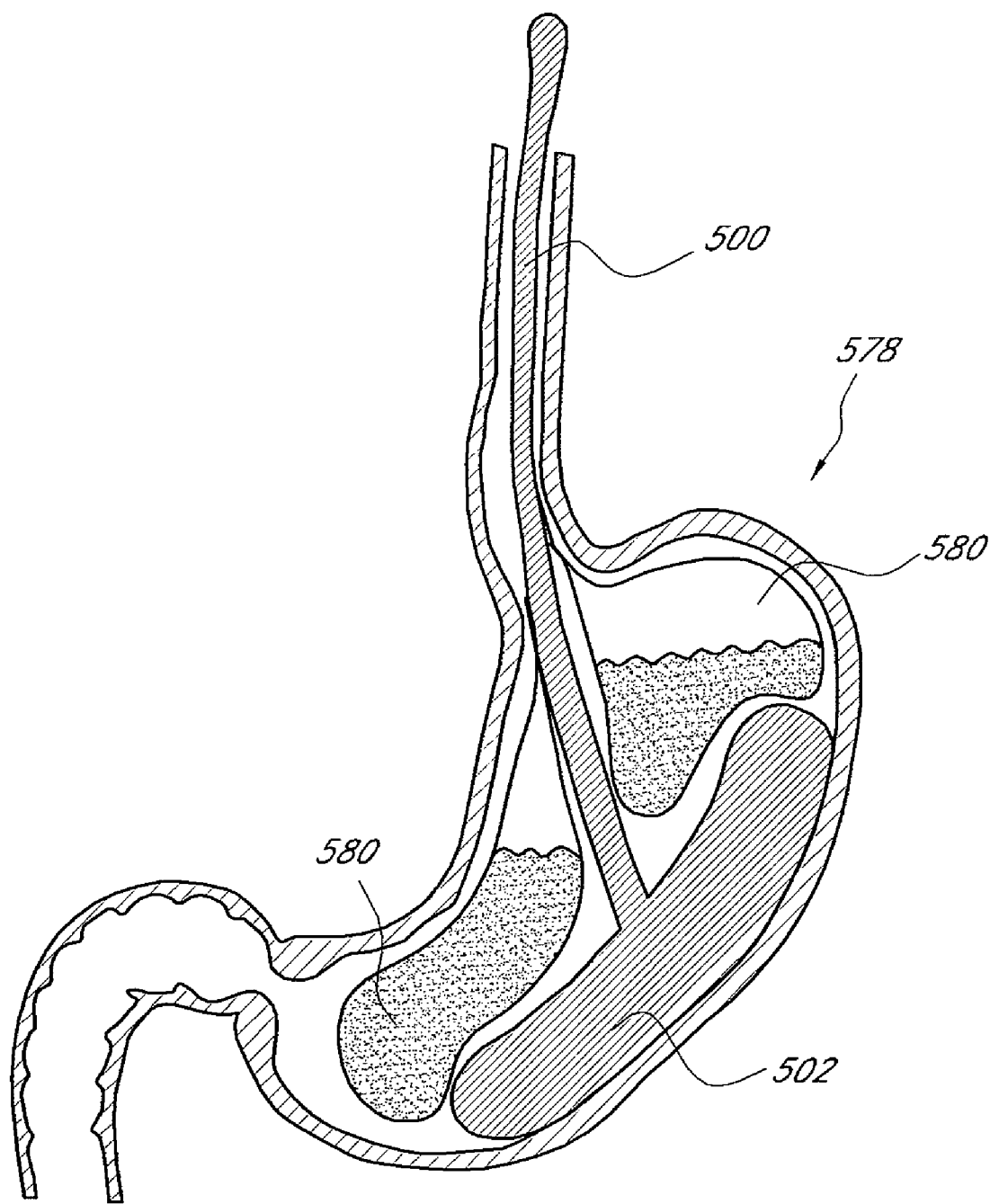
FIG. 13 schematically illustrates an intragastric support system that includes an expandable structure to occupy space in the stomach, according to one embodiment of the invention.

In one embodiment, as illustrated schematically in FIG. 13, a intragastric support system 578 includes one or more expandable structures 580, 580 that may be, for example, balloons tethered to a portion of the system 578. In some embodiments, the expandable structures 580, 580 can be fillable with air, fluid, or other material to occupy the empty space of the stomach, to reduce free gastric capacity and induce a sense of satiety.

Delayed Gastric Emptying Device

Figure 14:
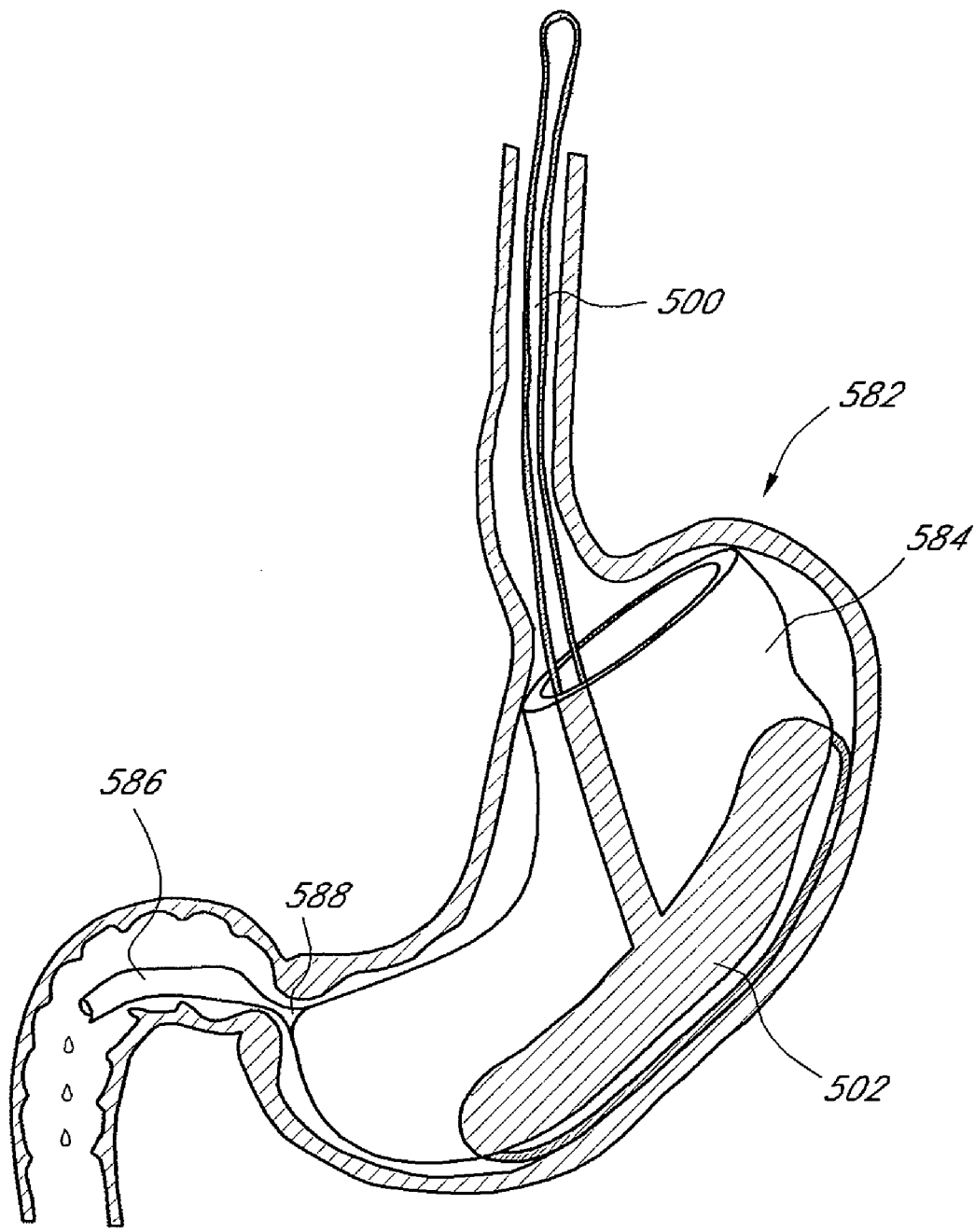
FIG. 14 schematically illustrates an intragastric support system that includes a pyloric valve to delay gastric emptying, according to one embodiment of the invention.

In one embodiment, illustrated schematically in FIG. 14, an intragastric support system 582 that may be otherwise as previously described can include a pyloric valve 588 tethered to a portion of the system 582 to control or regulate the food passage from the stomach into the duodenum. The valve 588 could span the pylorus or be fixed in front of the pylorus partially blocking food from passage out of the stomach. The intragastric support system 582 could tether a large reservoir 584 (e.g., a bag) in the stomach with a restrictive outlet 586 as shown, thus limiting the rate of food passage through the pylorus.

Pacing Device

Figure 15:
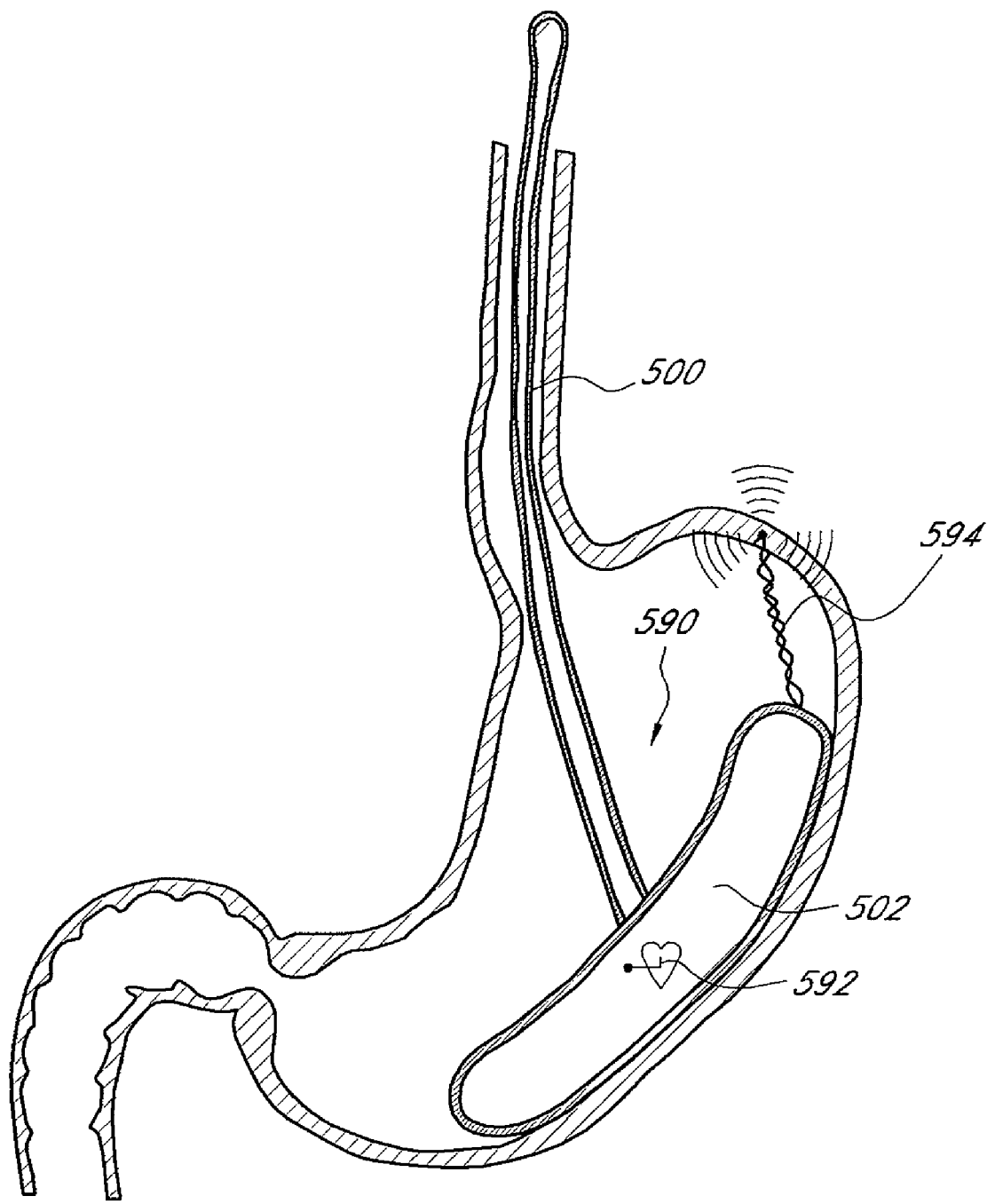
FIG. 15 schematically illustrates an intragastric support system that includes a pacing or stimulating element, according to one embodiment of the invention.

In one embodiment, illustrated schematically in FIG. 15, the intragastric support system 590 can include a pacing/stimulating element 592 whereby the pacing device could be housed, for example, in the distal support element 502 (or "foot") of the device and one, two, or more leads 594 could be attached to the gastric wall, pyloric antrum, or nerves (such as the vagal trunk) to stimulate the muscles or nerves via electrodes/leads to treat, for example, motility disorders such as gastroparesis. The device could incorporate a basket-like sensing array (not shown) used in conjunction with the pacing features. Some pacing elements 592 that can be used in conjunction with the IGS systems described herein are described, for example, in U.S. Patent Pub. No. 2008/0058887 to Griffin et al., which is hereby incorporated by reference in its entirety.

Food Incinerator

Figure 16:
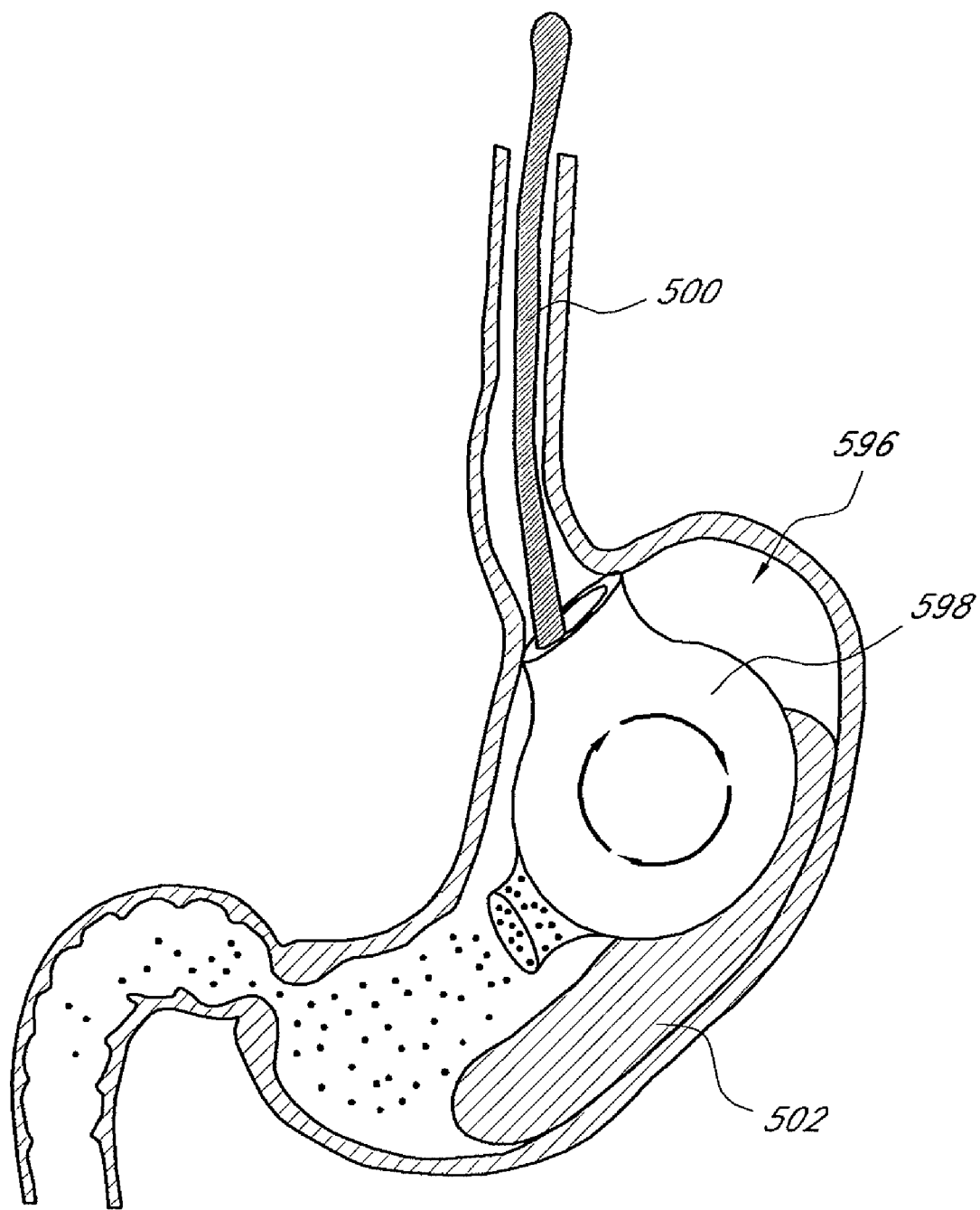
FIG. 16 schematically illustrates an intragastric support system that includes a reservoir configured to alter ingested materials, according to one embodiment of the invention.

In one embodiment, as shown schematically in FIG. 16, an intragastric support system 596 could support a reservoir 598 which chemically or mechanically alters or neutralize potential calories, proteins, fats, sugars, etc. contained in the food or liquids ingested. For example, the reservoir 598 may contain acids, bases, pharmaceutical agents, and/or enzymes such as amylase, lipase, or proteinases. In some embodiments, the food or liquid is altered into a form that is more or less absorbable by the digestive tract. In some embodiments, the reservoir 598 is configured to metabolize a drug or substance, such as alcohol to increase or reduce absorption of the drug or substance or convert it to a more, less or non-active metabolite.

Implantable Diagnostic Device

Figure 17:
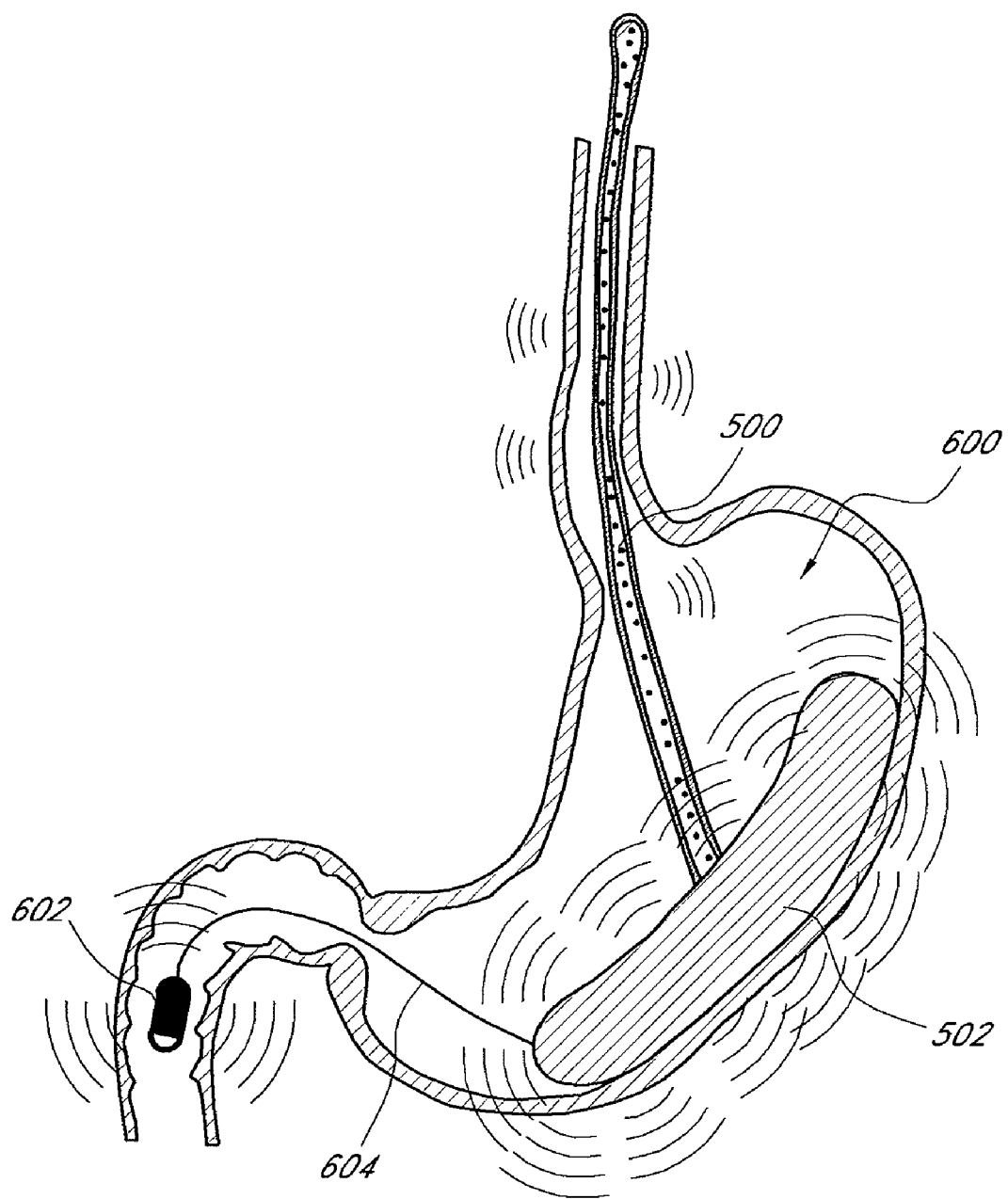
FIG. 17 schematically illustrates an intragastric support system with a distal support component that includes an implantable diagnostic device, according to one embodiment of the invention.

As shown schematically in FIG. 17, the distal support element 502 of an intragastric support system 600 could house or tether various imaging technologies 602 such as endoscopic ultrasound (EUS), a sensor, probe, camera (such as a capsule endoscope), or the like that is tethered via a tether line 604 in the stomach and allowed to travel into the intestine. The imaging element 602 can later be retrieved mechanically, such as manually or via an automated retraction feature. Alternatively, the tether 604 may be degradable over time allowing the diagnostic device 602 to pass through the colon and exit the body. A tethered device 602 or an element incorporated within the intragastric support system 600 itself can measure, for example, one or more of pH level, intra-gastric pressure, food intake amount and rate, gastric temperature, electrical activity from the heart (e.g., EKG), or other hemodynamic parameters noninvasively, such as systolic and diastolic blood pressure, atrial, ventricular, central venous, and pulmonary artery pressures. The device 602 can transmit the information to an external and/or internal receiver. In some embodiments, the device 602 can be a comprehensive implantable ICU monitoring unit.

Chemical Detector

In some embodiments, a tethered device or the intragastric support system itself is incorporated with a sensor configured to detect, for example, the presence of one or more toxins (e.g., a heavy metal, a poison) or allergen that can send the alert to an external device and/or can administer therapy (e.g., an antidote, a chemical to break down the toxin or allergen, epinephrine, a corticosteroid, an antihistamine) to prevent toxicity or an allergic reaction.

Implantable Therapeutic Device

In some embodiments, at least a portion of the intragastric support system is incorporated with a drug delivery function in, for example, the esophagus, stomach or intestine. This could deliver therapies as one or more of the following: a reaction to the sensing feature; administer prophylactic treatment; time-release medication, neutralize hormonal releases; and/or other therapeutic applications. In one embodiment, a capsule tethered to the device could also serve as a cautery in the stomach or intestine to treat ulcers, polyps, cancers, arteriovenous malformations, areas of infection, and the like.

In some embodiments, the intragastric support system is incorporated with a reservoir to store an energy source, such as glucose for endurance-type activity or for outdoor sports to provide sustained energy. The reservoir may be replenishable. This can be used advantageously in recreational or military training or combat situations, for example.

In some embodiments, the intragastric support system may include a thermoregulatory element such as a heat source or cooling source to maintain body temperature in extreme weather conditions.

In some embodiments, the intragastric support system can include a power generator, such as a battery, to provide energy to electronics or electrical devices internal and/or external to the body.

In some embodiments, the intragastric support system can include an accelerometer to detect body motions or orientation; data can be transmitted to a processing unit inside or external to the body.

In some embodiments, the drug delivery platform can include a drug to treat a wide variety of conditions depending on the clinical result. For example, in some embodiments, the distal support element can include a drug to treat peptic ulcer disease, gastritis, or GERD such as a proton-pump inhibitor, H2 receptor blocker, prostaglandin or prostaglandin analogue, sucralfate, or bismuth subsalicylate. The distal support element could include a drug to treat a motility disorder or chronic nausea/vomiting such as a pro-motility agent such as metoclopramide or an anti-emetic agent such as ondansetron, chlorpromazine, or droperidol, for example. The distal support element could include a chemotherapeutic agent to treat cancer, such as gastric cancer, e.g., 5-FU, cisplatin, epirubicin, etoposide, docetaxel, or irinotecan. The distal support element could include an anti-obesity drug, such as, for example, orlistat, metformin, sibtramine, exenatide, pramlintide, rimonabant, an amphetamine, naloxone, or a hydrogel. An intragastric drug delivery platform can be especially advantageous for patients who have difficulty with compliance with orally administered medications that may need to be taken chronically. In some embodiments, other non-limiting examples of drugs that can be included on the drug delivery platform could include an antipsychotic, an antidepressant, an oral contraceptive, a hypoglycemic agent, an anti-hypertensive, an anti-coagulant, an antibiotic, an-antiepileptic, and many other drugs depending on the desired clinical result. In some embodiments, the proximal orientation element could also include a drug delivery platform, such as, for example, a chemotherapeutic agent to treat esophageal cancer.

Reflux Treatment

In some embodiments, the intragastric support system (also referred to herein as the IGS) includes one or more sensors that can measure pH levels in the esophagus. In some embodiments, the IGS includes a reservoir of a basic substance such as sodium bicarbonate to neutralize gastric acid. The IGS may also include a pressure sensor to measure pressure at, for example, the lower esophageal sphincter (LES). If LES pressure are too low, the sensor could trigger filling of a bladder operably connected to the IGS device that compensates for poor LES function and prevents acid reflux into the esophagus. Such a system can be controlled remotely. In some embodiments, the IGS device is incorporated with a plug of cotton or other absorbent material (tampon-like) feature to absorb acid at the lower esophageal sphincter (LES).

Gastric Prosthesis

In some embodiments, the IGS includes features to restore an anatomical defect, such as a hiatal hernia, by acting as a prosthetic device to prevent or to correct the deformity. There could have dome-like elements as described above or different geometries attached to the IGS to restore or prevent tissue abnormalities.

Natural Orifice Transluminal Endoscopic Surgery (NOTES) Applications:

In some embodiments, the IGS is incorporated with an intra-gastric "workstation" to facilitate NOTES procedures so that the surgeons can stage items or instruments necessary during the operation without the need to transport items multiple times into the body cavity. For example, the IGS device can include one or more dilators as a space creator in the stomach. In some embodiments, the IGS device is incorporated with a secondary instruments leverage point to support NOTES procedure intra-gastrically.

Stent Placement Applications

Figure 17A:
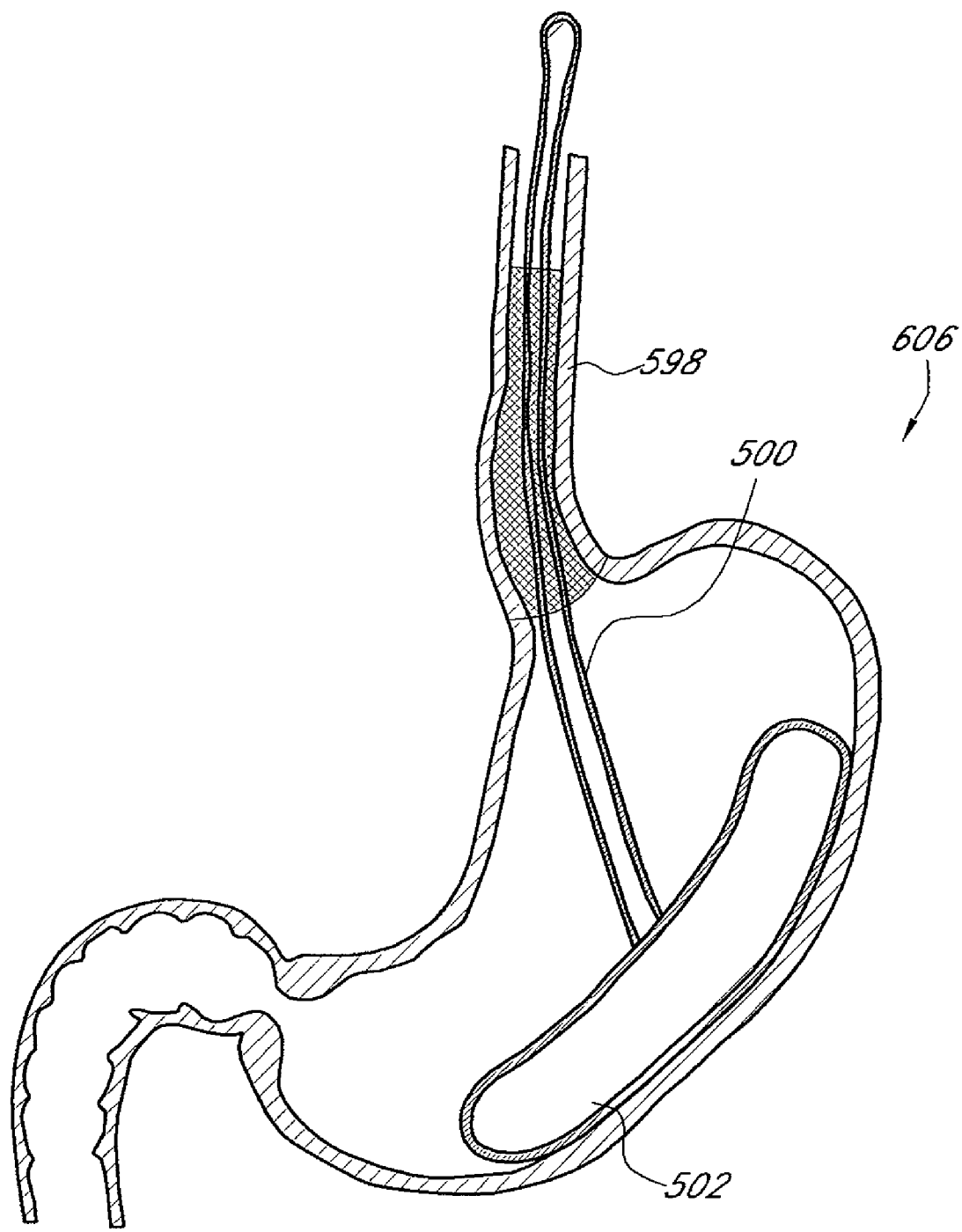
FIG. 17A schematically illustrates an intragastric support system with a distal support component that includes a stent or graft support feature, according to one embodiment of the invention.

In some embodiments, the IGS 606 can include a gastric stent support or graft support feature 598 to provide alternate stent placement technique, as illustrated schematically in FIG. 17A with proximal orientation element 500 and distal support element 502. Stents, such as those used for esophageal cancers or leaks, rely on outward force against the esophagus, to hold them in place. The IGS would support such stents from below.

Delivery Methods

One delivery method for an intragastric support system is disclosed. In some embodiments, as disclosed in the Dann '605 application, as well as U.S. Provisional Patent Application No. 60/826,862 to Dann et al., filed Sep. 25, 2006 and hereby incorporated by reference in its entirety, a cuff/sleeve 100 that includes an attached guidewire 152, as illustrated schematically in cross-section in FIG. 18D within delivery catheter 400 and overtube 480, can be delivered toposcopically. Furthermore, additional details regarding toposcopic delivery of a gastrointestinal sleeve 100 may be as described, for example, in U.S. patent application Ser. No. 11/861,156 filed Sep. 25, 2007, and hereby incorporated by reference in its entirety. More specifically, for example, FIGS. 1A-2E of the 11/861,156 application and the accompanying text at paragraphs [0054] to [0064] disclose various embodiments of toposcopic sleeves; FIG. 15H and the accompanying text at paragraph [0143] disclose an embodiment of a filling catheter and sleeve kit; and FIGS. 3A-16B and the accompanying text at paragraphs [0065] to [0142] and [0144] to [0150] disclose various toposcopic delivery systems and components including collapsible and steerable filling catheters, guidewires, techniques for occluding the distal end of the sleeve, and loop snares, all of which can be used or modified for use with the systems and methods described herein.

Figure 18A:
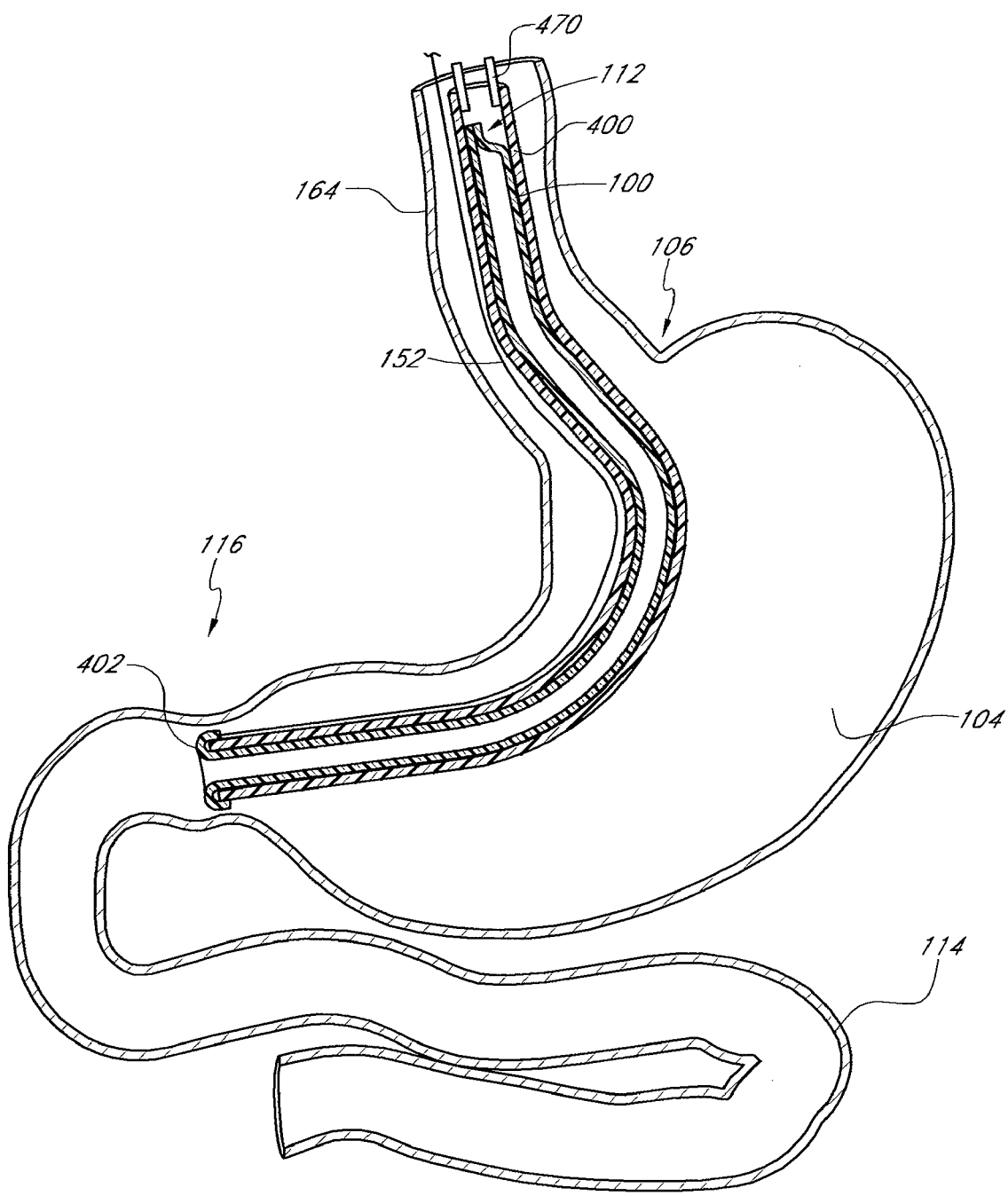
FIGS. 18A-18L schematically illustrate a method for delivering an intragastric support system utilizing a guidewire, according to one embodiment of the invention.
Figure 18B:
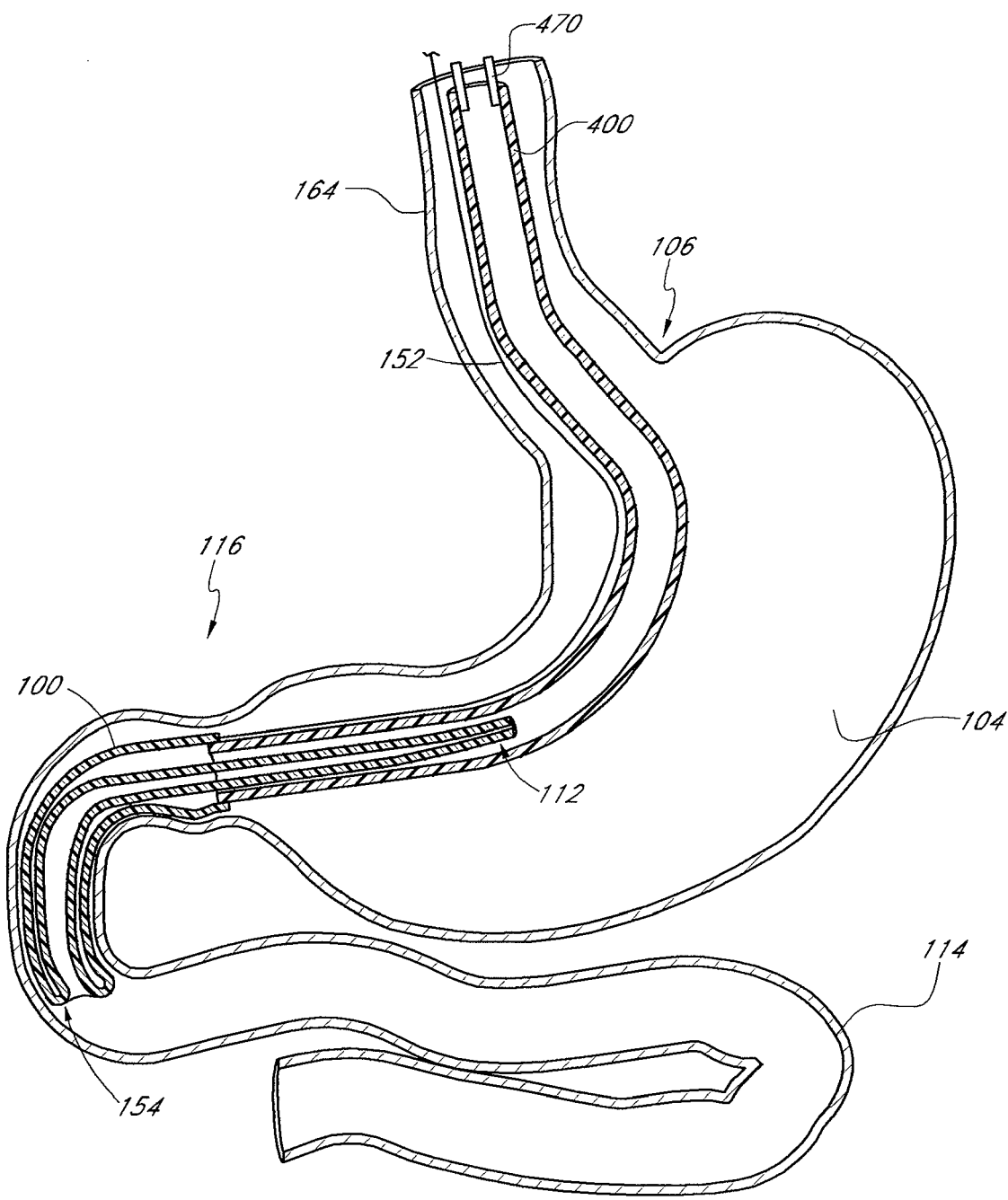
Figure 18C:
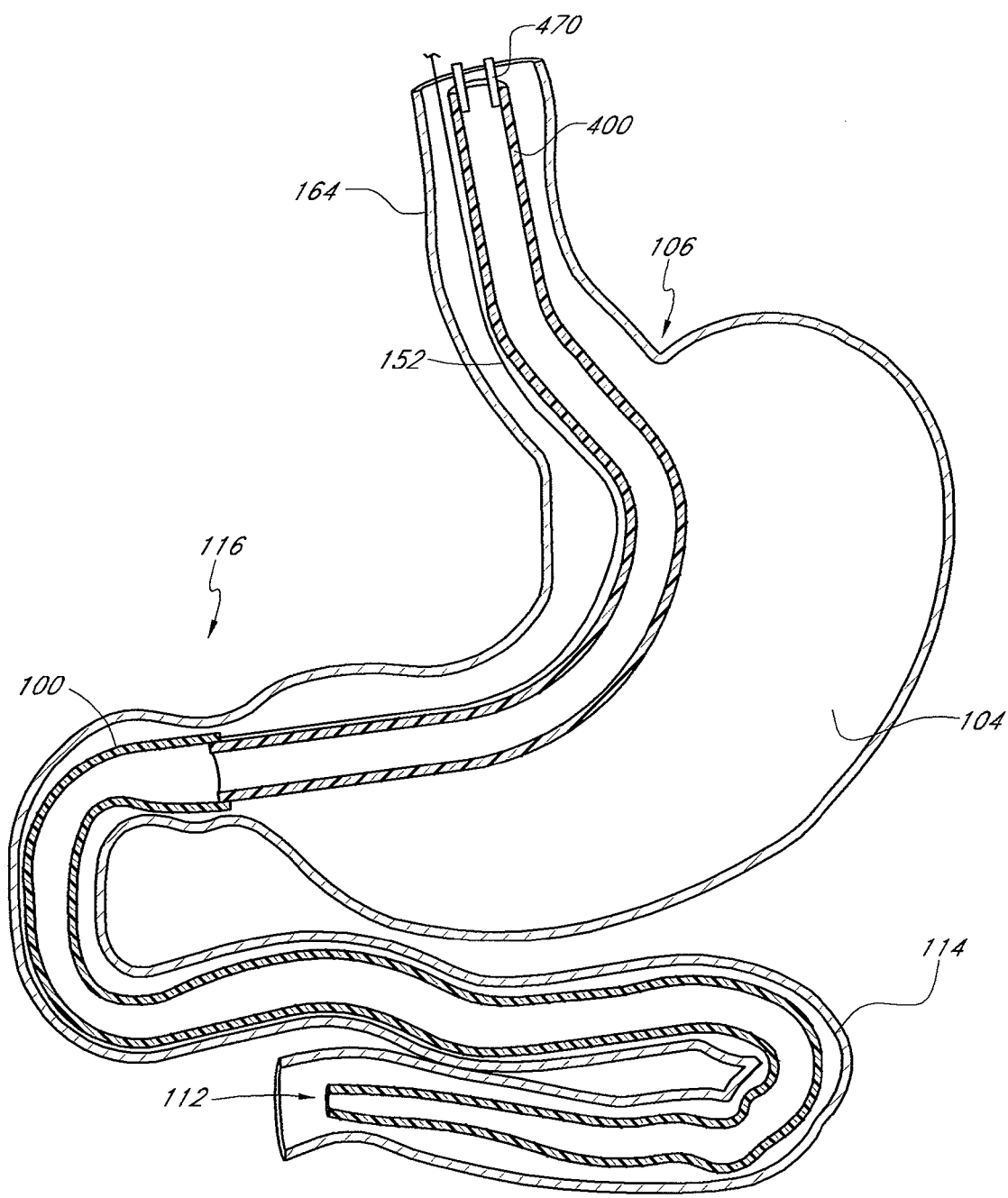
Figure 18D:
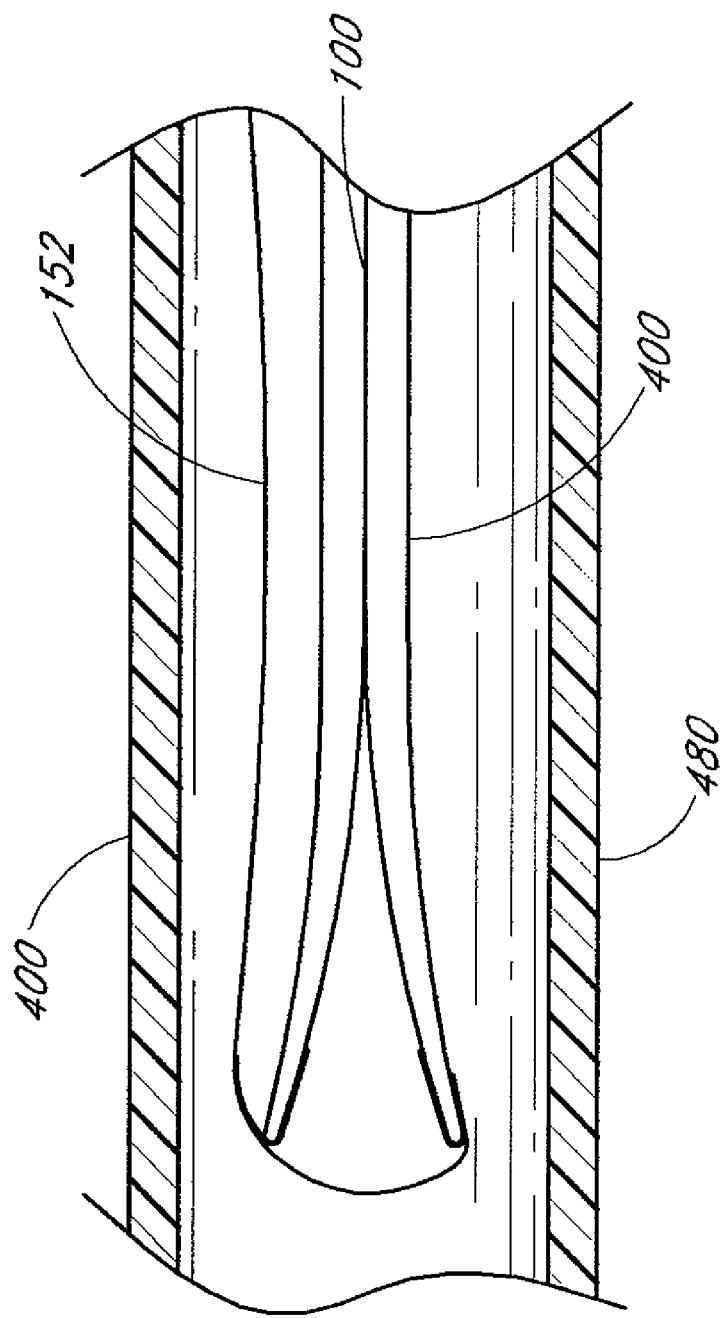
Figure 18E:
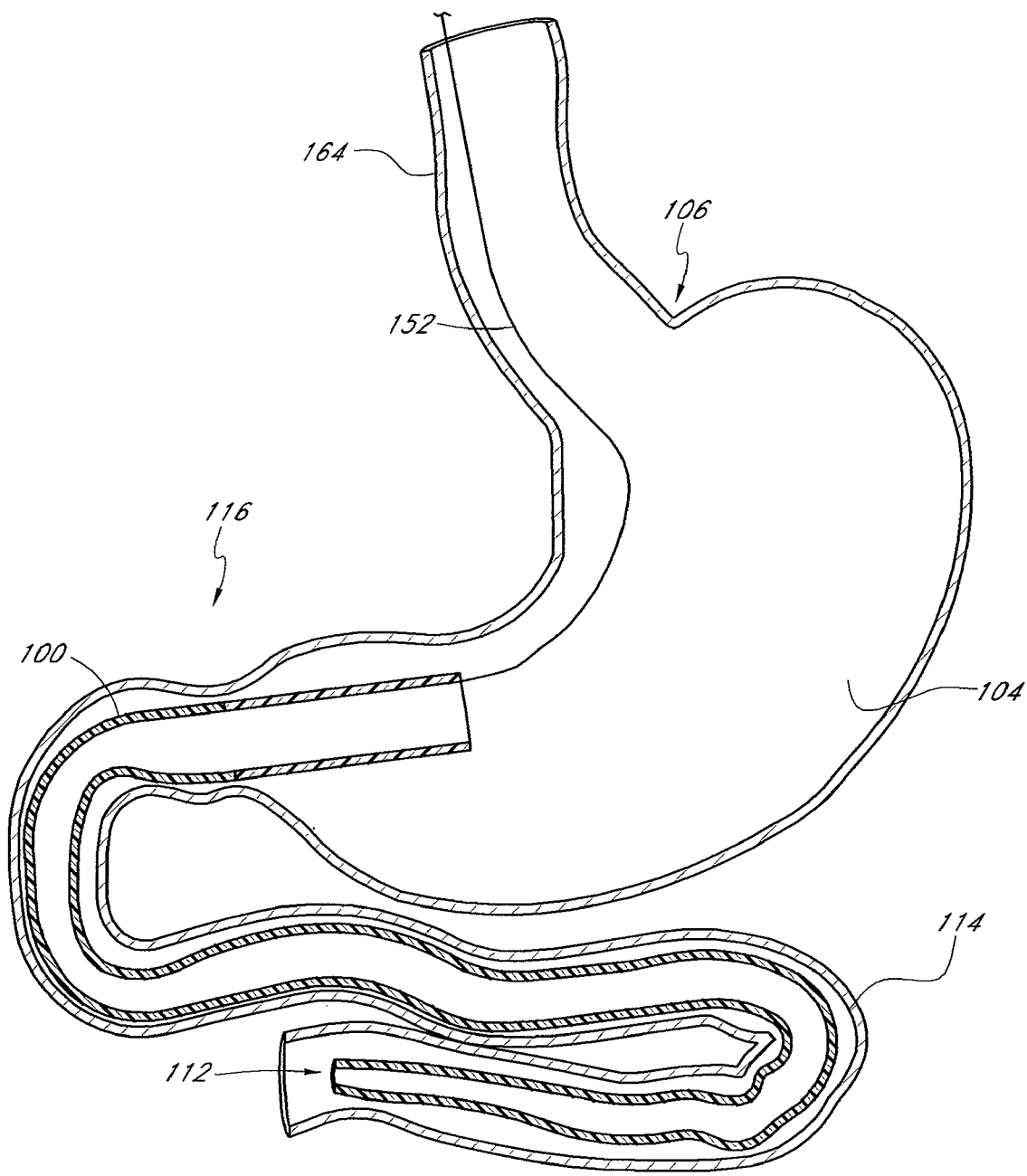

The overtube 480 of FIG. 18D is not shown in some of the following figures for clarity. An intragastric support system for securing the cuff/sleeve in position, such as an intragastric support system that includes a proximal orientation element, distal support element including a pyloric support element, arcuate element connected to a dome element and the pyloric support element (e.g., the system described above in FIGS. 1C-1E), can then be delivered over the guidewire. Other systems disclosed herein can also be delivered using similar methods.

Referring to FIG. 18A, there is illustrated a toposcopic delivery device in accordance with the present invention. The delivery device includes a filling catheter 400, illustrated as extending across the stomach such that a distal end 402 is in the vicinity of the pylorus 116. Preferably, the distal end 402 would be placed across the pylorus 116 before delivery of the sleeve 100. A sleeve 100 can be inverted within the filling catheter 400 for toposcopic delivery as disclosed in the Kagan '148 application. Stages of partial and complete eversion of the sleeve 100 is illustrated in FIGS. 18B-18C.

The proximal end of the sleeve 100 is connected to a guidewire 152. The guidewire 152 lies along the outside of the delivery catheter 400 during delivery of the sleeve 100. There may be one or more guidewires 152 connected to the proximal end of the sleeve. The guidewire 152 allows control of the sleeve 100 after deployment of the sleeve 100 into the small intestine 114. The guidewire 152 also functions as a control element for the sleeve 100 and should not be limited to a wire concept. A catheter connected to the sleeve 100, multiple catheters or any other linear device which would allow retraction of the sleeve 100 up to the GEJ from outside the body could be used instead of a guidewire 152.

The guidewire 152 is preferably releasably connected to the proximal end of the sleeve 100. Following connection of the sleeve 100 to the intragastric support system shown in FIG. 18K, the guidewire 152 is disconnected from the sleeve. Release may be accomplished in any of a variety of ways, such as thermally releasing a polymeric link through the use of a monopolar or bipolar electrical circuit as is understood in the detachable intracranial aneurysm coil field, or the like. Alternatively, the guidewire 152 may comprise a hollow outer sleeve which axially slideably receives an inner core. Axial, proximal or distal displacement of the core with respect to the sleeve can be utilized to detach the guidewire 152. The guidewire 152 may also be forceably detached, by a pushing, twisting or pulling motion. A catheter could be advanced over the guidewire 152 such that when the tip of the catheter comes into contact with the proximal end of the sleeve 100 the guidewire is disconnected by force or through the actuation of a cutting mechanism.

Figure 18F:
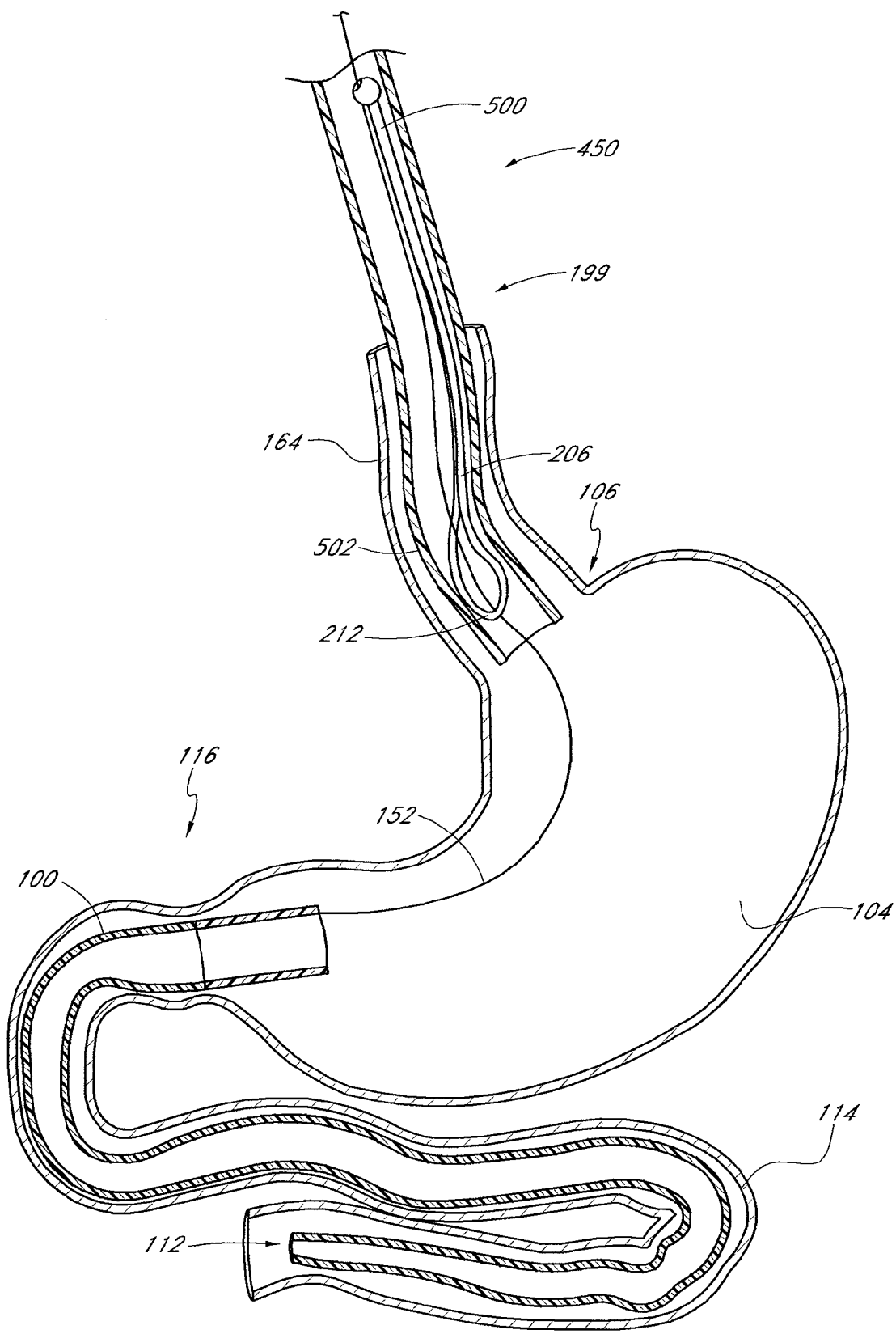
Figure 18G:
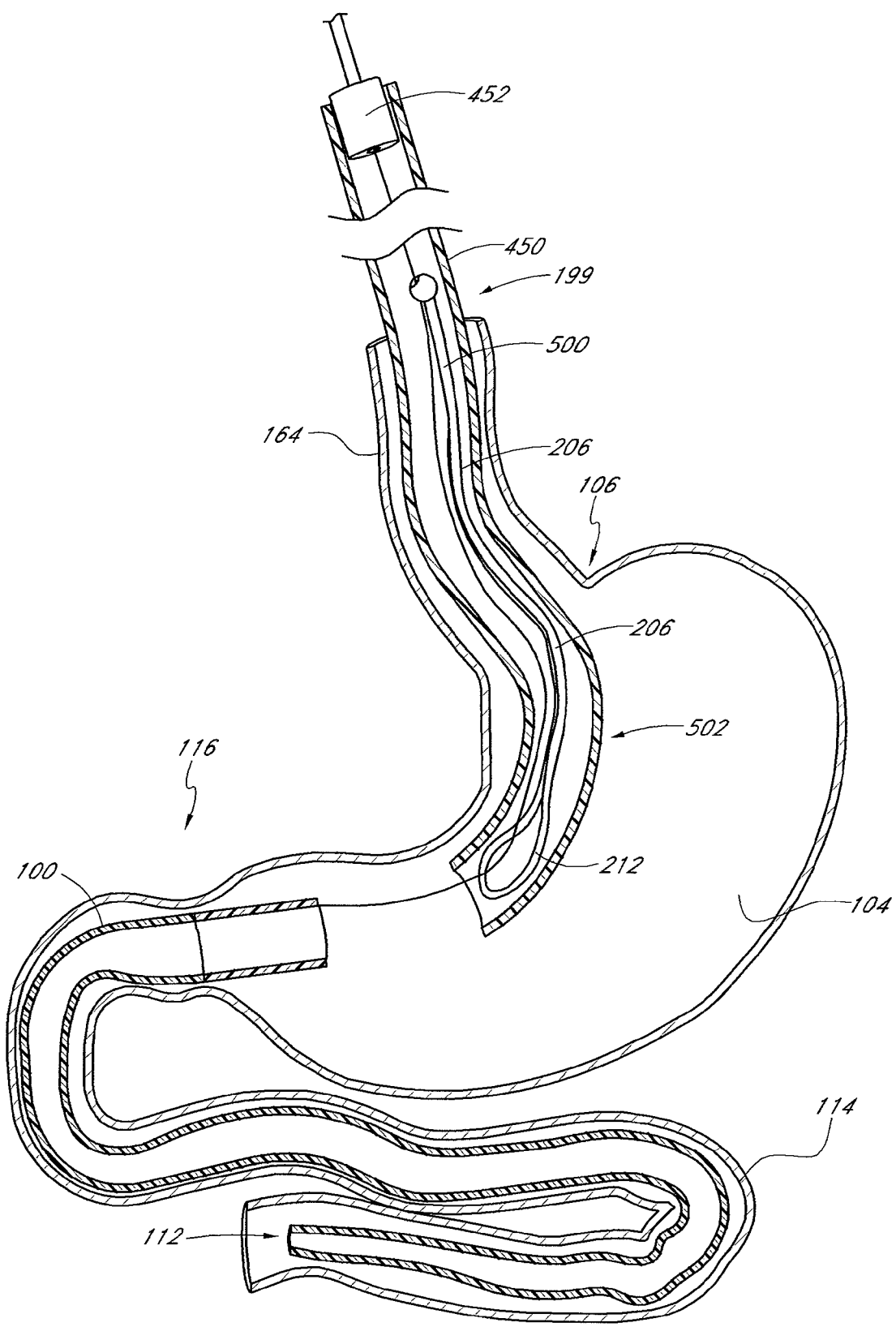
Figure 18H:
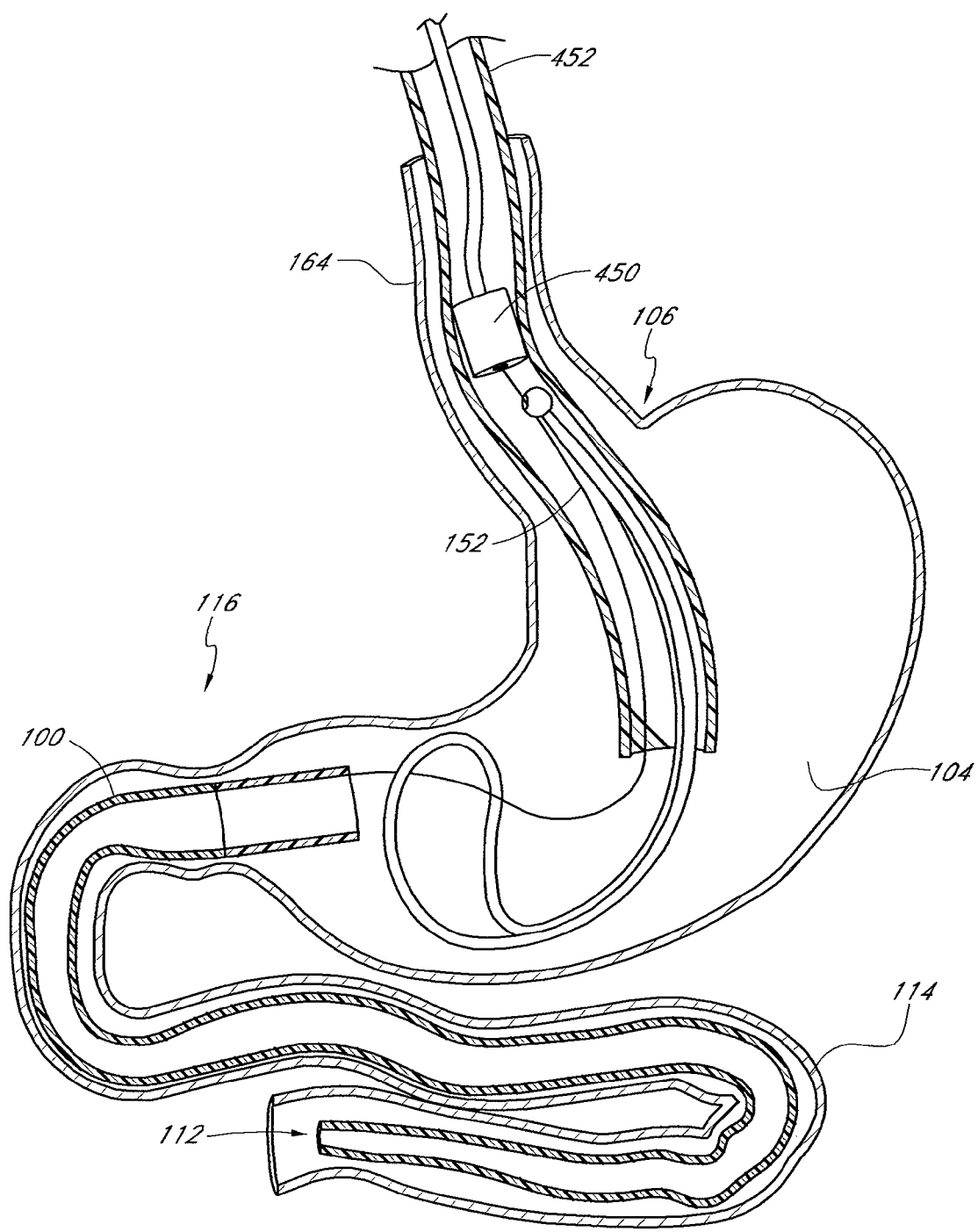
Figure 18I:
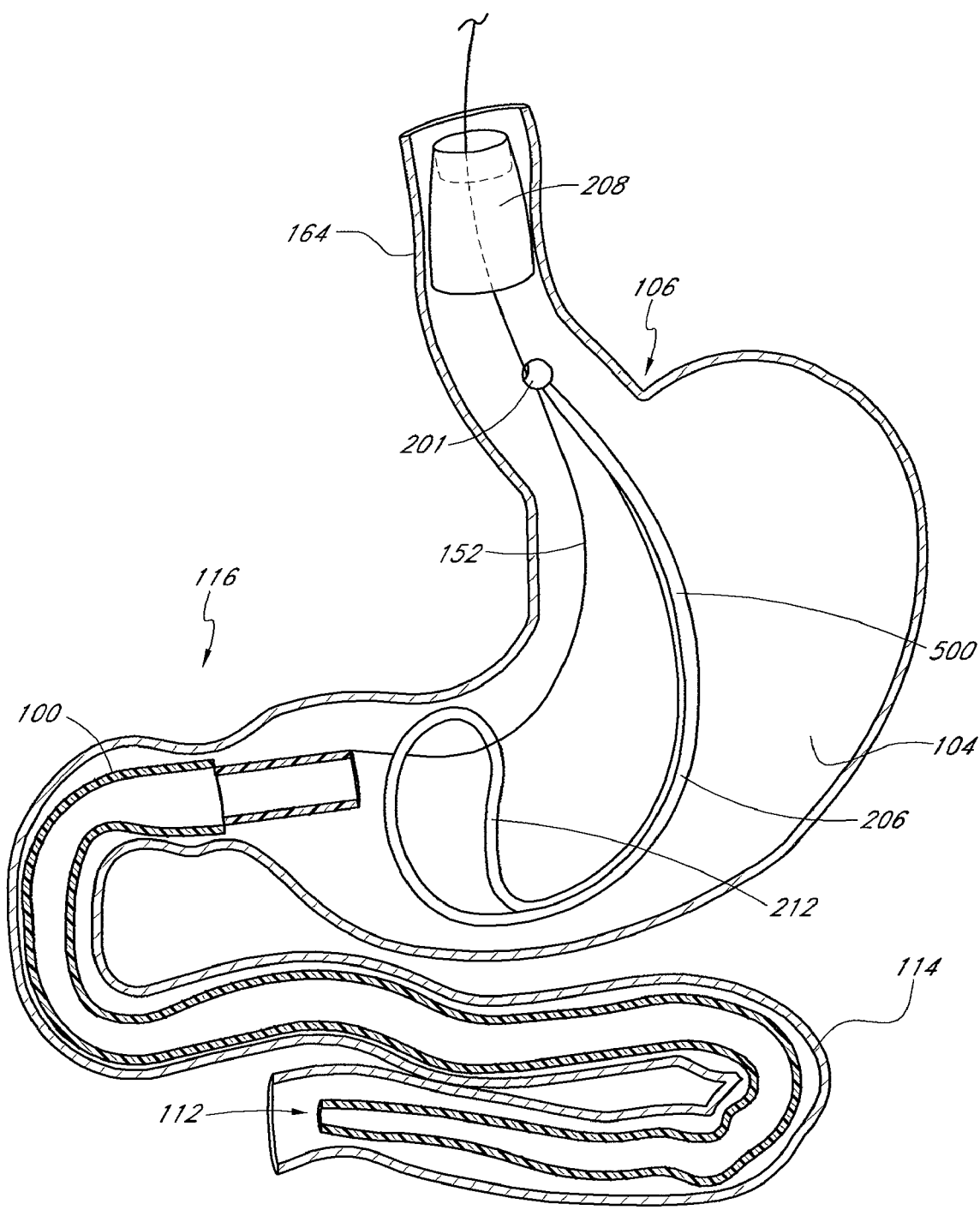
Figure 18J:
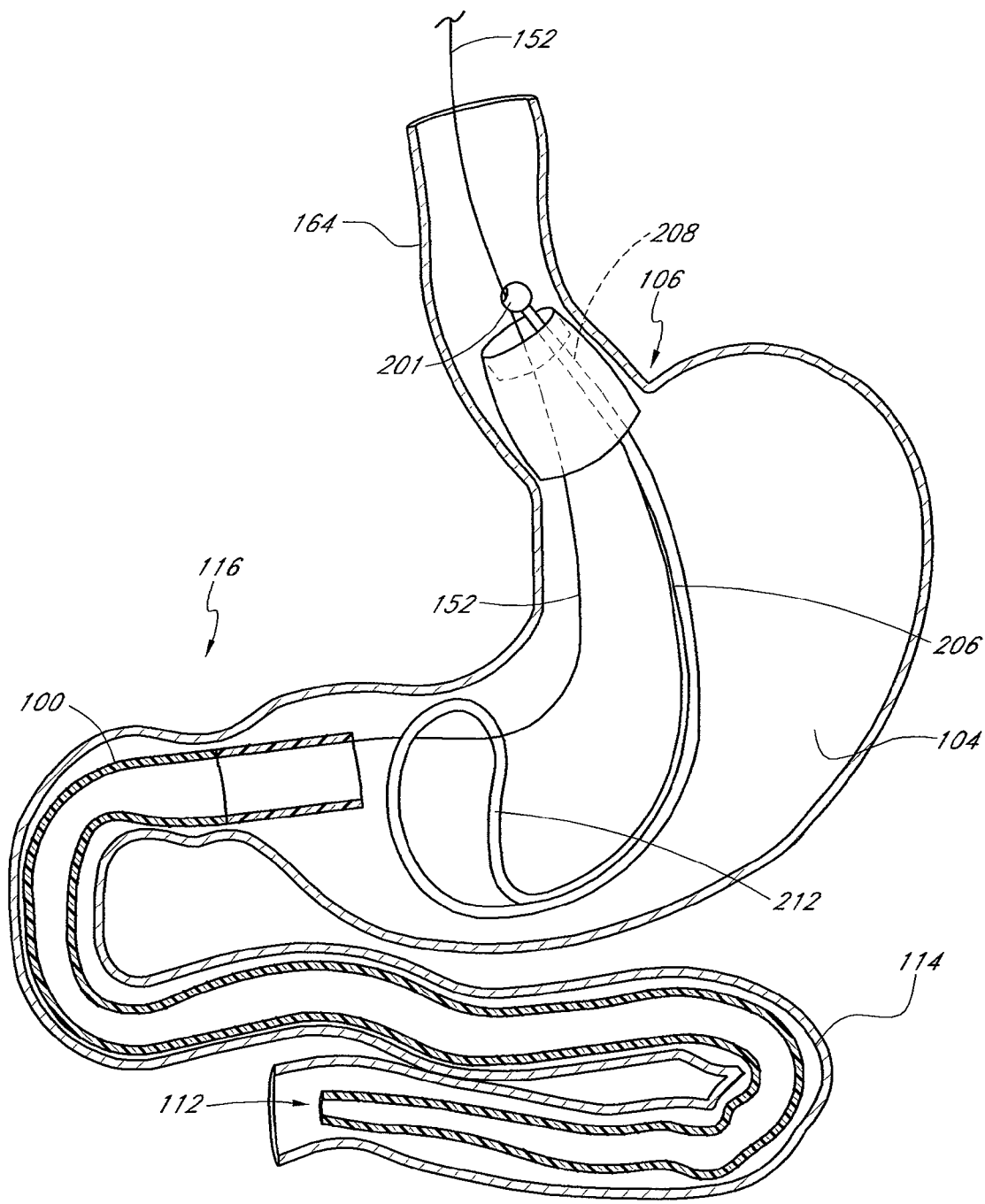
Figure 18K:
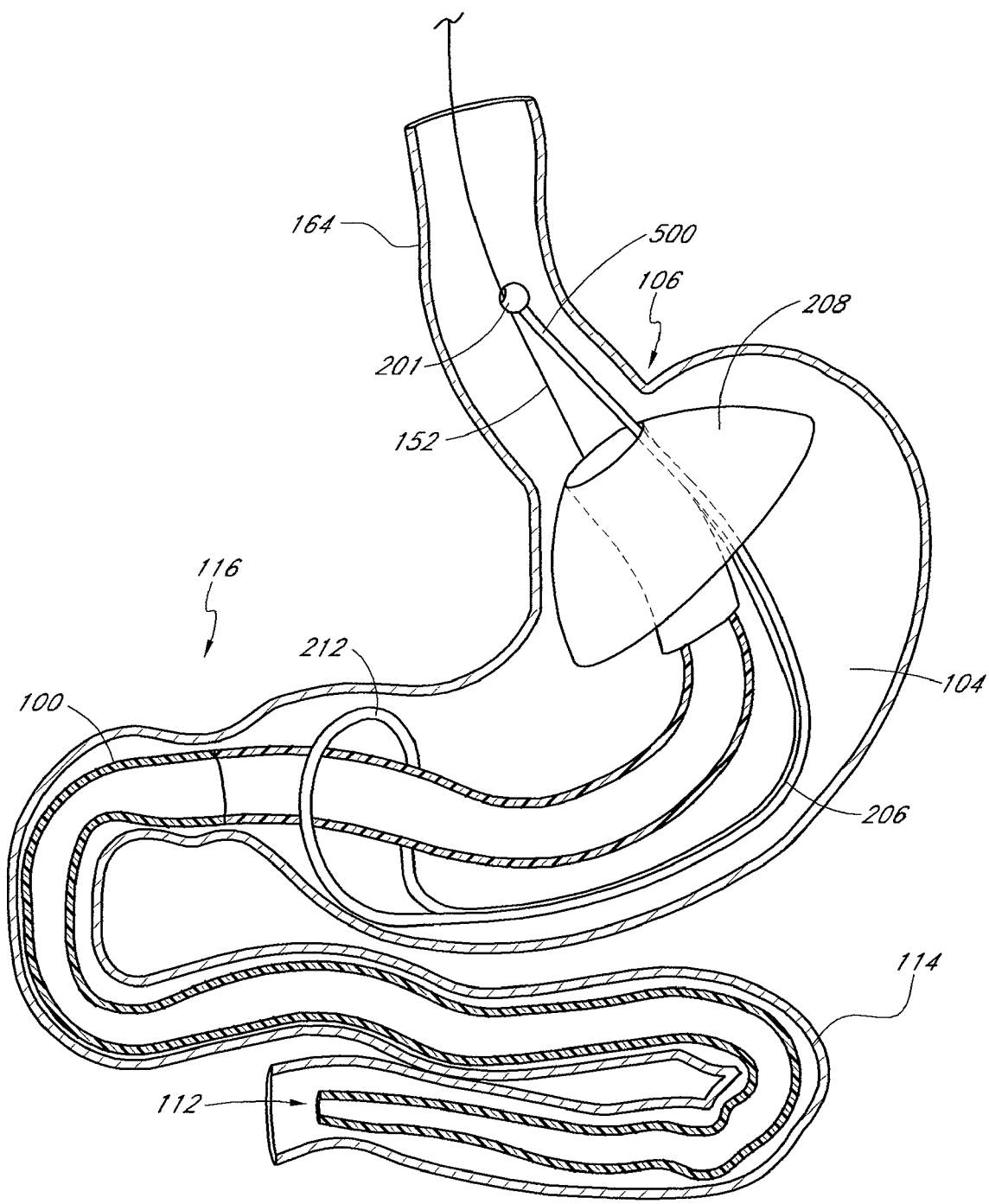
Figure 18L:
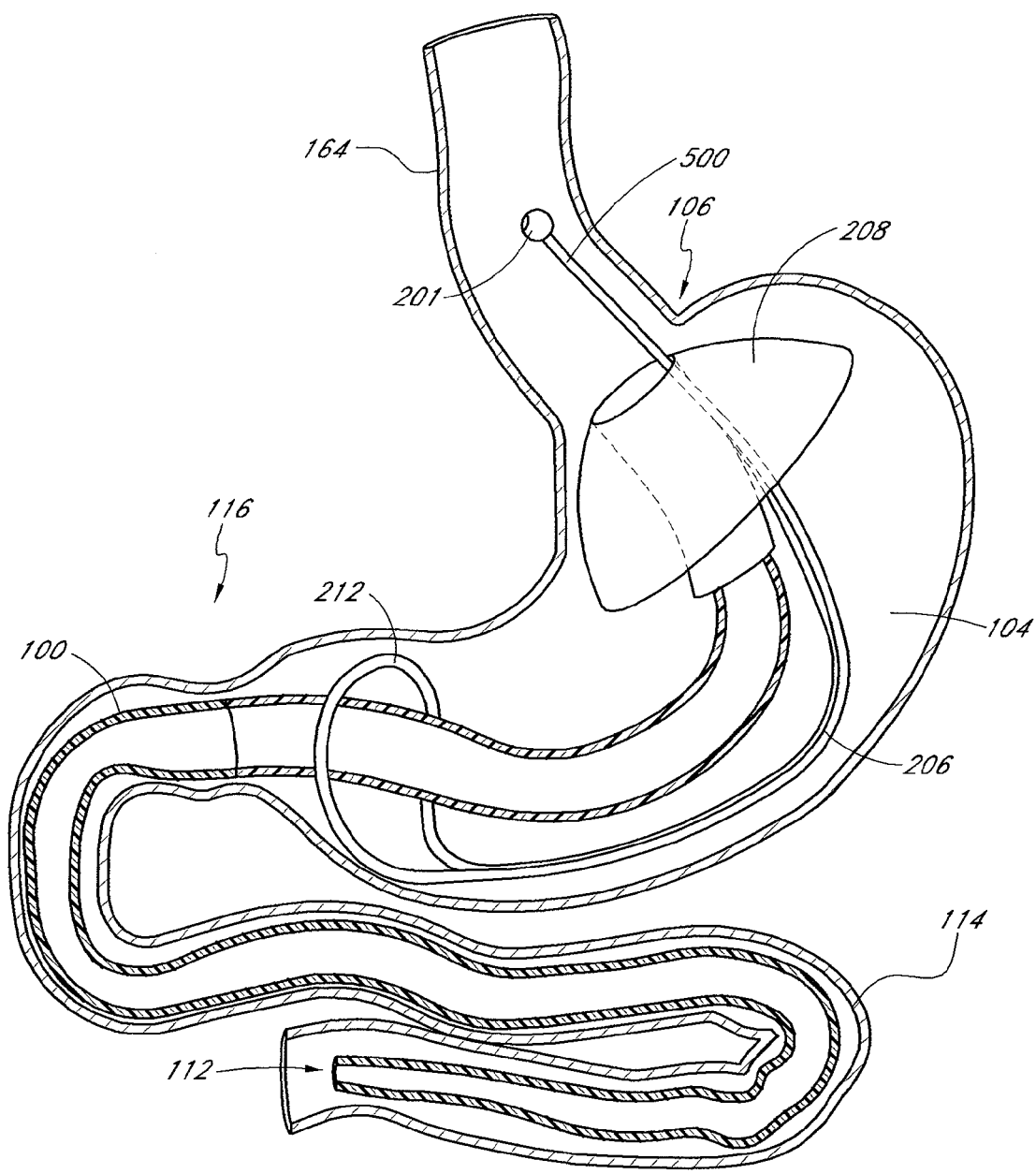

With the sleeve 100 deployed in the intestine 114 and the delivery catheter 400 removed, the intragastric support system can then be introduced perorally over the guidewire 152, as illustrated in FIG. 18F. In one method, each of the components when in its compressed or more linear form, in other words, with the long axis of the proximal orientation element 500 coaxial or substantially coaxial with the long axis of the distal support element 502, would be loaded into a delivery sheath 450 to control advancement into the stomach 104 and allow retrieval of the device before final deployment as shown in FIGS. 18G-18H. Delivery sheaths 450 that provide a similar function as described here are common in the art for other devices such as AAA grafts, percutaneous heart valves and other devices of the sort. In this example, the guidewire 152 is threaded through the proximal orientation element 500 and the loop of the pyloric support element 212 of the distal support element 502 outside of the body before advancement. In one preferred embodiment, the proximal orientation element 500 and the distal support element including pyloric element 212 and the arcuate support element 206 are all one structure. This portion of the intragastric support system 199 is preferably in a first low crossing profile configuration for delivery into the GI tract, as shown schematically in FIG. 18F and can be later expanded to a second post-delivery configuration, as shown schematically in FIG. 18H and described elsewhere in the disclosure. The system can be moved down the guidewire 152 through the oral cavity until the pyloric support element 212 is positioned near the pylorus 116. The dome shaped element 208, which can be other shapes in certain embodiments as previously described, can then be pushed down into the proximal stomach over the guidewire 152. Ideally, the dome shaped element 208 will be advanced while in a smaller profile and is advanced over the proximal orientation element 500 as shown in FIG. 7J. This smaller profile can be achieved by rolling the device or collapsing the device like an umbrella and loading into a delivery sheath (not shown). The dome element 208 can then be deployed and locked into a desired position on the element(s) of the intragastric support system that is already in place, such as near the gastroesophageal junction, and secured in place. It can lock onto the system using a snap fit connection, bayonet style lock, adhesive or by using a endoscopically placed suture, staple or other anchor. Alternatively, the dome 208 and the support elements 500, 206, 212 comprising the intragastric support system can be assembled outside the body and forced into a small enough crossing profile by nature of any of the previously described configurations of these devices so that they can be deployed all at once as opposed to in stages. The IGS system would be compressed and loaded into a delivery sheath 450 as shown in FIG. 19C. The wire 152 would be threaded through the IGS system 199 in the delivery sheath 450 outside the body. The delivery sheath 450 would be advanced over the wire 152 into the stomach 104 and then a plunger 452 would be advanced in the sheath 450 to eject the IGS 199 into the stomach 104. Alternatively, the sheath 450 could be retracted and the plunger 452 held in place so the retraction of the sheath 452 exposes the IGS 199 and allows it to take its biased state. Next, the sleeve 100 can be pulled proximally by pulling on wire 152 through the pyloric support element 212 and up to the dome element 208, as shown in FIG. 18K. In some embodiments, the dome element 208 and proximal sleeve are configured such that a rotation tool can be used to lock the two into place. Alternatively, there could be a snap fit connection with an outward biased element in the proximal end of the sleeve, an interference fit, hook and loop connectors, adhesives could be used to connect the devices, or they could be connected with the use of endoscopic attachment methods previously described. Following deployment of the system, the guidewire 152 can be removed, as illustrated in FIG. 18L as previously described. If desired, a radioopaque contrast medium, such as barium, can be introduced into the esophagus 164 prior to removal of the guidewire 152 (or swallowed by the patient at a later time) in order to observe for any undesired leaking around the sleeve 100. The use of delivery sheaths 452 is not mandatory for any or all of the components. If the components are designed such that they can be in a deliverable state with out being constrained to maintain a small enough profile for peroral delivery the delivery sheath 450 may not be necessary, especially if an esophageal overtube is in place.

Figure 19A:
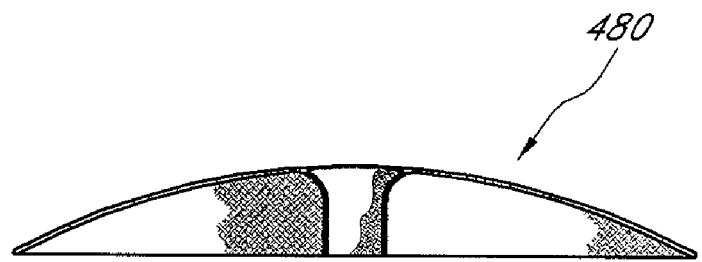
Figure 19B:
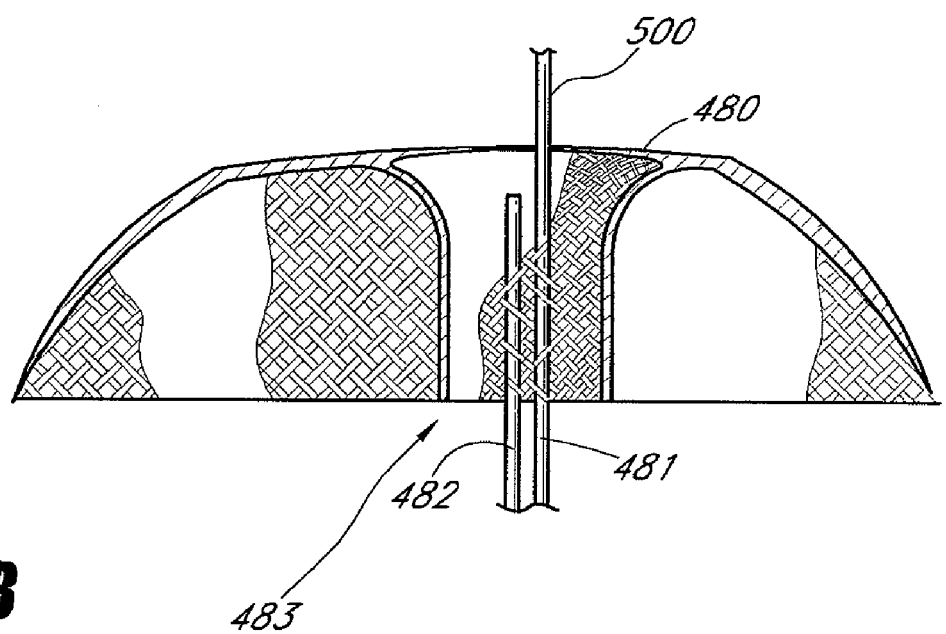

Optionally, the order of the implantation can be changed. In another embodiment, the distal support element 502 is placed in the stomach first in one piece. The elements including the proximal orientation element 500, arcuate support element 206 and pyloric support element 212 are made out of a continuous piece of nitinol wire with one end of the nitinol wire stopping at the atraumatic tip 201 of the proximal orientation element 500 and the other end ending where the dome 208 is attached after making a bend, such as an approximately 180° bend to form the pyloric support element 212 as shown in FIGS. 19A-19D. The dome 208 in this embodiment could be made out of woven nitinol that is dipped in silicone or covered by spray coated silicone or other material as previously disclosed. A cut-away view of a nitinol dome 480 is shown in FIG. 19A. The dome 480 is preattached to the nitinol wire 481 through any of the mechanism that would be known to those with knowledge of this art including thermal bonding, adhesives, laser welding, etc. In an alternate embodiment, the nitinol wire 481 of the main construct 483 is threaded through the weaves of the nitinol dome 480. Then the entire construct 483 is dipcoated in silicone. This device can incorporate any of the atraumatic tip designs previously described for the esophageal post and coatings or features for the rest of the construct. As shown in FIG. 19B, this device made of a shape memory alloy can be placed in a relaxed state in a straightened or linear orientation with the dome 480 collapsed down around the straightened support element or it could be forced into this configuration using a crimping or loading device to help load the compressed IGS 198 into the delivery sheath 450 (shown in FIG. 19C). It is then loaded into a delivery sheath 450, which can be a larger catheter that can fit down the esophagus or esophageal overtube and is large enough to hold the collapsed construct 198. The delivery sheath 450 and intragastric support system 198 in a low crossing profile configuration is shown in FIG. 19C. The delivery sheath 450 is then advanced into the distal end of the stomach and as the sheath 450 is retracted a pusher element 452 or plunger in the sheath 450 keeps the construct 198 in place and it expands into its biased form as the sheath 450 is retracted. After the device 198 expands, the delivery catheter 400 (not shown) is advanced through the center of the expanded device 198 to deliver the sleeve 100. This can be accomplished using the toposcopic delivery methods previously described. However in this case, the delivery catheter 400 would be placed down the esophagus, through the hole in the nitinol dome 480 that aligns with the esophagus, through the pyloric support element 212 and into the pylorus 116. Next, the sleeve 100 would be deployed as described, the delivery catheter 400 would stay attached to the sleeve 100, and when it is retracted it would pull the proximal end of the sleeve 100 up to the attachment point in the nitinol dome 480. In this case the delivery catheter 400 would replace the function of the guidewire 152 in FIGS. 18A-18L. The sleeve 100 would then be attached to a support element such as the dome as previously described and the delivery catheter 400 would release the sleeve 100 and be removed from the body.

In yet another embodiment, the sleeve could be attached to the intragastric support system before implantation. In this method, the intragastric support system (IGS) would be collapsed or crimped down around the delivery catheter with the sleeve attached and inverted as shown in FIG. 19D. FIG. 19D is a cut-away view of an IGS delivery sheath 450 with the intragastric support system 198 loaded with the delivery catheter 400 and sleeve 100. The intragastric support system 198 would have to be able to fit in the space between the delivery catheter 400 and the IGS delivery sheath 450. The sleeve 100 would be attached at the hole in the dome 480 and lay distally along the outside of the sleeve delivery catheter 400 until it is through the pyloric support element 212 where it would then invert around the end 402 of the delivery catheter 400 and up through its center. The entire system 198 would then be loaded into an IGS delivery sheath 450. The loaded IGS delivery sheath 450 would be advanced to the pylorus, as shown in FIG. 19E. The delivery catheter 400 would be advanced slightly out past the end of the IGS delivery sheath 450 until the tip of the sleeve delivery catheter 400 is past the pylorus as shown in FIG. 19F, then the sleeve 100 would be deployed toposcopically as depicted in FIG. 19G. Then the IGS delivery sheath 450 would be fully retracted allowing the IGS system to expand to its natural state as shown in FIGS. 19H-19I. When it expands it would release the sleeve delivery catheter 400 so it would then be withdrawn and the entire system would be in place with the sleeve 100 deployed in the small intestine.

While delivery of the sleeve as described herein has generally focused on toposcopic delivery, it should be noted that any of the sleeve delivery methods as previously described in prior applications or known in the art, such as the Kagan '148 application, could be used including using a pushing catheter, peristaltic delivery, double balloon enteroscopic delivery, etc.

In the above described disclosure, it is most preferred that there is as little risk as possible of damage to the esophagus during any of the implantation steps. Thus before any of the devices as described are advanced perorally, it is preferred that an overtube would be placed. Overtubes such as those described in the Dann '605 application, may be used for delivery. The overtube may be only long enough to protect the esophagus, or it may be long enough, such as at least about 100 cm, 110 cm 120 cm, 130 cm, 140 cm, 150 cm or longer, to reach the pylorus. If the later, it could be advanced with the delivery catheter and the inverted sleeve in its lumen and used to approach or cannulate the pylorus for toposcopic delivery of the sleeve. After sleeve delivery, the overtube would then be retracted to the level of the GEJ for the rest of the procedure.

Figure 20A:
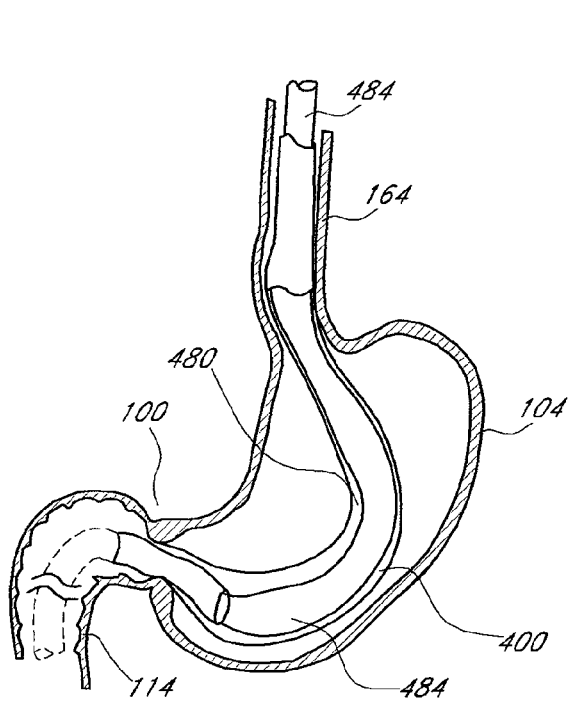
FIGS. 20A-E schematically illustrate another method for delivering an intragastric support system, according to one embodiment of the invention.
Figure 20B:
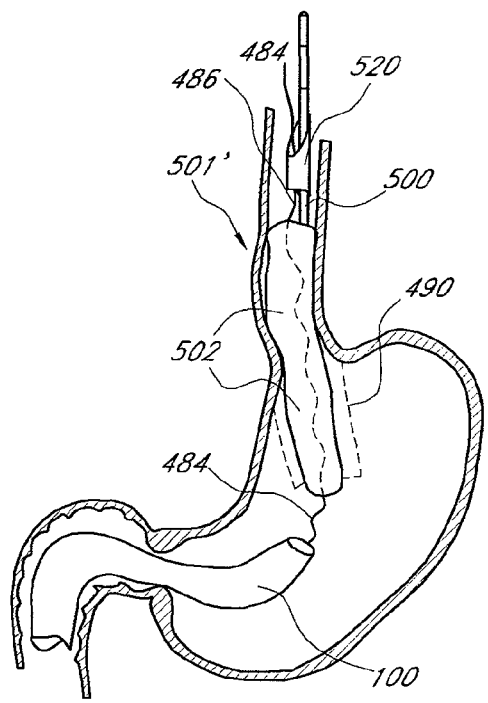
Figure 20C:
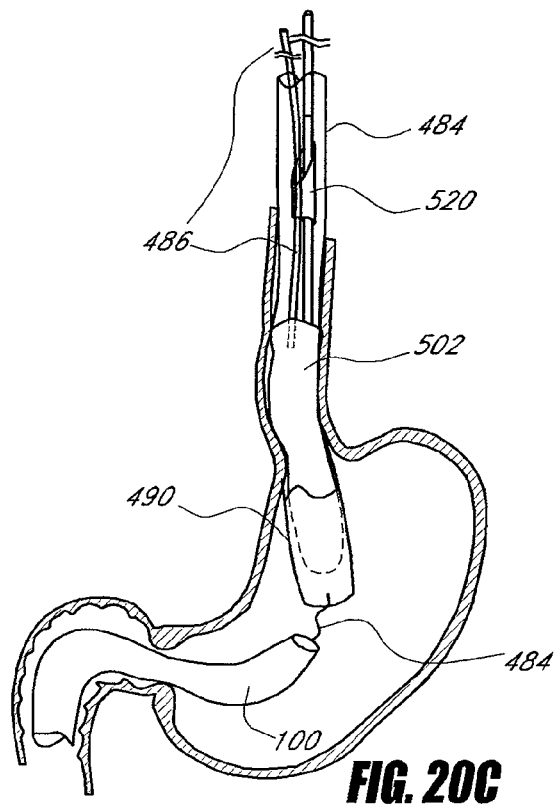

In some embodiments, an intragastric support system, such as illustrated, for example, in FIGS. 7B-7C may be deployed using the following steps:
(1) Move device to the collinear position (e.g., long axis of proximal orientation element at least substantially collinear (coaxial) with the long axis of the distal support element)
(2) Attach a pushing device to the distal support element
(3) Thread distal support element through guidewire and insert into overtube
(4) Orient the distal support element such that pivot direction is towards greater curve, and away from lesser curve
(5) Insert a small diameter endoscope that rides alongside the proximal orientation element directly proximal to the distal support element.
(6) Fill stomach with air
(7) Push past LES and into the stomach
(8) Once proximal part of the distal support element is into the stomach, remove the pushing rod by pulling back or delinking in (unscrewing, etc.)
(9) A spring mechanism may bias the distal support element to open. Pressing the distal support element against the greater curve of the stomach will increase opening (towards perpendicular position relative to the proximal orientation element)
(10) Once the distal support element passes approximately 30 degrees from normal position, it locks into place.
If sleeve is to be attached:
(11) Sleeve would be delivered in advance of placing IGS into the stomach
(12) Sleeve sutures are threaded through ring support before delivering IGS.
(13) IGS is pushed into stomach as described above
(14) Once in the stomach, sleeve ring in collapsed and pulled up into the food collecting ring of the proximal orientation element
(15) Once in the food collecting ring, sleeve ring is released and opened
(16) By pushing it down with an instrument, it locks into food collecting ring Another method for delivering an IGS system 501, such as the system illustrated, for example, in FIG. 6A above, and includes a gastrointestinal bypass sleeve 100 is schematically illustrated in FIGS. 20A-20E, according to one embodiment of the invention. First, the sleeve 100 is connected to and inverted within a delivery catheter 400, as described in U.S. patent application Ser. No. 11/861,156 filed Sep. 25, 2007, and hereby incorporated by reference in its entirety. Next, as illustrated in FIG. 20A, a long overtube 480 is inserted perorally and advanced into the esophagus 164, stomach 104, and the duodenum 114. The sleeve 100 preferably includes at least one tether 484, such as a suture on its proximal end that can run alongside the delivery catheter 400 and proximally out of the long overtube 480 and preferably secured proximal to the mouth of the patient. The sleeve 100 can then be toposcopically delivered as described in the U.S. patent application Ser. No. 11/861,156. As illustrated in FIGS. 20B-C, the sleeve 100 is then released from the delivery catheter 400 and pushed out of the overtube 480 into the stomach 104. Then, the long overtube 480 and delivery catheter 400 are removed, and a shorter overtube 490 inserted (shown in phantom). Next, the proximal ends of the tether(s) 484 are pulled through the esophageal ringed food collector 520 of the proximal orientation element 500 from a distal to proximal direction. The system 501', in its delivery configuration, where the long axis of the proximal orientation element 500 is coaxial with the long axis of the distal support element 502, is then connected to a pusher tool 486. The pusher tool 486 facilitates movement, such as pushing and/or pulling of the intragastric support system 501' relative to a body lumen when the system 501' is being delivered or removed. The pusher tool 486 is preferably releasably coupled to a portion of the system 501' such as, for example, by a threaded connector, lock, or other mechanism.

Figure 20D:
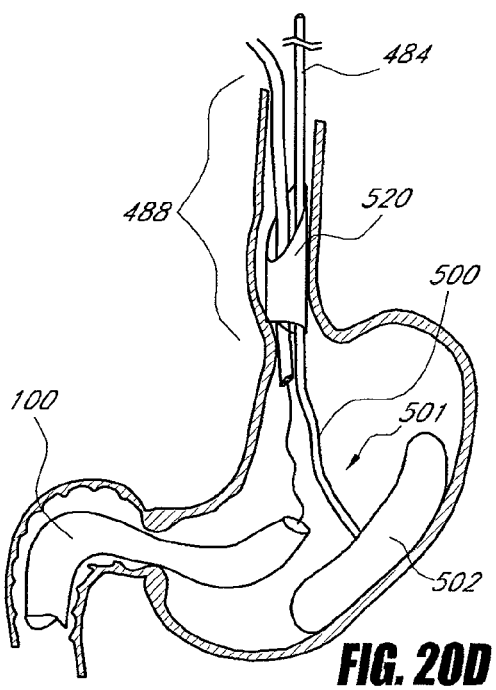
Figure 20E:
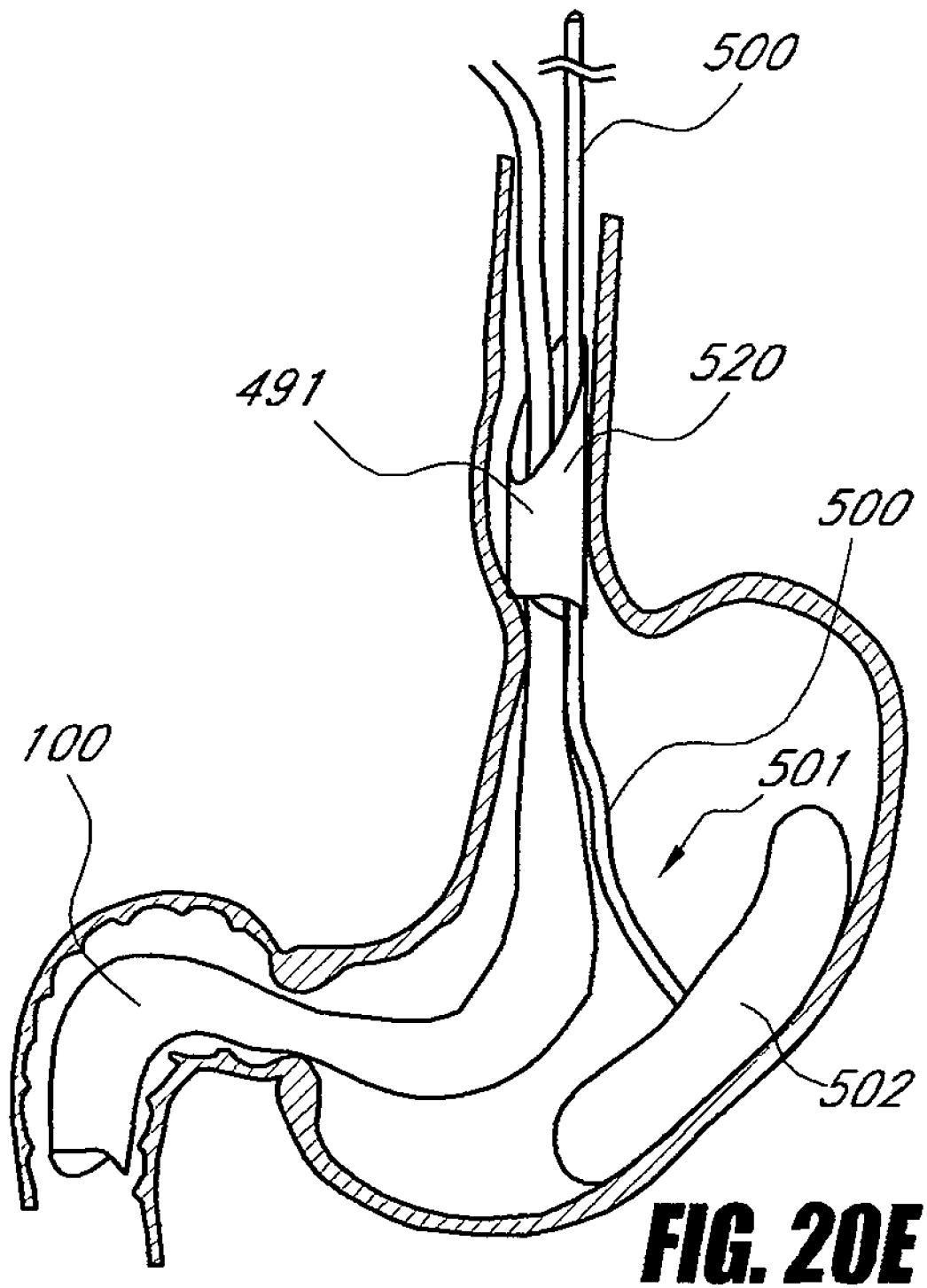

Next, the system 501 releasably connected to pusher tool 486 and endoscope 488 are inserted into the short overtube 490. As shown in FIG. 20D, the intragastric support system 501 is then pushed down into the stomach 104 using the pusher tool 486. The pusher tool 486 can then be decoupled from the intragastric support system 501 and removed from the body. As illustrated in FIGS. 20D-E, the intragastric support system 501 can then be expanded to a implanted configuration where the long axis of the distal support element 502 is not coaxial 501 with the long axis of the proximal orientation element 500, preventing migration of the system 501 either proximally into the esophagus 164 or down into the intestine 114. Next, the proximal end of the bypass sleeve 100 can be pulled proximally into the esophagus 164 by pulling proximally on the tether 484 running through the esophageal food collecting ring 520. The sleeve 100 can then be secured within the inside diameter of the esophageal food collecting ring 520 using, for example, a quick-connect interface 491. The short overtube 490 can then be removed. The tether 484 can then be cut and removed from the body, followed by the endoscope 488.

Figure 21A:
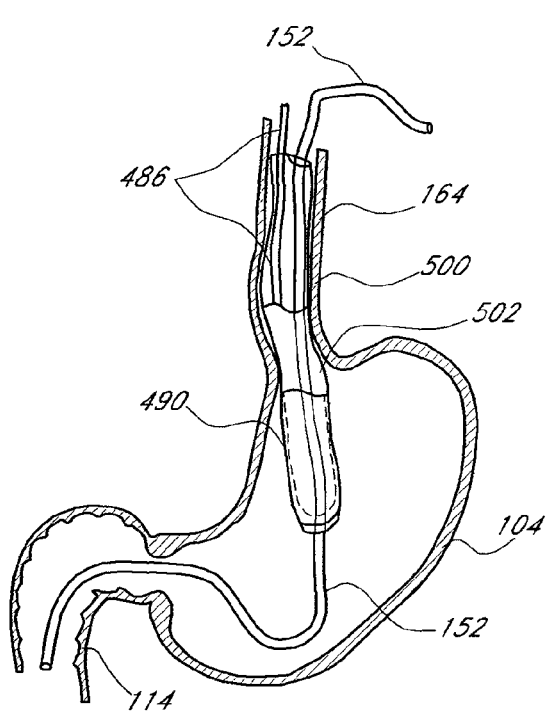
Figure 21B:
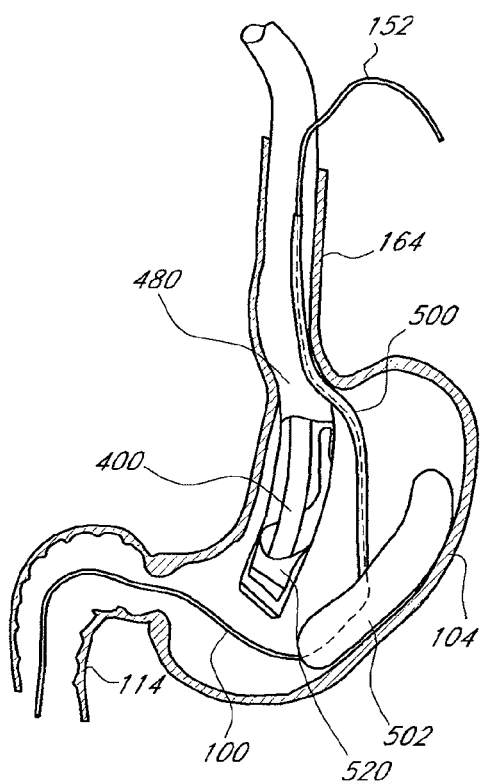
Figure 21C:
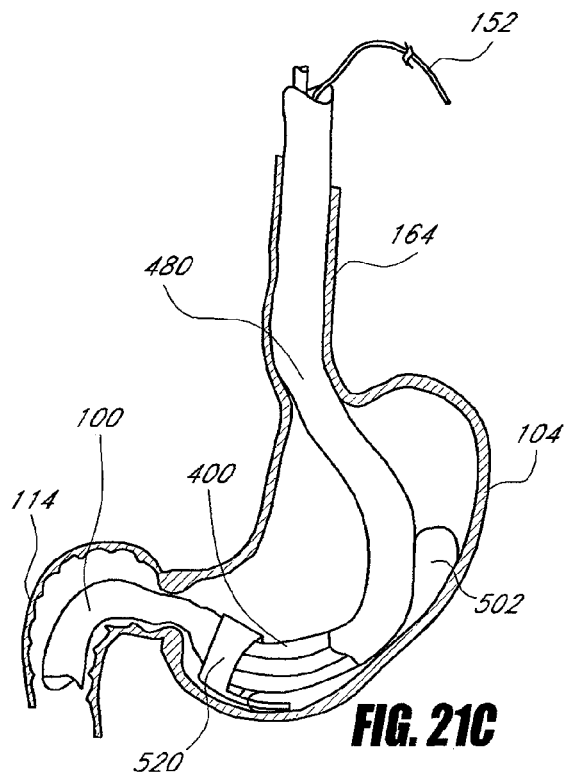
Figure 21D:
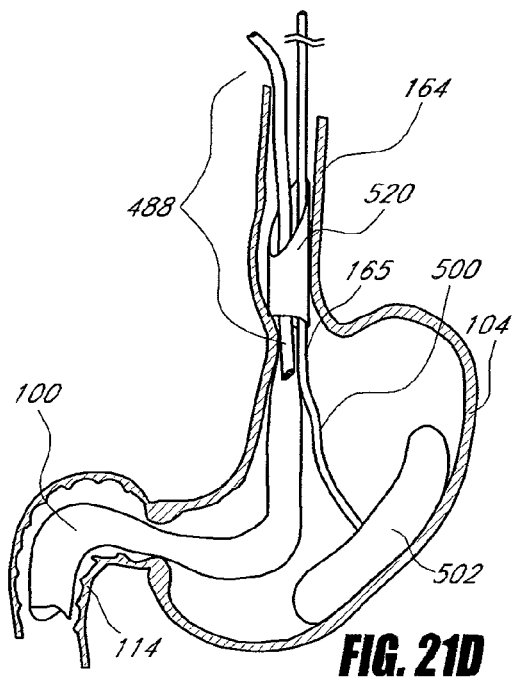

In some embodiments, the intragastric support system 501 can be delivered within the body in multiple pieces, e.g., the distal support element 502 and the proximal orientation element 500 are delivered separately as illustrated schematically in FIGS. 21A-21D. First, a short overtube 490 is delivered perorally to within the esophagus 490, as illustrated in FIG. 21A. Next, a guidewire 152 is threaded distally such that the distal end of the guidewire 152 is in the intestine 114. Then, a portion of the system, such as the distal support element 502, can be releasably coupled to a pusher tool 486 as described above, and deployed over the guidewire 152 (e.g., through a guidewire aperture of the distal support element 502) into the stomach 104. The distal support element 502 is preferably deployed such that the long axis of the distal support element 502 is coaxial with the long axis of the esophagus 164 during delivery. Next, the distal support element 502 is transformed into an implanted configuration where the long axis of the distal support element 502 is not coaxial with the long axis of the proximal orientation element 500, and substantially conforms to the greater curve of the stomach in some embodiments, as illustrated in FIG. 21B. The pushing tool 486 is then detached from the distal support element 502 and removed from the body. Next, the proximal orientation element 500 of the system is attached to a delivery catheter 400. The gastrointestinal bypass sleeve 100 is preattached to the esophageal food collecting ring 520 of the proximal orientation element 500, and inverted into the delivery catheter 400. Next, the short overtube 490 is withdrawn from the body lumen, and replaced by a long overtube 480, which is placed distally into the duodenum 114, as illustrated in FIG. 21C. The guidewire 152 is then fed through a portion of the proximal orientation element 500 configured to receive the guidewire 152. The delivery catheter 400 is then advanced to the distal end of the overtube 480. Any slack from the guidewire 152 is pulled proximally as the delivery catheter 400 is pushed distally. The sleeve 100 can then be toposcopically delivered as previously described. The long overtube 480 can then be pulled back into the esophagus 164. The delivery catheter 400 is removed from the body and an endoscope 488 inserted, as illustrated in FIG. 21D. Next, the proximal orientation element 500 is pushed out into the esophagus 164. The proximal orientation element 500 and the distal support element 502 (which may also include a distal portion of the proximal orientation element 500 when delivered as shown) are connected via the guidewire 152 and coupled together, e.g., via complementary quick connect interfaces 165. The overtube 480, guidewire 152, and scope 488 are then removed from the body, leaving the intragastric support system 501 in place.

System Removal

A method sequence to remove an intragastric support system, such as the system described in FIG. 6A for example, from the GI tract according to one embodiment of the invention is now described. If a sleeve is attached, an operator can reach into the food collecting ring of the proximal orientation element with a grasping element and grab a suture to collapse the sleeve ring and detach from food collecting ring interface. The sleeve can then be pulled out through an overtube. Next, an unlocking instrument can be inserted to release the lock on the distal support element (arch). Once released, a snare may be used to align the distal support element collinear with the proximal orientation element. A pulling instrument is interfaced with the distal support element, and then the device can be pulled up into the overtube.

While this invention has been particularly shown and described with references to embodiments thereof, it will be understood by those skilled in the art that various changes in form and details may be made therein without departing from the scope of the invention. For example, while the embodiments herein have primarily described components of an intragastric support system, the system can also be adapted for positioning in other body lumens, for example, a system with a distal support element configured to be placed in the bladder and the proximal orientation element in a ureter, or a system with a distal support element configured to be placed in the uterus with a proximal orientation element in a fallopian tube, in some embodiments. Furthermore, the intragastric systems and methods disclosed herein can be used or adapted for positioning a device in a patient concurrent with or after bariatric surgery as described, for example, in U.S. Provisional Application No. 61/023,809, hereby incorporated by reference in its entirety, e.g, as described in FIGS. 2-6, 9-12, 14-22, and the accompanying text at paragraphs [0016] to [0018], [0020] to [0051] and [0058] to [0067] of that application.

For all of the embodiments described above, the steps of the methods need not be performed sequentially. While any above-listed applications may have been incorporated by reference for particular subject matter as described earlier in this application, Applicants intend the entire disclosures of the above-identified applications to be incorporated by reference into the present application, in that any and all of the disclosures in these incorporated by reference applications may be combined and incorporated with the embodiments described in the present application.

We claim:

1. An intragastric support system comprising:
a proximal orientation element having a proximal end and a distal end, wherein the proximal orientation element has a diameter sized to fit within the lumen of an esophagus; wherein the long axis of the proximal orientation element is configured to be substantially parallel with the long axis of the esophagus; and
a distal support element configured to reside non-circumferentially against only a portion of the stomach cavity; wherein the distal support element is transformable from a first configuration where a long axis of the distal support element is configured to be substantially parallel with the long axis of the proximal orientation element during delivery to a second configuration where the long axis of the distal support element is configured to be not substantially parallel with the long axis of the proximal orientation element when implanted in the body, wherein the support system is configured such that the proximal end of the proximal orientation element is in the esophagus and the distal end of the proximal orientation element is in the stomach when implanted in the body;

wherein the proximal orientation element further comprises a food-collecting ring.

2. The intragastric support system of claim 1 wherein the food-collecting ring comprises a proximal tapered portion and a distal cylindrical portion.

3. The intragastric support system of claim 2, wherein the proximal tapered portion of the food-collecting ring comprises a first shoulder and a second shoulder, wherein the second shoulder is longitudinally offset from the first shoulder.

4. The intragastric support system of claim 1, further comprising a joint configured to pivotably couple the proximal orientation element to the distal support element.

5. The intragastric support system of claim 4, wherein the joint comprises a ball-and-socket joint.

6. The intragastric support system of claim 4, wherein the joint comprises a hinged joint.

7. The intragastric support system of claim 1, further comprising a gastrointestinal bypass sleeve.

8. The intragastric support system of claim 7, wherein the gastrointestinal bypass sleeve is attached to the food-collecting ring.

9. The intragastric support system of claim 1, wherein the distal support element comprises an enlarged distal end to retain the distal support element within the stomach.

10. The intragastric support system of claim 1, wherein the distal support element comprises a drug reservoir.

11. The intragastric support system of claim 1, wherein the proximal orientation element comprises a rounded proximal head to prevent esophageal trauma.

12. The intragastric support system of claim 1, wherein the proximal orientation element has a variable-length cross section.

13. The intragastric support system of claim 1, wherein the proximal orientation element comprises a plurality of strut members.

14. The intragastric support system of claim 1, wherein the distal support element is transformable between a first reduced configuration and a second expanded configuration.

15. The intragastric support system of claim 1, further comprising a restrictive element operably connected to the food-collecting ring.

16. The intragastric support system of claim 1, further comprising an obstructive element operably connected to the food-collecting ring.

17. A method for treating a patient, comprising:
providing an intragastric support system, the system comprising a proximal orientation element having a proximal end and a distal end, a distal support element, and a food collecting ring;
inserting the proximal orientation element and the distal support element into a gastrointestinal tract lumen, wherein a long axis of the proximal orientation element is substantially parallel to a long axis of the distal support element;
positioning the system such that the proximal end of the proximal orientation element is within the esophagus of a patient and the distal support element is within the stomach of a patient; and
transforming the distal support element such that the long axis of the distal support element is not substantially parallel to the long axis of the proximal orientation element, wherein after the transforming step the distal support element resides non-circumferentially along less than the entirety of the wall of the stomach.

18. The method of claim 17, wherein transforming the distal support element is such that the long axis of the distal support element is substantially perpendicular to the long axis of the proximal orientation element.

19. The method of claim 17, wherein the intragastric support system further comprises a joint configured to pivotably couple the distal support element to the proximal orientation element, the joint having a locked state to prevent movement of the distal support element with respect to the proximal orientation element.

20. The method of claim 19, further comprising the step of:
locking the joint at a position wherein a long axis of the proximal orientation element is at least substantially coaxial with a long axis of the distal support element during delivery; and
unlocking the joint to allow the distal support element to pivot within a range of motion with respect to the proximal orientation element when the distal support element is implanted in the stomach.

* * * * *